US006251404B1

(12) United States Patent
Paul et al.

(10) Patent No.: US 6,251,404 B1
(45) Date of Patent: Jun. 26, 2001

(54) METHOD OF PRODUCING A VACCINE WHICH RAISES AN IMMUNOLOGICAL RESPONSE AGAINST A VIRUS CAUSING A PORCINE RESPIRATORY AND REPRODUCTIVE DISEASE

(75) Inventors: Prem S. Paul; Patrick G. Halbur; Xiang-Jin Meng; Young S. Lyoo, all of Ames, IA (US); Melissa Anne Lum, Mendota Heighta, MN (US)

(73) Assignees: Iowa State University Research Foundation, Ames, IA (US); Solvay Animal Health, Inc., Mendota Heights, MN (US)

( * ) Notice: Subject to any disclaimer, the term of this patent is extended or adjusted under 35 U.S.C. 154(b) by 0 days.

(21) Appl. No.: 08/855,526

(22) Filed: May 13, 1997

Related U.S. Application Data

(60) Division of application No. 08/131,625, filed on Oct. 5, 1993, now Pat. No. 5,695,766, which is a continuation-in-part of application No. 07/969,071, filed on Oct. 30, 1992, now abandoned.

(51) Int. Cl.[7] ........................ A61K 39/12; A61K 39/193; G01N 33/53; C12N 7/00

(52) U.S. Cl. .................................... 424/204.1; 424/218.1; 424/209.1; 424/815; 435/7.1; 435/236; 435/235.1

(58) Field of Search .................................... 435/236, 237, 435/238, 239

(56) References Cited

U.S. PATENT DOCUMENTS

| | | | |
|---|---|---|---|
| 5,419,907 | * | 5/1995 | Paul et al. . |
| 5,476,778 | * | 12/1995 | Chladek et al. . |
| 5,510,258 | * | 4/1996 | Sanderson et al. . |
| 5,587,164 | * | 12/1996 | Sanderson et al. . |
| 5,597,721 | * | 1/1997 | Brun et al. . |
| 5,620,691 | * | 4/1997 | Wensvoort et al. . |
| 5,674,500 | * | 10/1997 | Peeters et al. . |
| 5,677,429 | * | 10/1997 | Benfield . |
| 5,683,865 | * | 11/1997 | Collins et al. . |
| 5,695,766 | * | 12/1997 | Paul et al. . |
| 5,698,203 | * | 12/1997 | Visser et al. . |
| 5,789,388 | * | 8/1998 | Visser et al. . |
| 5,840,563 | * | 11/1998 | Chladek et al. . |
| 5,846,805 | * | 12/1998 | Collins et al. . |
| 5,858,729 | * | 1/1999 | Van Woensel et al. . |
| 5,866,401 | * | 2/1999 | Hesse . |
| 5,888,513 | * | 3/1999 | Duran et al. . |
| 5,910,310 | * | 6/1999 | Heinen et al. . |
| 5,925,359 | * | 7/1999 | Van Woensel et al. . |
| 5,976,537 | * | 11/1999 | Mengeling et al. . |
| 5,989,563 | * | 11/1999 | Chladek et al. . |
| 5,998,601 | * | 12/1999 | Martaugh et al. . |
| 6,001,370 | * | 12/1999 | Burch et al. . |
| 6,015,663 | * | 1/2000 | Wesley et al. . |

OTHER PUBLICATIONS

Meng et al, J. Gen. Virol. 75: 1795–1801, 1994.*
Meng et al, J. Gen. Virol. 79: 2989–2995, 1998.*
Meng et al, J. Gen. Virol. 76: 3181–3188, 1995.*

* cited by examiner

*Primary Examiner*—Nita Minnifield
(74) *Attorney, Agent, or Firm*—Oblon, Spivak, McClelland, Maier & Neustadt, P.C.

(57) ABSTRACT

The present invention provides a vaccine which protects pigs from a virus and/or an infectious agent causing a porcine respiratory and reproductive disease, a method of protecting a pig from a disease caused by a virus and/or an infectious agent which causes a respiratory and reproductive disease, a method of producing a vaccine against a virus and/or an infectious agent causing a porcine reproductive and respiratory disease, and a biologically pure sample of a virus and/or infectious agent associated with a porcine respiratory and reproductive disease, particularly the Iowa strain of porcine reproductive and respiratory syndrome virus (PRRSV), and an isolated polynucleotide which is at least 90% homologous with a polynucleotide obtained from the genome of a virus and/or infectious agent which causes a porcine respiratory and reproductive disease.

3 Claims, 40 Drawing Sheets

FIG. 12A
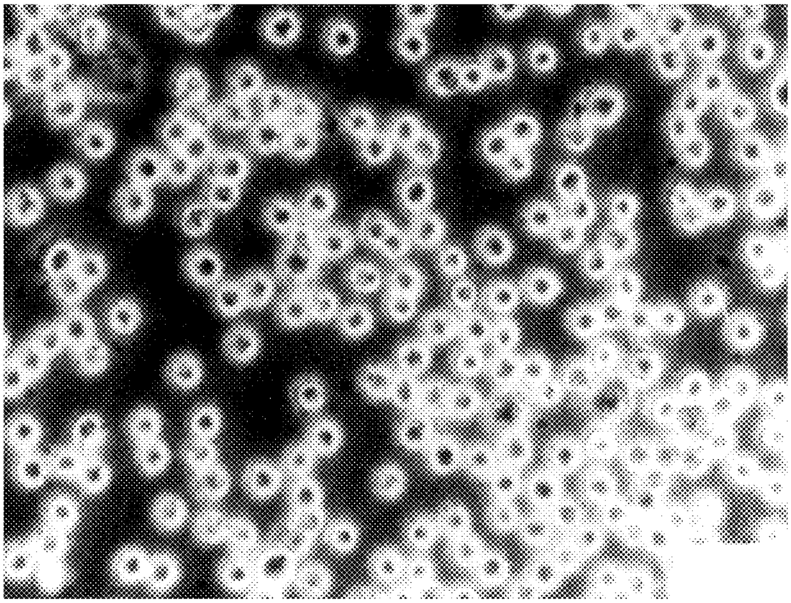
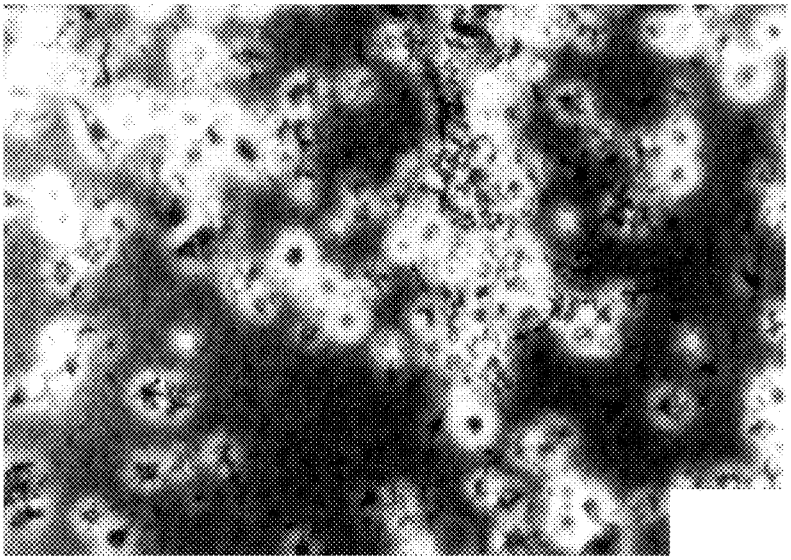
FIG. 12B

FIG. 13A
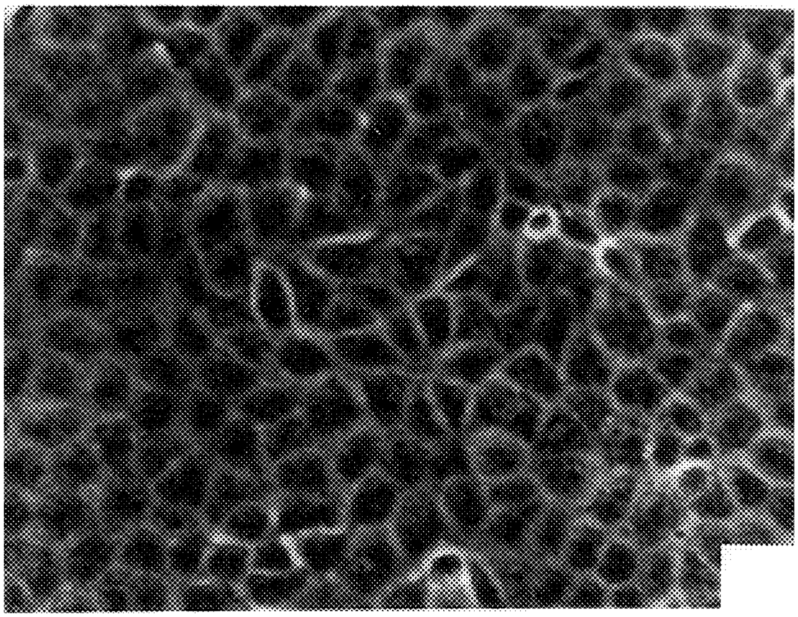
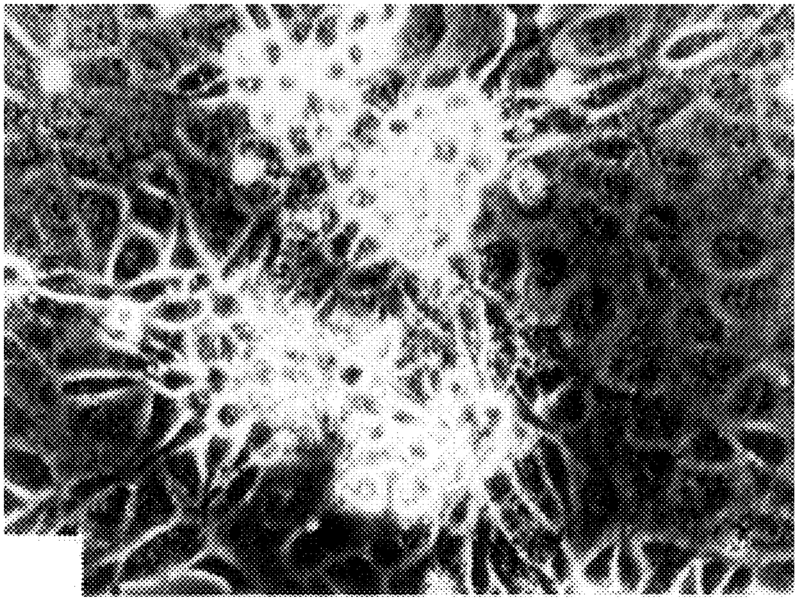
FIG. 13B

FIG. 13C
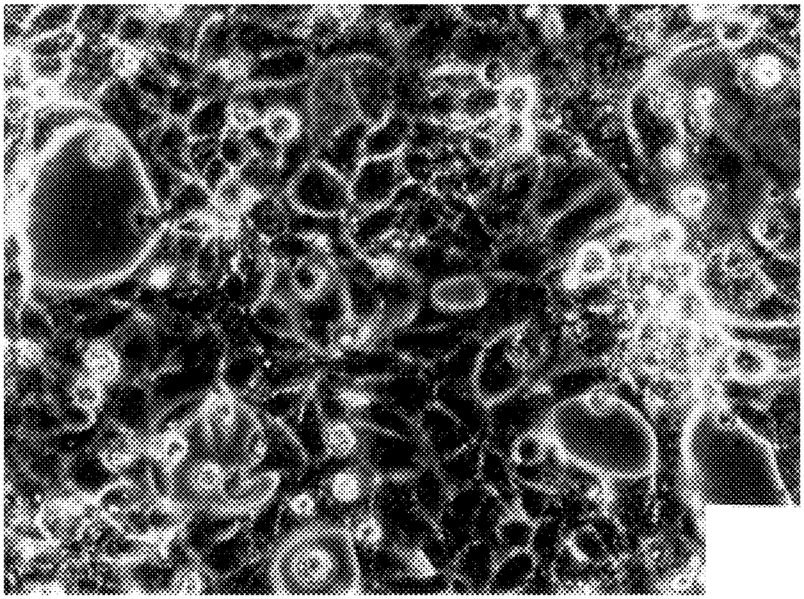
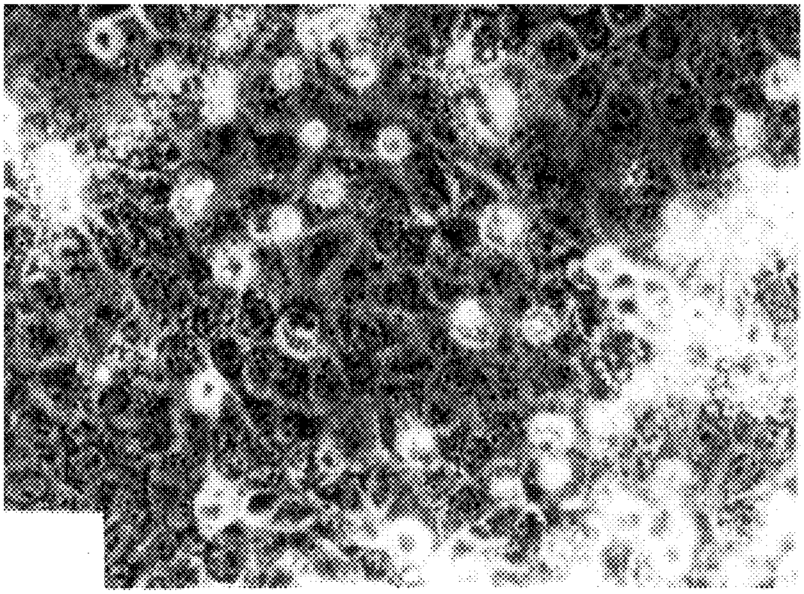
FIG. 13D

FIG. 14A
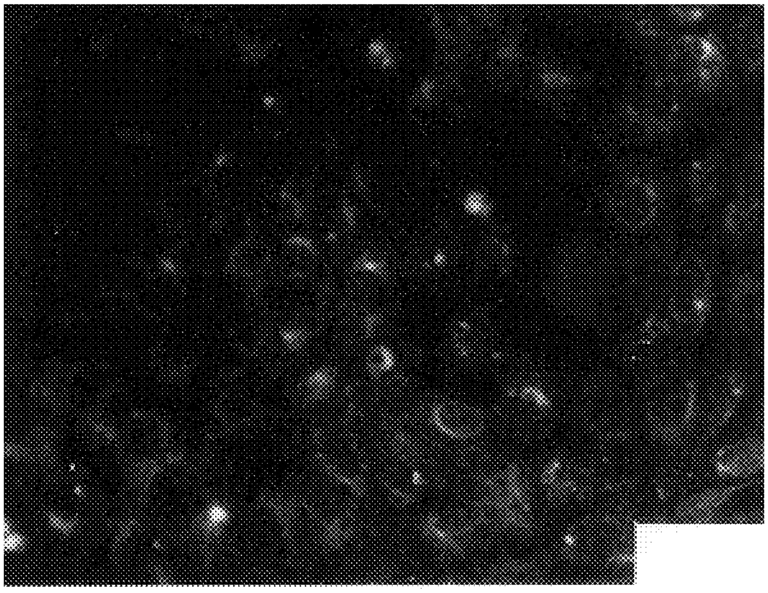
FIG. 14B

FIG. 14C
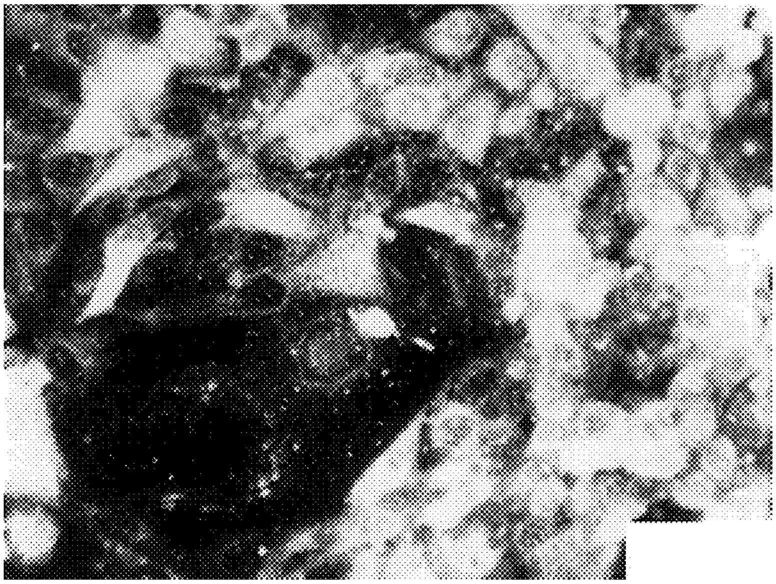
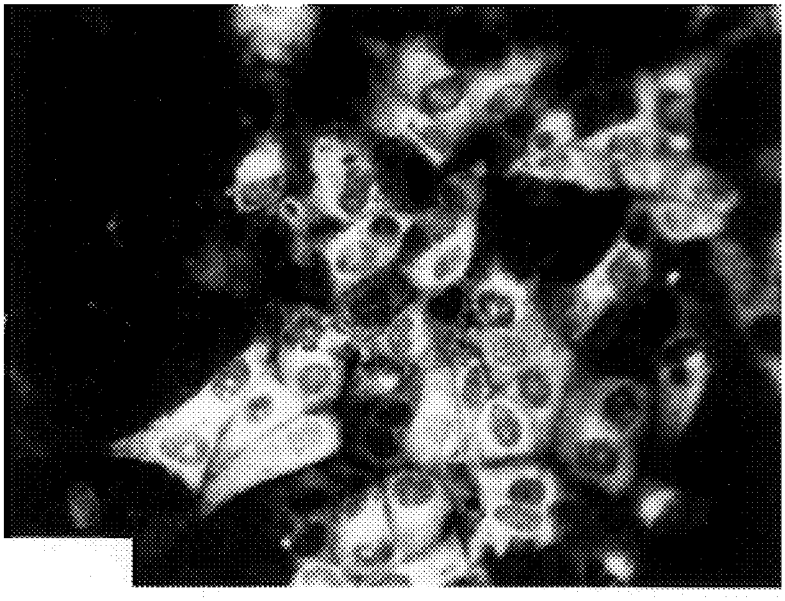
FIG. 14D

```
        10         20         30         40         50
1234567890 1234567890 1234567890 1234567890 1234567890

GGCACGAGCT TTGCTGTCCT CCAAGACATC AGTTGCCTTA GGCATCGCAA   50
CCGTGCTCGA AACGACAGGA GGTTCTGTAG TCAACGGAAT CCGTAGCGTT

CTCGGCCTCT GAGGCGATTC GCAAAGTCCC TCAGTGCCGC ACGGCGATAG  100
GAGCCGGAGA CTCCGCTAAG CGTTTCAGGG AGTCACGGCG TGCCGCTATC

GGACACCCGT GTATATCACT GTCACAGCCA ATGTTACCGA TGAGAATTAT  150
CCTGTGGGCA CATATAGTGA CAGTGTCGGT TACAATGGCT ACTCTTAATA

TTGCATTCCT CTGATCTTCT CATGCTTTCT TCTTGCCTTT TCTATGCTTC  200
AACGTAAGGA GACTAGAAGA GTACGAAAGA AGAACGGAAA AGATACGAAG

TGAGATGAGT GAAAAGGGAT TTAAGGTGGT ATTTGGCAAT GTGTCAGGCA  250
ACTCTACTCA CTTTTCCCTA AATTCCACCA TAAACCGTTA CACAGTCCGT

TCTTTTAGCC TGTCTTTTTG GCATTCTGTT GGCAATTTGA ATGTTTTAAG  300
AGAAAATCGG ACAGAAAAAC CGTAAGACAA CCGTTAAACT TACAAAATTC

TATGTTGGGG AAATGCTTGA CCGCGGGCTG TTGCTCGCAA TTGCTTTTTT  350
ATACAACCCC TTTACGAACT GGCGCCCGAC AACGAGCGTT AACGAAAAAA

TGTGGTGTAT CGTGCCGTCT TGTTTTGTTG CGCTCGTCAG CGCCAACGGG  400
ACACCACATA GCACGGCAGA ACAAAACAAC GCGAGCAGTC GCGGTTGCCC

AACAGCGGCT CAAATTTACA GCTGATTTAC AACTTGACGC TATGTGAGCT  450
TTGTCGCCGA GTTTAAATGT CGACTAAATG TTGAACTGCG ATACACTCGA

GAATGGCACA GATTGGCTAG CTAATAAATT TGACTGGGCA GTGGAGTGTT  500
CTTACCGTGT CTAACCGATC GATTATTTAA ACTGACCCGT CACCTCACAA

TTGTCATTTT TCCTGTGTTG ACTCACATTG TCTCTTATGG TGCCCTCACT  550
AACAGTAAAA AGGACACAAC TGAGTGTAAC AGAGAATACC ACGGGAGTGA

ACTAGCCATT TCCTTGACAC AGTCGGTCTG GTCACTGTGT CTACCGCTGG  600
TGATCGGTAA AGGAACTGTG TCAGCCAGAC CAGTGACACA GATGGCGACC

GTTTGTTCAC GGGCGGTATG TTCTGAGTAG CATGTACGCG GTCTGTGCCC  650
CAAACAAGTG CCCGCCATAC AAGACTCATC GTACATGCGC CAGACACGGG
```

FIG.19A

| 10<br>1234567890 | 20<br>1234567890 | 30<br>1234567890 | 40<br>1234567890 | 50<br>1234567890 | |
|---|---|---|---|---|---|
| TGGCTGCGTT<br>ACCGACGCAA | GATTTGCTTC<br>CTAAACGAAG | GTCATTAGGC<br>CAGTAATCCG | TTGCGAAGAA<br>AACGCTTCTT | TTGCATGTCC<br>AACGTACAGG | 700 |
| TGGCGCTACT<br>ACCGCGATGA | CATGTACCAG<br>GTACATGGTC | ATATACCAAC<br>TATATGGTTG | TTTCTTCTGG<br>AAAGAAGACC | ACACTAAGGG<br>TGTGATTCCC | 750 |
| CAGACTCTAT<br>GTCTGAGATA | CGTTGGCGGT<br>GCAACCGCCA | CGCCTGTCAT<br>GCGGACAGTA | CATAGAGAAA<br>GTATCTCTTT | AGGGGCAAAG<br>TCCCCGTTTC | 800 |
| TTGAGGTCGA<br>AACTCCAGCT | AGGTCACCTG<br>TCCAGTGGAC | ATCGACCTCA<br>TAGCTGGAGT | AAAGAGTTGT<br>TTTCTCAACA | GCTTGATGGT<br>CGAACTACCA | 850 |
| TCCGCGGCTA<br>AGGCGCCGAT | CCCCTGTAAC<br>GGGGACATTG | CAGAGTTTCA<br>GTCTCAAAGT | GCGGAACAAT<br>CGCCTTGTTA | GGAGTCGTCC<br>CCTCAGCAGG | 900 |
| TTAGATGACT<br>AATCTACTGA | TCTGTCATGA<br>AGACAGTACT | TAGCACGGCT<br>ATCGTGCCGA | CCACAAAAGG<br>GGTGTTTTCC | TGCTCTTGGC<br>ACGAGAACCG | 950 |
| GTTTTCTATT<br>CAAAAGATAA | ACCTACACGC<br>TGGATGTGCG | CAGTGATGAT<br>GTCACTACTA | ATATGCCCTA<br>TATACGGGAT | AAGGTGAGTC<br>TTCCACTCAG | 1000 |
| GCGGCCGACT<br>CGCCGGCTGA | GCTAGGGCTT<br>CGATCCCGAA | CTGCACCTTT<br>GACGTGGAAA | TGGTCTTCCT<br>ACCAGAAGGA | GAATTGTGCT<br>CTTAACACGA | 1050 |
| TTCACCTTCG<br>AAGTGGAAGC | GGTACATGAC<br>CCATGTACTG | ATTCGTGCAC<br>TAAGCACGTG | TTTCAGAGTA<br>AAAGTCTCAT | CAAATAAGGT<br>GTTTATTCCA | 1100 |
| CGCGCTCACT<br>GCGCGAGTGA | ATGGGAGCAG<br>TACCCTCGTC | TAGTTGCACT<br>ATCAACGTGA | CCTTTGGGGG<br>GGAAACCCCC | GTGTACTCAG<br>CACATGAGTC | 1150 |
| CCATAGAAAC<br>GGTATCTTTG | CTGGAAATTC<br>GACCTTTAAG | ATCACCTCCA<br>TAGTGGAGGT | GATGCCGTTT<br>CTACGGCAAA | GTGCTTGCTA<br>CACGAACGAT | 1200 |
| GGCCGCAAGT<br>CCGGCGTTCA | ACATTCTGGC<br>TGTAAGACCG | CCCTGCCCAC<br>GGGACGGGTG | CACGTTGAAA<br>GTGCAACTTT | GTGCCCGCAGG<br>CACGGCGTCC | 1250 |
| CTTTCATCCG<br>GAAAGTAGGC | ATTGCGGCAA<br>TAACGCCGTT | ATGATAACCA<br>TACTATTGGT | CGCATTTGTC<br>GCGTAAACAG | GTCCGGCGTC<br>CAGGCCGCAG | 1300 |

```
        10         20         30         40         50
1234567890 1234567890 1234567890 1234567890 1234567890

CCGGCTCCAC TACGGTCAAC GGCACATTGG TGCCCGGGTT AAAAAGCCTC  1350
GGCCGAGGTG ATGCCAGTTG CCGTGTAACC ACGGGCCCAA TTTTTCGGAG

GTGTTGGGTG GCAGAAAAGC TGTTAAACAG GGAGTGGTAA ACCTTGTTAA  1400
CACAACCCAC CGTCTTTTCG ACAATTTGTC CCTCACCATT TGGAACAATT

ATATGCCAAA TAACACCGGC AAGCAGCAGA AGAGAAAGAA GGGGGATGGC  1450
TATACGGTTT ATTGTGGCCG TTCGTCGTCT TCTCTTTCTT CCCCCTACCG

CAGCCAGTCA ATCAGCTGTG CCAGATGCTG GGTAAGATCA TCGCTCACCA  1500
GTCGGTCAGT TAGTCGACAC GGTCTACGAC CCATTCTAGT AGCGAGTGGT

AAACCAGTCC AGAGGCAAGG GACCGGGAAA GAAAAATAAG AAGAAAAACC  1550
TTTGGTCAGG TCTCCGTTCC CTGGCCCTTT CTTTTTATTC TTCTTTTTGG

CGGAGAAGCC CCATTTCCCT CTAGCGACTG AAGATGATGT CAGACATCAC  1600
GCCTCTTCGG GGTAAAGGGA GATCGCTGAC TTCTACTACA GTCTGTAGTG

TTTACCCCTA GTGAGCGTCA ATTGTGTCTG TCGTCAATCC AGACCGCCTT  1650
AAATGGGGAT CACTCGCAGT TAACACAGAC AGCAGTTAGG TCTGGCGGAA

TAATCAAGGC GCTGGGACTT GCACCCTGTC AGATTCAGGG AGGATAAGTT  1700
ATTAGTTCCG CGACCCTGAA CGTGGGACAG TCTAAGTCCC TCCTATTCAA

ACACTGTGGA GTTTAGTTTG CCTACGCATC ATACTGTGCG CCTGATCCGC  1750
TGTGACACCT CAAATCAAAC GGATGCGTAG TATGACACGC GGACTAGGCG

GTCACAGCAT CACCCTCAGC ATGATGGGCT GGCATTCTTG AGGCATCCCA  1800
CAGTGTCGTA GTGGGAGTCG TACTACCCGA CCGTAAGAAC TCCGTAGGGT

GTGTTTGAAT TGGAAGAATG CGTGGTGAAT GGCACTGATT GACATTGTGC  1850
CACAAACTTA ACCTTCTTAC GCACCACTTA CCGTGACTAA CTGTAACACG

CTCTAAGTCA CCTATTCAAT TAGGGCGACC GTGTGGGGGT AAGATTTAAT  1900
GAGATTCAGT GGATAAGTTA ATCCCGCTGG CACACCCCCA TTCTAAATTA

TGGCGAGAAC CACACGGCCG AAATTAAAAA AAAAAAAA               1938
ACCGCTCTTG GTGTGCCGGC TTTAATTTTT TTTTTTTT
```

FIG.19C

```
0                                                                                                   100
          *         *         *         *         *         *         *         *         *         *
GGCACGAGCTTTGCTGTCCTCCAAGACATCAGTTGCCTTAGGCATCGCAACTCGGCCTCTGAGGCGATTCGCAAAGTCCCTCAGTGCCGCACGGCGATAG
 G  T  S  F  A  V  L  Q  D  I  S  C  L  R  H  R  N  S  A  S  E  A  I  R  K  V  P  Q  C  R  T  A  I>

                                                                                                    200
          *         *         *         *         *         *         *         *         *         *
GGACACCCGTGTATATCACTGTCACAGGCAATGTTACCGATGAGAATTATTTGGATTCCTCTGATCTTCTCATGCTTTCTTCTTGCCTTTTCTATGCTTC
G  T  P  V  Y  I  T  V  T  G  N  V  T  D  E  N  Y  L  D  S  S  D  L  L  M  L  S  S  C  L  F  Y  A  S>

                                                                                                    300
          *         *         *         *         *         *         *         *         *         *
TGAGATGAGTGAAAAGGGATTTAAGGTGGTATTTGGCAATGTGTCAGGCATCTTTTAGCCTGTCTTTTTGCCATTCTGTTGGCAATTTGAATGTTTTAAG
  E  M  S  E  K  G  F  K  V  V  F  G  N  V  S  G  I  F>
                                        M  C  Q  A  S  F  S  L  S  F  C  H  S  V  G  N  L  N  V  L  S>

                                                                                                    400
          *         *         *         *         *         *         *         *         *         *
TATGTTGGGGAAATGCTTGACCGCGGGCTGTTGCTCGCAATTGCTTTTTTTGTGGTGTATCGTGCCGTCTTGTTTTGTTGCGCTCGTCAGCGCCAACGGG
  M  L  G  K  C  L  T  A  G  C  C  S  Q  L  L  F  L  W  C  I  V  P  S  C  F  V  A  L  V  S  A  N  G>

                                                                                                    500
          *         *         *         *         *         *         *         *         *         *
AACAGCGGCTCAAATTTACAGCTGATTTACAACTTGACGCTATGTGAGCTGAATGGCACAGATTGGCTAGCTAATAAATTTGACTGGGCAGTGGAGTGTT
 N  S  G  S  N  L  Q  L  I  Y  N  L  T  L  C  E  L  N  G  T  D  W  L  A  N  K  F  D  W  A  V  E  C>
```

FIG.20A

```
                                                                        600
      *         *         *         *         *         *         *         *         *         *
TTGTCATTTTTCCTGTGTTGACTCACATTGTCTCTTATGGTGCCCTCACTACTAGCCATTTCCTTGACACAGTCGGTCTGGTCACTGTGTCTACCGCTGG
F  V  I  F  P  V  L  T  H  I  V  S  Y  G  A  L  T  T  S  H  F  L  D  T  V  G  L  V  T  V  S  T  A  G>

                                                                        700
      *         *         *         *         *         *         *         *         *         *
GTTTGTTCACGGCCGCTATGTTCTGAGTAGCATGTACGCCGTCTGTGCCCTGGCTGCGTTGATTTGCTTCGTCATTAGGCTTGCGAAGAATTGCATGTCC
 F  V  H  G  R  Y  V  L  S  S  M  Y  A  V  C  A  L  A  A  L  I  C  F  V  I  R  L  A  K  N  C  M  S>

                                                                        800
      *         *         *         *         *         *         *         *         *         *
TGGCGCTACTCATGTACCAGATATACCAACTTTCTTCTGGACACTAAGGGCAGACTCTATCGTTGGCGGTCGCCTGTCATCATAGAGAAAAGGGGCAAAG
 W  R  Y  S  C  T  R  Y  T  N  F  L  L  D  T  K  G  R  L  Y  R  W  R  S  P  V  I  I  E  K  R  G  K>

                                                                        900
      *         *         *         *         *         *         *         *         *         *
TTGAGGTCGAAGGTCACCTGATCGACCTCAAAAGAGTTGTGCTTGATGGTTCCGCGGCTACCCCTGTAACCAGAGTTTCAGCGGAACAATGGAGTCGTCC
                                                                                      M  E  S  S>
V  E  V  E  G  H  L  I  D  L  K  R  V  V  L  D  G  S  A  A  T  P  V  T  R  V  S  A  E  Q  W  S  R  P

                                                                        1000
      *         *         *         *         *         *         *         *         *         *
TTAGATGACTTCTGTCATGATAGCACGGCTCCACAAAAGGTGCTCTTGGCGTTTTCTATTACCTACACGCCAGTGATGATATATGCCCTAAAGGTGAGTC
 L  D  D  F  C  H  D  S  T  A  P  Q  K  V  L  L  A  F  S  I  T  Y  T  P  V  M  I  Y  A  L  K  V  S>
```

FIG.20B

```
                                                                                1100
       *       *       *       *       *       *       *       *       *       *
GCGGCCGACTGCTAGGGCTTCTGCACCTTTTGGTCTTCCTGAATTGTGCTTTCACCTTCGGGTACATGACATTCGTGCACTTTCAGAGTACAAATAAGGT
R  G  R  L  L  G  L  L  H  L  L  V  F  L  N  C  A  F  T  F  G  Y  M  T  F  V  H  F  Q  S  T  N  K  V>

                                                                                1200
       *       *       *       *       *       *       *       *       *       *
CGCGCTCACTATGGGAGCAGTAGTTGCACTCCTTTGGGGGGTGTACTCAGCCATAGAAACCTGGAAATTCATCACCTCCAGATGCCGTTTGTGCTTGCTA
  A  L  T  M  G  A  V  V  A  L  L  W  G  V  Y  S  A  I  E  T  W  K  F  I  T  S  R  C  R  L  C  L  L>

                                                                                1300
       *       *       *       *       *       *       *       *       *       *
GGCCGCAAGTACATTCTGGCCCCTGCCCACCACGTTGAAAGTGCCGCAGGCTTTCATCCGATTGCGGCAAATGATAACCACGCATTTGTCGTCCGGCGTC
 G  R  K  Y  I  L  A  P  A  H  H  V  E  S  A  A  G  F  H  P  I  A  A  N  D  N  H  A  F  V  V  R  R>

                                                                                1400
       *       *       *       *       *       *       *       *       *       *
CCGGCTCCACTACGGTCAACGGCACATTGGTGCCCCGGGTTAAAAAGCCTCGTGTTGGGTGGCAGAAAAGCTGTTAAACAGGGAGTGGTAAACCTTGTTAA
P  G  S  T  T  V  N  G  T  L  V  P  G  L  K  S  L  V  L  G  G  R  K  A  V  K  Q  G  V  V  N  L  V  K>

                                                                                1500
       *       *       *       *       *       *       *       *       *       *
ATATGCCAAATAACACCGGCAAGCAGCAGAAGAGAAAGAAGGGGGATGGCCAGCCAGTCAATCAGCTGTGCCAGATGCTGGGTAAGATCATCGCTCACCA
 Y  A  K>
  M  P  N  N  T  G  K  Q  Q  K  R  K  K  G  D  G  Q  P  V  N  Q  L  C  Q  M  L  G  K  I  I  A  H  Q>
```

FIG.20C

```
                                                                      1600
      *         *         *         *         *         *         *         *         *         *
AAACCAGTCCAGAGGCAAGGACCGGGAAAGAAAAATAAGAAGAAAAACCCGGAGAAGCCCCATTTCCCTCTAGCGACTGAAGATGATGTCAGACATCAC
 N  Q  S  R  G  K  G  P  G  K  K  N  K  K  K  N  P  E  K  P  H  F  P  L  A  T  E  D  D  V  R  H  H>

                                                                      1700
      *         *         *         *         *         *         *         *         *         *
TTTACCCCTAGTGAGCGTCAATTGTGTCTGTCGTCAATCCAGACCGCCTTTAATCAAGGCGCTGGGACTTGCACCCTGTCAGATTCAGGGAGGATAAGTT
F  T  P  S  E  R  Q  L  C  L  S  S  I  Q  T  A  F  N  Q  G  A  G  T  C  T  L  S  D  S  G  R  I  S>

                                                                      1800
      *         *         *         *         *         *         *         *         *         *
ACACTGTGGAGTTTAGTTTGCCTACGCATCATACTGTGCGCCTGATCCGCGTCACAGCATCACCCTCAGCATGATGGGCTGGCATTCTTGAGGCATCCCA
Y  T  V  E  F  S  L  P  T  H  H  T  V  R  L  I  R  V  T  A  S  P  S  A>

                                                                      1900
      *         *         *         *         *         *         *         *         *         *
GTGTTTGAATTGGAAGAATGCGTGGTGAATGGCACTGATTGACATTGTGCCTCTAAGTCACCTATTCAATTAGGGCGACCGTGTGGGGTAAGATTTAAT

      *         *         *
TGGCGAGAACCACACGGCCGAAATTAAAAAAAAAAAAA
```

FIG.20D

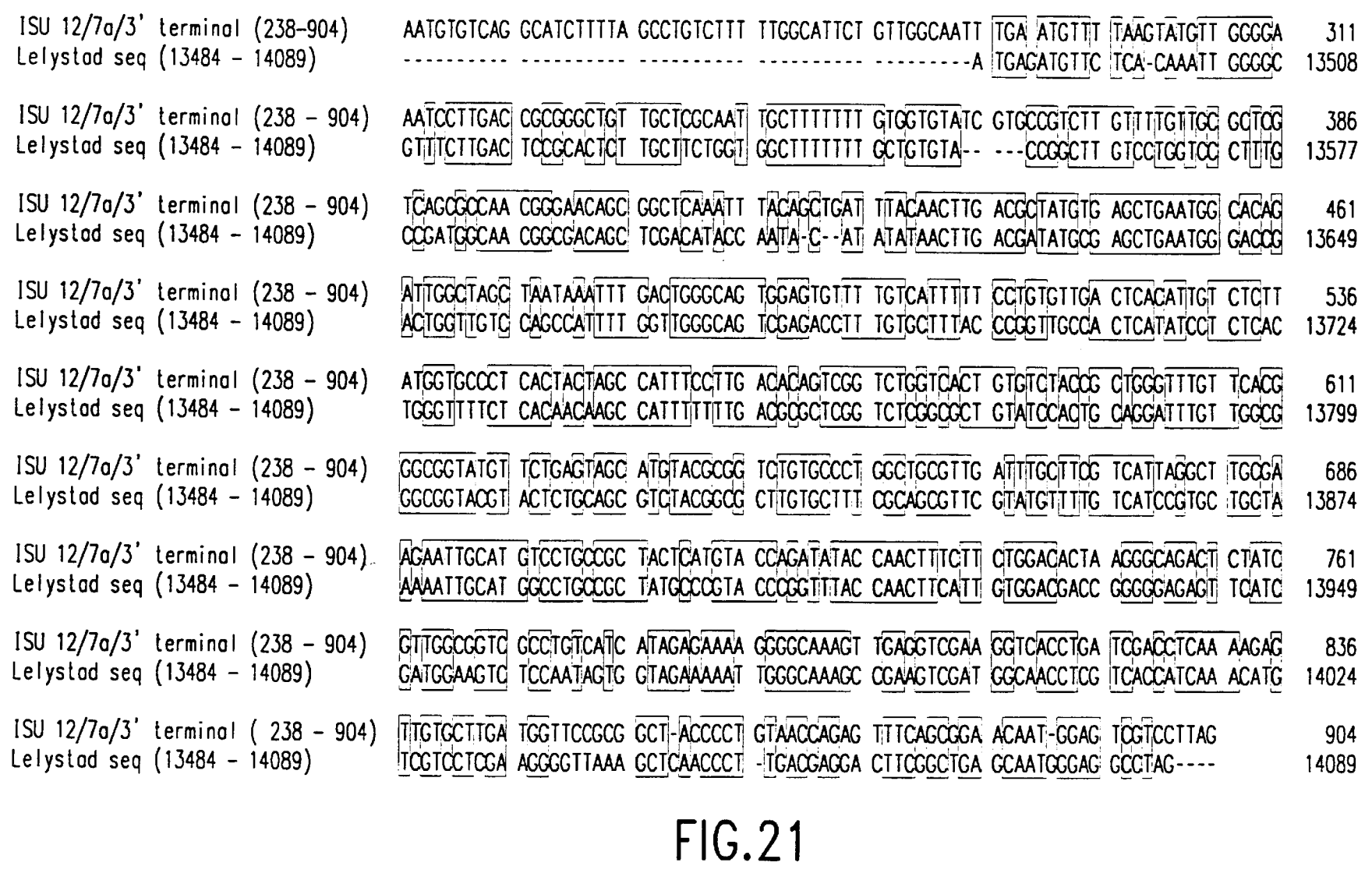

```
ISU 12/7a/3' terminal (238-904)     AATGTGTCAG GCATCTTTTA GCCTGTCTTT TTGGCATTCT GTTGGCAATT TGA ATGTTT TAAGTATGTT GGGGA    311
Lelystad seq (13484 - 14089)        ---------- ---------- ---------- ---------- ---------A TGACATGTTC TCA-CAAATT GGGGC 13508

ISU 12/7a/3' terminal (238 - 904)   AATCCTTGAC CGCGGGCTGT TGCTCGCAAT TGCTTTTTTT GTGGTGTATC GTGCCGTCTT GTTTTGTTGC GCTCG    386
Lelystad seq (13484 - 14089)        GTTTCTTGAC TCCGCACTCT TGCTTCTGGT GGCTTTTTTT GCTGTGTA-- ---CCGGCTT GTCCTGGTCC CTTTG 13577

ISU 12/7a/3' terminal (238 - 904)   TCAGCGCCAA CGGGAACAGC GGCTCAAATT TACAGCTGAT TTACAACTTG ACGCTATGTG AGCTGAATGG CACAG    461
Lelystad seq (13484 - 14089)        CCGATGGCAA CGGCGACAGC TCGACATACC AATA-C--AT ATATAACTTG ACGATATGCG AGCTGAATGG GACCG 13649

ISU 12/7a/3' terminal (238 - 904)   ATTGGCTACG TAATAAATTT GACTGGGCAG TGGAGTGTTT TGTCATTTTT CCTGTGTTGA CTCACATTGT CTCTT    536
Lelystad seq (13484 - 14089)        ACTGGTTGTC CAGCCATTTT GGTTGGGCAG TCGAGACCTT TGTGCTTTAC CCGGTTGCCA CTCATATCCT CTCAC 13724

ISU 12/7a/3' terminal (238 - 904)   ATGGTGCCCT CACTACTAGC CATTTCCTTG ACACAGTCGG TCTGGTCACT GTGTCTACCG CTGGGTTTGT TCACG    611
Lelystad seq (13484 - 14089)        TGGGTTTTCT CACAACAAGC CATTTTTTTG ACGCGCTCGG TCTCGGCGCT GTATCCACTG CAGGATTTGT TGGCG 13799

ISU 12/7a/3' terminal (238 - 904)   GCGCGTATGT TCTGAGTAGC ATGTACGCGG TCTGTGCCCT GGCTGCGTTG ATTTGCTTCG TCATTAGGCT TGCGA    686
Lelystad seq (13484 - 14089)        GCGCGTACGT ACTCTGCAGC GTCTACGGCG CTTGTGCTTT CGCAGCGTTC GTATGTTTTG TCATCCGTGC TGCTA 13874

ISU 12/7a/3' terminal (238 - 904)   AGAATTGCAT GTCCTGCCGC TACTCATGTA CCAGATATAC CAACTTTCTT CTGGACACTA AGGGCAGACT CTATC    761
Lelystad seq (13484 - 14089)        AAAATTGCAT GGCCTGCCGC TATGCCCGTA CCCGGTTTAC CAACTTCATT GTGGACGACC GGGGGAGAGT TCATC 13949

ISU 12/7a/3' terminal (238 - 904)   GTTGGCGGTC GCCTGTCATC ATAGAGAAAA GGGGCAAAGT TGAGGTCGAA GGTCACCTGA TCGACCTCAA AAGAG    836
Lelystad seq (13484 - 14089)        GATGGAAGTC TCCAATAGTG GTAGAAAAAT TGGGCAAAGC CGAAGTCGAT GGCAACCTCG TCACCATCAA ACATG 14024

ISU 12/7a/3' terminal ( 238 - 904)  TTGTGCTTGA TGGTTCCGCG GCT-ACCCCT GTAACCAGAG TTTCAGCGGA ACAAT-GGAG TCGTCCTTAG          904
Lelystad seq (13484 - 14089)        TCGTCCTCGA ACGGGTTAAA GCTCAACCCT -TGACGAGGA CTTCGGCTGA GCAATGGGAG GCCTAG----      14089
```

FIG.21

```
ISU 12/7a/3' terminal (888 - 1413)  AATGGAGTCG TCCTTAGATG ACTTCTGTCA TGATAGCACG GCTCCACAAA AGGTGCTCTT    947
Lelystad seq (14077 - 14598)        -ATGG-GACG --CCTAGACG ATTTTTGCAA CGATCCTATC GCCGCACAAA AGCTCGTGCT  14132

ISU 12/7a/3' terminal (888 - 1413)  GGCGTTTTCT ATTACCTACA CGCCAGTGAT GATATATGCC CTAAAGGTGA GTCGCGGCCG   1007
Lelystad seq (14077 - 14598)        AGCCTTTAGC ATCACATACA CACCTATAAT GATATACGCC CTTAAGGTGT CACGCGGCCG  14192

ISU 12/7a/3' terminal (888 - 1413)  ACTGCTAGGG CTTCTGCACC TTTTGGTCTT CCTGAATTGT GCTTTCACCT TCGGGTACAT   1067
Lelystad seq (14077 - 14598)        ACTCCTGGGG CTGTTGCACA TCCTAATATT TCTGAACTGT TCCTTTACAT TCGGATACAT  14252

ISU 12/7a/3' terminal (888 - 1413)  GACATTCGTG CACTTTCAGA GTACAAATAA GGTCGCGCTC ACTATGGGAG CAGTAGTTGC   1127
Lelystad seq (14077 - 14598)        GACATATGTG CATTTTCAAT CCACCAACCG TGTCGCACTT ACCCTGGGGG CTGTTGTCG-  14311

ISU 12/7a/3' terminal (888 - 1413)  ACTCCTTTGG GGGGTGTACT CAGC--CATA GAAACCTGGA AATTCATCAC CTCCAGATGC   1185
Lelystad seq (14077 - 14598)        -CCCTTCTGT GGGGTGTTTA CAGCTTCACA GAGTCATGGA AGTTTATCAC TTCCAGATGC  14370

ISU 12/7a/3' terminal (888 - 1413)  CGTTTGTGCT TGCTAGGCCG CAAGTACATT CTGGCCCCTG CCCACCACGT TGAAAGTGCC   1245
Lelystad seq (14077 - 14598)        AGATTGTGTT GCCTTGGCCG GCGATACATT CTGGCCCCTG CCCATCACGT AGAAAGTGCT  14430

ISU 12/7a/3' terminal (888 - 1413)  GCAGGCTTTC ATCCGATTGC GGCAAATGAT AACCACGCAT TTGTCGTCCG GCGTCCCGGC   1305
Lelystad seq (14077 - 14598)        GCAGGTCTCC ATTCAATCTC AGCGTCTGGT AACCGAGCAT ACGCTGTGAG AAAGCCCGGA  14490

ISU 12/7a/3' terminal (888 - 1413)  TCCACTACGG TCAACGGCAC ATTGGTGCCC GGGTTAAAAA GCCTCGTGTT GGGTGGCAGA   1365
Lelystad seq (14077 - 14598)        CTAACATCAG TGAACGGCAC TCTAGTACCA GGACTTCGGA GCCTCGTGCT GGGCGGCAAA  14550

ISU 12/7a/3' terminal (888 - 1413)  AAAGCTGTTA AACAGGGAGT GGTAAACCTT GTTAAATATG CCAAATAA               1413
Lelystad seq (14077 -14598)         CGAGCTGTTA AACGAGGAGT GGTTAACCTC GTCAAGTATG GCCGGTAA              14598
```

FIG.22

```
Lelystad seq (14588 - 14974)          ATGGCCGGTA AAAACCAGA- GCCAGAAGAA AAAGAAAAGT A-CAG----C  14632
ISU 12/7a/3' terminal (1403 - 1774)   ---------- --------AT GCCAAATAAC ACCGGCAAGC AGCAGAAGAG   1434

Lelystad seq (14588 - 14974)          TCCGATGGGG AATGGCCAGC CAGTCAATCA ACTGTGCCAG TTGCTGGGTG  14681
ISU 12/7a/3' terminal (1403 - 1774)   AAAGAAGGGG GATGGCCAGC CAGTCAATCA GCTGTGCCAG ATGCTGGGT-   1483

Lelystad seq (14588 - 14974)          CAATGATAAA GTCCCAGCGC CAGCAACCTA GGGG--A-GG ACAGGCCAAA  14728
ISU 12/7a/3' terminal (1403 - 1774)   -AA-GATCAT CGCTCACCAA AACCAGTCCA GAGGCAAGGG ACCGG---GA   1528

Lelystad seq (14588 - 14974)          AAGAAAAA-- ----G----- -CCTGAGAAG CCACATTTTC CCCTGGCTGC  14766
ISU 12/7a/3' terminal (1403 - 1774)   AAGAAAAATA AGAAGAAAAA CCCGGAGAAG CCCCATTTCC CTCTAGCGAC   1578

Lelystad seq (14588 - 14974)          TGAAGATGAC ATCCGGCACC ACCTCACCCA GACTGAACGC TCCCTCTGCT  14816
ISU 12/7a/3' terminal (1403 - 1774)   TGAAGATGAT GTCAGACATC ACTTTACCCC TAGTGAGCGT CAATTGTGTC   1628

Lelystad seq (14588 - 14974)          TGCAATCGAT CCAGACGGCT TTCAATCAAG GCGCAGGAAC -TGCGTCGCT  14865
ISU 12/7a/3' terminal (1403 - 1774)   TGTCGTCAAT CCAGACCGCC TTTAATCAAG GCGCTGGGAC TTGCACC-CT   1677

Lelystad seq (14588 - 14974)          TTCATCCAGC GGGAAGGTCA GTTTTCAGGT TGAGTTTATG CTGCCGGTTG  14915
ISU 12/7a/3' terminal (1403 - 1774)   GTCAGATTCA GGGAGGATAA GTTACACTGT GGAGTTTAGT TTGCCTACGC   1727

Lelystad seq (14588 - 14974)          CTCATACAGT GCGCCTGATT CGCGTGACTT CTACATCCGC CAGTCAGGGT  14965
ISU 12/7a/3' terminal (1403 - 1774)   ATCATACTGT GCGCCTGATC CGCGTCACAG CATCACCC-T CAG-CATGA-   1774

Lelystad seq (14588 - 14974)          GCAAGTTAA                                               14974
ISU 12/7a/3' terminal (1403 - 1774)                                                            1774
```

FIG.23

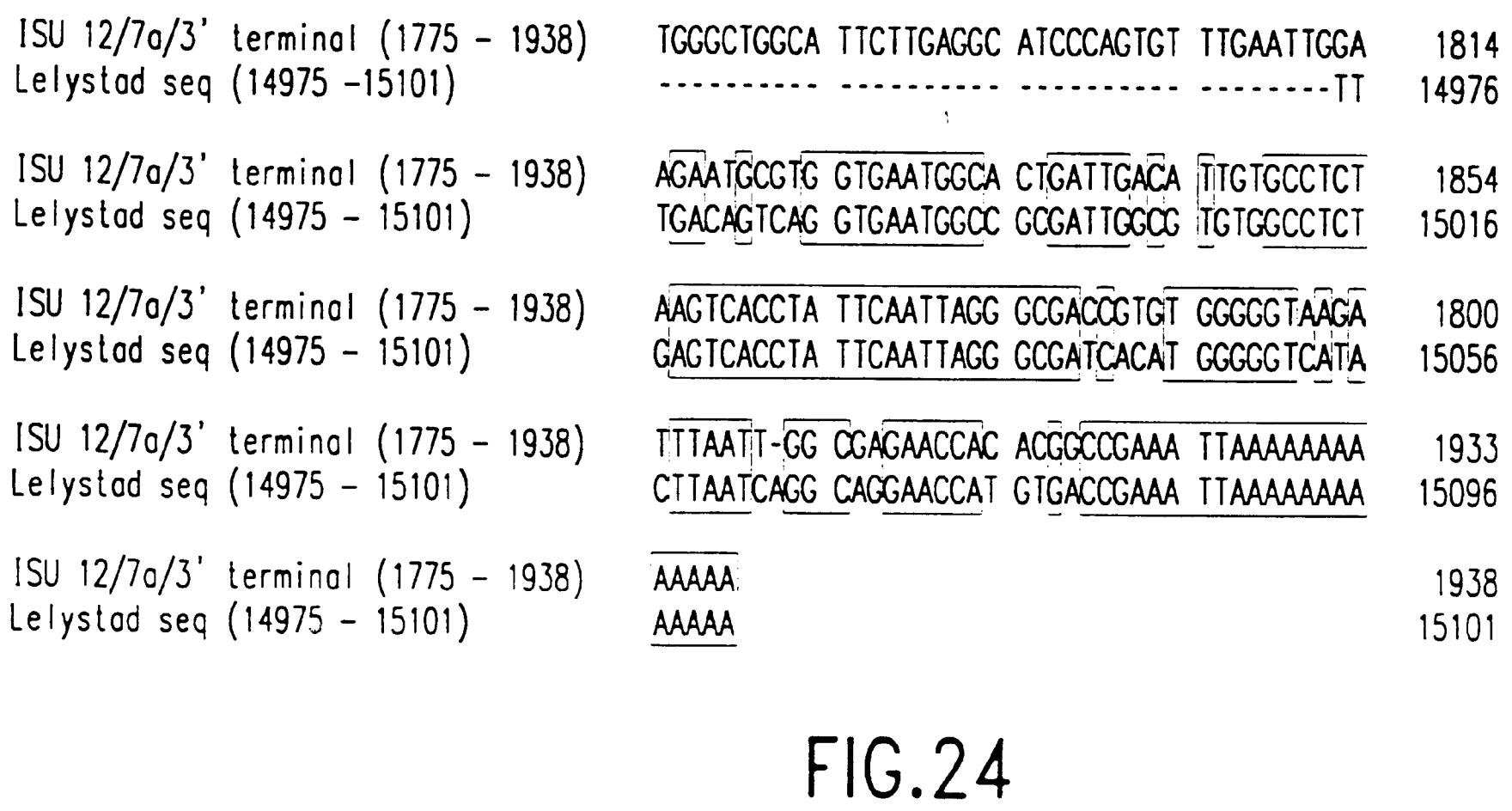

| | | |
|---|---|---|
| ISU 12/7a/3' terminal (1775 - 1938) | TGGCTGGCA TTCTTGAGGC ATCCCAGTGT TTGAATTGGA | 1814 |
| Lelystad seq (14975 -15101) | ---------- ---------- ---------- --------TT | 14976 |
| ISU 12/7a/3' terminal (1775 - 1938) | AGAATGCGTG GTGAATGGCA CTGATTGACA TTGTGCCTCT | 1854 |
| Lelystad seq (14975 - 15101) | TGACAGTCAG GTGAATGGCC GCGATTGGCG TGTGGCCTCT | 15016 |
| ISU 12/7a/3' terminal (1775 - 1938) | AAGTCACCTA TTCAATTAGG GCGACCGTGT GGGGGTAAGA | 1800 |
| Lelystad seq (14975 - 15101) | GAGTCACCTA TTCAATTAGG GCGATCACAT GGGGGTCATA | 15056 |
| ISU 12/7a/3' terminal (1775 - 1938) | TTTAATT-GG CGAGAACCAC ACGGCCGAAA TTAAAAAAAA | 1933 |
| Lelystad seq (14975 - 15101) | CTTAATCAGG CAGGAACCAT GTGACCGAAA TTAAAAAAAA | 15096 |
| ISU 12/7a/3' terminal (1775 - 1938) | AAAAA | 1938 |
| Lelystad seq (14975 - 15101) | AAAAA | 15101 |

FIG.24

SEQUENCE LISTING

```
(1) GENERAL INFORMATION:

   (iii) NUMBER OF SEQUENCES: 47


(2) INFORMATION FOR SEQ ID NO:1:

     (i) SEQUENCE CHARACTERISTICS:
          (A) LENGTH: 22 base pairs
          (B) TYPE: nucleic acid
          (C) STRANDEDNESS: single
          (D) TOPOLOGY: unknown

    (ii) MOLECULE TYPE: cDNA

    (vi) ORIGINAL SOURCE:
          (A) ORGANISM: Porcine reproductive and respiratory syndrome
               virus
          (B) STRAIN: Iowa
          (C) INDIVIDUAL ISOLATE: ISU-12

    (xi) SEQUENCE DESCRIPTION: SEQ ID NO:1:

CGGCCGTGTG GTTCTCGCCA AT                                            22


(2) INFORMATION FOR SEQ ID NO:2:

     (i) SEQUENCE CHARACTERISTICS:
          (A) LENGTH: 22 base pairs
          (B) TYPE: nucleic acid
          (C) STRANDEDNESS: single
          (D) TOPOLOGY: unknown

    (ii) MOLECULE TYPE: cDNA

    (vi) ORIGINAL SOURCE:
```

-continued (A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:2:

CCCCATTTCC CTCTAGCGAC TG 22

(2) INFORMATION FOR SEQ ID NO:3:

(i) SEQUENCE CHARACTERISTICS:
(A) LENGTH: 20 base pairs
(B) TYPE: nucleic acid
(C) STRANDEDNESS: single
(D) TOPOLOGY: unknown (ii) MOLECULE TYPE: cDNA (vi) ORIGINAL SOURCE:
(A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:3:

GCCGCGGAAC CATCAAGCAC 20

(2) INFORMATION FOR SEQ ID NO:4:

(i) SEQUENCE CHARACTERISTICS:
(A) LENGTH: 20 base pairs
(B) TYPE: nucleic acid
(C) STRANDEDNESS: single
(D) TOPOLOGY: unknown (ii) MOLECULE TYPE: cDNA (vi) ORIGINAL SOURCE:
(A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:4:

CAACTTGACG CTATGTGAGC 20

(2) INFORMATION FOR SEQ ID NO:5:

(i) SEQUENCE CHARACTERISTICS:
(A) LENGTH: 20 base pairs
(B) TYPE: nucleic acid
(C) STRANDEDNESS: single
(D) TOPOLOGY: unknown (ii) MOLECULE TYPE: cDNA (vi) ORIGINAL SOURCE:
(A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:5:

GCGGTCTGGA TTGACGACAG 20

(2) INFORMATION FOR SEQ ID NO:6:

(i) SEQUENCE CHARACTERISTICS:
(A) LENGTH: 20 base pairs
(B) TYPE: nucleic acid
(C) STRANDEDNESS: single (D) TOPOLOGY: unknown (ii) MOLECULE TYPE: cDNA (vi) ORIGINAL SOURCE:
(A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:6:

```
GACTGCTAGG GCTTCTGCAC                                    20
```

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: unknown (ii) MOLECULE TYPE: cDNA (vi) ORIGINAL SOURCE:
(A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:7:

```
GCCATTCAGC TCACATAGCG                                    20
```

(2) INFORMATION FOR SEQ ID NO:8:

(i) SEQUENCE CHARACTERISTICS:
(A) LENGTH: 1938 base pairs
(B) TYPE: nucleic acid
(C) STRANDEDNESS: double
(D) TOPOLOGY: unknown (ii) MOLECULE TYPE: cDNA (vi) ORIGINAL SOURCE:
(A) ORGANISM: Porcine reproductive and respiratory syndrome virus
(B) STRAIN: Iowa
(C) INDIVIDUAL ISOLATE: ISU-12

(ix) FEATURE:
(A) NAME/KEY: CDS
(B) LOCATION: 1..1938

(xi) SEQUENCE DESCRIPTION: SEQ ID NO:8:

```
GGC ACG AGC TTT GCT GTC CTC CAA GAC ATC AGT TGC CTT AGG CAT CGC       48
Gly Thr Ser Phe Ala Val Leu Gln Asp Ile Ser Cys Leu Arg His Arg
  1               5                  10                  15

AAC TCG GCC TCT GAG GCG ATT CGC AAA GTC CCT CAG TGC CGC ACG GCG       96
Asn Ser Ala Ser Glu Ala Ile Arg Lys Val Pro Gln Cys Arg Thr Ala
             20                  25                  30

ATA GGG ACA CCC GTG TAT ATC ACT GTC ACA GCC AAT GTT ACC GAT GAG      144
Ile Gly Thr Pro Val Tyr Ile Thr Val Thr Ala Asn Val Thr Asp Glu
         35                  40                  45

AAT TAT TTG CAT TCC TCT GAT CTT CTC ATG CTT TCT TCT TGC CTT TTC      192
Asn Tyr Leu His Ser Ser Asp Leu Leu Met Leu Ser Ser Cys Leu Phe
     50                  55                  60

TAT GCT TCT GAG ATG AGT GAA AAG GGA TTT AAG GTG GTA TTT GGC AAT      240
Tyr Ala Ser Glu Met Ser Glu Lys Gly Phe Lys Val Val Phe Gly Asn
 65                  70                  75                  80

GTG TCA GGC ATC TTT TAG CCT GTC TTT TTG CGA TTC TGT TGG CAA TTT      288
```

-continued

```
Val Ser Gly Ile Phe  *  Pro Val Phe Leu Arg Phe Cys Trp Gln Phe
                85                  90                  95

GAA TGT TTT AAG TAT GTT GGG GAA ATG CTT GAC CGC GGG CTG TTG CTC      336
Glu Cys Phe Lys Tyr Val Gly Glu Met Leu Asp Arg Gly Leu Leu Leu
            100                 105                 110

GCA ATT GCT TTT TTT GTG GTG TAT CGT GCC GTC TTG TTT TGT TGC GCT      384
Ala Ile Ala Phe Phe Val Val Tyr Arg Ala Val Leu Phe Cys Cys Ala
        115                 120                 125

CGT CAG CGC CAA CGG GAA CAG CGG CTC AAA TTT ACA GCT GAT TTA CAA      432
Arg Gln Arg Gln Arg Glu Gln Arg Leu Lys Phe Thr Ala Asp Leu Gln
    130                 135                 140

CTT GAC GCT ATG TGA GCT GAA TGG CAC AGA TTG GCT AGC TAA TAA ATT      480
Leu Asp Ala Met  *  Ala Glu Trp His Arg Leu Ala Ser  *   *  Ile
145                 150                 155                 160

TGA CTG GGC AGT GGA GTG TTT TGT CAT TTT TCC TGT GTT GAC TCA CAT      528
 *  Leu Gly Ser Gly Val Phe Cys His Phe Ser Cys Val Asp Ser His
                165                 170                 175

TGT CTC TTA TGG TGC CCT CAC TAC TAG CCA TTT CCT TGA CAC AGT CGG      576
Cys Leu Leu Trp Cys Pro His Tyr  *  Pro Phe Pro  *  His Ser Arg
            180                 185                 190

TCT GGT CAC TGT GTC TAC CGC TGG GTT TGT TCA CGG GCG GTA TGT TCT      624
Ser Gly His Cys Val Tyr Arg Trp Val Cys Ser Arg Ala Val Cys Ser
        195                 200                 205

GAG TAG CAT GTA CGC GGT CTG TGC CCT GGC TGC GTT GAT TTG CTT CGT      672
Glu  *  His Val Arg Gly Leu Cys Pro Gly Cys Val Asp Leu Leu Arg
    210                 215                 220

CAT TAG GCT TGC GAA GAA TTG CAT GTC CTG GCG CTA CTC ATG TAC CAG      720
His  *  Ala Cys Glu Glu Leu His Val Leu Ala Leu Leu Met Tyr Gln
225                 230                 235                 240

ATA TAC CAA CTT TCT TCT GGA CAC TAA GGG CAG ACT CTA TCG TTG GCG      768
Ile Tyr Gln Leu Ser Ser Gly His  *  Gly Gln Thr Leu Ser Leu Ala
                245                 250                 255

GTC GCC TGT CAT CAT AGA GAA AAG GGG CAA AGT TGA GGT CGA AGG TCA      816
Val Ala Cys His His Arg Glu Lys Gly Gln Ser  *  Gly Arg Arg Ser
            260                 265                 270

CCT GAT CGA CCT CAA AAG AGT TGT GCT TGA TGG TTC CGC GGC TAC CCC      864
Pro Asp Arg Pro Gln Lys Ser Cys Ala  *  Trp Phe Arg Gly Tyr Pro
        275                 280                 285

TGT AAC CAG AGT TTC AGC GGA ACA ATG GAG TCG TCC TTA GAT GAC TTC      912
Cys Asn Gln Ser Phe Ser Gly Thr Met Glu Ser Ser Leu Asp Asp Phe
    290                 295                 300

TGT CAT GAT AGC ACG GCT CCA CAA AAG GTG CTC TTG GCG TTT TCT ATT      960
Cys His Asp Ser Thr Ala Pro Gln Lys Val Leu Leu Ala Phe Ser Ile
305                 310                 315                 320

ACC TAC ACG CCA GTG ATG ATA TAT GCC CTA AAG GTG AGT CGC GGC CGA     1008
Thr Tyr Thr Pro Val Met Ile Tyr Ala Leu Lys Val Ser Arg Gly Arg
                325                 330                 335

CTG CTA GGG CTT CTG CAC CTT TTG GTC TTC CTG AAT TGT GCT TTC ACC     1056
Leu Leu Gly Leu Leu His Leu Leu Val Phe Leu Asn Cys Ala Phe Thr
            340                 345                 350

TTC GGG TAC ATG ACA TTC GTG CAC TTT CAG AGT ACA AAT AAG GTC GCG     1104
Phe Gly Tyr Met Thr Phe Val His Phe Gln Ser Thr Asn Lys Val Ala
        355                 360                 365

CTC ACT ATG GGA GCA GTA GTT GCA CTC CTT TGG GGG GTG TAC TCA GCC     1152
Leu Thr Met Gly Ala Val Val Ala Leu Leu Trp Gly Val Tyr Ser Ala
    370                 375                 380

ATA GAA ACC TGG AAA TTC ATC ACC TCC AGA TGC CGT TTG TGC TTG CTA     1200
Ile Glu Thr Trp Lys Phe Ile Thr Ser Arg Cys Arg Leu Cys Leu Leu
385                 390                 395                 400
```

-continued

```
GGC CGC AAG TAC ATT CTG GCC CCT GCC CAC CAC GTT GAA AGT GCC GCA      1248
Gly Arg Lys Tyr Ile Leu Ala Pro Ala His His Val Glu Ser Ala Ala
                405                 410                 415

GGC TTT CAT CCG ATT GCG GCA AAT GAT AAC CAC GCA TTT GTC GTC CGG      1296
Gly Phe His Pro Ile Ala Ala Asn Asp Asn His Ala Phe Val Val Arg
            420                 425                 430

CGT CCC GGC TCC ACT ACG GTC AAC GGC ACA TTG GTG CCC GGG TTA AAA      1344
Arg Pro Gly Ser Thr Thr Val Asn Gly Thr Leu Val Pro Gly Leu Lys
        435                 440                 445

AGC CTC GTG TTG GGT GGC AGA AAA GCT GTT AAA CAG GGA GTG GTA AAC      1392
Ser Leu Val Leu Gly Gly Arg Lys Ala Val Lys Gln Gly Val Val Asn
    450                 455                 460

CTT GTT AAA TAT GCC AAA TAA CAC CGG CAA GCA GCA GAA GAG AAA GAA      1440
Leu Val Lys Tyr Ala Lys  *  His Arg Gln Ala Ala Glu Glu Lys Glu
465                 470                 475                 480

GGG GGA TGG CCA GCC AGT CAA TCA GCT GTG CCA GAT GCT GGG TAA GAT      1488
Gly Gly Trp Pro Ala Ser Gln Ser Ala Val Pro Asp Ala Gly  *  Asp
                485                 490                 495

CAT CGC TCA CCA AAA CCA GTC CAG AGG CAA GGG ACC GGG AAA GAA AAA      1536
His Arg Ser Pro Lys Pro Val Gln Arg Gln Gly Thr Gly Lys Glu Lys
            500                 505                 510

TAA GAA GAA AAA CCC GGA GAA GCC CCA TTT CCC TCT AGC GAC TGA AGA      1584
 *  Glu Glu Lys Pro Gly Glu Ala Pro Phe Pro Ser Ser Asp  *  Arg
        515                 520                 525

TGA TGT CAG ACA TCA CTT TAC CCC TAG TGA GCG TCA ATT GTG TCT GTC      1632
 *  Cys Gln Thr Ser Leu Tyr Pro  *   *  Ala Ser Ile Val Ser Val

    530                 535                 540

GTC AAT CCA GAC CGC CTT TAA TCA AGG CGC TGG GAC TTG CAC CCT GTC      1680
Val Asn Pro Asp Arg Leu  *  Ser Arg Arg Trp Asp Leu His Pro Val
545                 550                 555                 560

AGA TTC AGG GAG GAT AAG TTA CAC TGT GGA GTT TAG TTT GCC TAC GCA      1728
Arg Phe Arg Glu Asp Lys Leu His Cys Gly Val  *  Phe Ala Tyr Ala
                565                 570                 575

TCA TAC TGT GCG CCT GAT CCG CGT CAC AGC ATC ACC CTC AGC ATG ATG      1776
Ser Tyr Cys Ala Pro Asp Pro Arg His Ser Ile Thr Leu Ser Met Met
            580                 585                 590

GGC TGG CAT TCT TGA GGC ATC CCA GTG TTT GAA TTG GAA GAA TGC GTG      1824
Gly Trp His Ser  *  Gly Ile Pro Val Phe Glu Leu Glu Glu Cys Val
        595                 600                 605

GTG AAT GGC ACT GAT TGA CAT TGT GCC TCT AAG TCA CCT ATT CAA TTA      1872
Val Asn Gly Thr Asp  *  His Cys Ala Ser Lys Ser Pro Ile Gln Leu
    610                 615                 620

GGG CGA CCG TGT GGG GGT AAG ATT TAA TTG GCG AGA ACC ACA CGG CCG      1920
Gly Arg Pro Cys Gly Gly Lys Ile  *  Leu Ala Arg Thr Thr Arg Pro
625                 630                 635                 640

AAA TTA AAA AAA AAA AAA                                              1938
Lys Leu Lys Lys Lys Lys
                645
```

(2) INFORMATION FOR SEQ ID NO:9:

(i) SEQUENCE CHARACTERISTICS:
(A) LENGTH: 85 amino acids
(B) TYPE: amino acid
(D) TOPOLOGY: linear (ii) MOLECULE TYPE: protein (xi) SEQUENCE DESCRIPTION: SEQ ID NO:9:

```
Gly Thr Ser Phe Ala Val Leu Gln Asp Ile Ser Cys Leu Arg His Arg
  1               5                  10                  15
```

-continued

```
Asn Ser Ala Ser Glu Ala Ile Arg Lys Val Pro Gln Cys Arg Thr Ala
            20                  25                  30

Ile Gly Thr Pro Val Tyr Ile Thr Val Thr Ala Asn Val Thr Asp Glu
        35                  40                  45

Asn Tyr Leu His Ser Ser Asp Leu Leu Met Leu Ser Ser Cys Leu Phe
    50                  55                  60

Tyr Ala Ser Glu Met Ser Glu Lys Gly Phe Lys Val Val Phe Gly Asn
 65                  70                  75                  80

Val Ser Gly Ile Phe
                 85
```

(2) INFORMATION FOR SEQ ID NO:10:

(i) SEQUENCE CHARACTERISTICS:
(A) LENGTH: 667 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:10:

```
AATGTGTCAG GCATCTTTTA GCCTGTCTTT TTGCGATTCT GTTGGCAATT TGAATGTTTT     60

AAGTATGTTG GGGAAATGCT TGACCGCGGG CTGTTGCTCG CAATTGCTTT TTTTGTGGTG    120

TATCGTGCCG TCTTGTTTTG TTGCGCTCGT CAGCGCCAAC GGGAACAGCG GCTCAAATTT    180

ACAGCTGATT TACAACTTGA CGCTATGTGA GCTGAATGGC ACAGATTGGC TAGCTAATAA    240

ATTTGACTGG GCAGTGGAGT GTTTTGTCAT TTTTCCTGTG TTGACTCACA TTGTCTCTTA    300

TGGTGCCCTC ACTACTAGCC ATTTCCTTGA CACAGTCGGT CTGGTCACTG TGTCTACCGC    360

TGGGTTTGTT CACGGGCGGT ATGTTCTGAG TAGCATGTAC GCGGTCTGTG CCCTGGCTGC    420

GTTGATTTGC TTCGTCATTA GGCTTGCGAA GAATTGCATG TCCTGGCGCT ACTCATGTAC    480

CAGATATACC AACTTTCTTC TGGACACTAA GGGCAGACTC TATCGTTGGC GGTCGCCTGT    540

CATCATAGAG AAAAGGGGCA AAGTTGAGGT CGAAGGTCAC CTGATCGACC TCAAAAGAGT    600

TGTGCTTGAT GGTTCCGCGG CTACCCCTGT AACCAGAGTT TCAGCGGAAC AATGGAGTCG    660

TCCTTAG                                                              667
```

(2) INFORMATION FOR SEQ ID NO:11:

(i) SEQUENCE CHARACTERISTICS:
(A) LENGTH: 606 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: Porcine reproductive and respiratory syndrome virus
(B) STRAIN: Iowa
(C) INDIVIDUAL ISOLATE: Lelystad (xi) SEQUENCE DESCRIPTION: SEQ ID NO:11:

```
ATGAGATGTT CTCACAAATT GGGGCGTTTC TTGACTCCGC ACTCTTGCTT CTGGTGGCTT     60
```

-continued

```
TTTTTGCTGT GTACCGGCTT GTCCTGGTCC TTTGCCGATG GCAACGGCGA CAGCTCGACA    120

TACCAATACA TATATAACTT GACGATATGC GAGCTGAATG GGACCGACTG GTTGTCCAGC    180

CATTTTGGTT GGGCAGTCGA GACCTTTGTG CTTTACCCGG TTGCCACTCA TATCCTCTCA    240

CTGGGTTTTC TCACAACAAG CCATTTTTTT GACGCGCTCG GTCTCGGCGC TGTATCCACT    300

GCAGGATTTG TTGGCGGGCG GTACGTACTC TGCAGCGTCT ACGGCGCTTG TGCTTTCGCA    360

GCGTTCGTAT GTTTTGTCAT CCGTGCTGCT AAAAATTGCA TGGCCTGCCG CTATGCCCGT    420

ACCCGGTTTA CCAACTTCAT TGTGGACGAC CGGGGGAGAG TTCATCGATG GAAGTCTCCA    480

ATAGTGGTAG AAAAATTGGG CAAAGCCGAA GTCGATGGCA ACCTCGTCAC CATCAAACAT    540

GTCGTCCTCG AAGGGGTTAA AGCTCAACCC TTGACGAGGA CTTCGGCTGA GCAATGGGAG    600

GCCTAG                                                               606
```

(2) INFORMATION FOR SEQ ID NO:12:

(i) SEQUENCE CHARACTERISTICS:
(A) LENGTH: 526 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:12:

```
AATGGAGTCG TCCTTAGATG ACTTCTGTCA TGATAGCACG GCTCCACAAA AGGTGCTCTT     60

GGCGTTTTCT ATTACCTACA CGCCAGTGAT GATATATGCC CTAAAGGTGA GTCGCGGCCG    120

ACTGCTAGGG CTTCTGCACC TTTTGGTCTT CCTGAATTGT GCTTTCACCT TCGGGTACAT    180

GACATTCGTG CACTTTCAGA GTACAAATAA GGTCGCGCTC ACTATGGGAG CAGTAGTTGC    240

ACTCCTTTGG GGGGTGTACT CAGCCATAGA AACCTGGAAA TTCATCACCT CCAGATGCCG    300

TTTGTGCTTG CTAGGCCGCA AGTACATTCT GGCCCCTGCC CACCACGTTG AAAGTGCCGC    360

AGGCTTTCAT CCGATTGCGG CAAATGATAA CCACGCATTT GTCGTCCGGC GTCCCGGCTC    420

CACTACGGTC AACGGCACAT TGGTGCCCGG GTTAAAAAGC CTCGTGTTGG GTGGCAGAAA    480

AGCTGTTAAA CAGGGAGTGG TAAACCTTGT TAAATATGCC AAATAA                   526
```

(2) INFORMATION FOR SEQ ID NO:13:

(i) SEQUENCE CHARACTERISTICS:
(A) LENGTH: 522 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: Porcine reproductive and respiratory syndrome virus
(B) STRAIN: Iowa
(C) INDIVIDUAL ISOLATE: Lelystad (xi) SEQUENCE DESCRIPTION: SEQ ID NO:13:

```
ATGGGAGGCC TAGACGATTT TTGCAACGAT CCTATCGCCG CACAAAAGCT CGTGCTAGCC     60
```

-continued

```
TTTAGCATCA CATACACACC TATAATGATA TACGCCCTTA AGGTGTCACG CGGCCGACTC    120

CTGGGGCTGT TGCACATCCT AATATTTCTG AACTGTTCCT TTACATTCGG ATACATGACA    180

TATGTGCATT TTCAATCCAC CAACCGTGTC GCACTTACCC TGGGGGCTGT TGTCGCCCTT    240

CTGTGGGGTG TTTACAGCTT CACAGAGTCA TGGAAGTTTA TCACTTCCAG ATGCAGATTG    300

TGTTGCCTTG GCCGGCGATA CATTCTGGCC CCTGCCCATC ACGTAGAAAG TGCTGCAGGT    360

CTCCATTCAA TCTCAGCGTC TGGTAACCGA GCATACGCTG TGAGAAAGCC CGGACTAACA    420

TCAGTGAACG GCACTCTAGT ACCAGGACTT CGGAGCCTCG TGCTGGGCGG CAAACGAGCT    480

GTTAAACGAG GAGTGGTTAA CCTCGTCAAG TATGGCCGGT AA                       522
```

(2) INFORMATION FOR SEQ ID NO:14:

(i) SEQUENCE CHARACTERISTICS:
(A) LENGTH: 372 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:14:

```
ATGCCAAATA ACACCGGCAA GCAGCAGAAG AGAAAGAAGG GGGATGGCCA GCCAGTCAAT     60

CAGCTGTGCC AGATGCTGGG TAAGATCATC GCTCACCAAA ACCAGTCCAG AGGCAAGGGA    120

CCGGGAAAGA AAAATAAGAA GAAAAACCCG GAGAAGCCCC ATTTCCCTCT AGCGACTGAA    180

GATGATGTCA GACATCACTT TACCCCTAGT GAGCGTCAAT TGTGTCTGTC GTCAATCCAG    240

ACCGCCTTTA ATCAAGGCGC TGGGACTTGC ACCCTGTCAG ATTCAGGGAG GATAAGTTAC    300

ACTGTGGAGT TTAGTTTGCC TACGCATCAT ACTGTGCGCC TGATCCGCGT CACAGCATCA    360

CCCTCAGCAT GA                                                        372
```

(2) INFORMATION FOR SEQ ID NO:15:

(i) SEQUENCE CHARACTERISTICS:
(A) LENGTH: 387 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: Porcine reproductive and respiratory syndrome virus
(B) STRAIN: Iowa
(C) INDIVIDUAL ISOLATE: Lelystad (xi) SEQUENCE DESCRIPTION: SEQ ID NO:15:

```
ATGGCCGGTA AAAACCAGAG CCAGAAGAAA AAGAAAAGTA CAGCTCCGAT GGGGAATGGC     60

CAGCCAGTCA ATCAACTGTG CCAGTTGCTG GGTGCAATGA TAAAGTCCCA GCGCCAGCAA    120

CCTAGGGGAG GACAGGCCAA AAAGAAAAAG CCTGAGAAGC CACATTTTCC CCTGGCTGCT    180

GAAGATGACA TCCGGCACCA CCTCACCCAG ACTGAACGCT CCCTCTGCTT GCAATCGATC    240

CAGACGGCTT TCAATCAAGG CGCAGGAACT GCGTCGCTTT CATCCAGCGG GAAGGTCAGT    300

TTTCAGGTTG AGTTTATGCT GCCGGTTGCT CATACAGTGC GCCTGATTCG CGTGACTTCT    360
```

-continued

ACATCCGCCA GTCAGGGTGC AAGTTAA 387

(2) INFORMATION FOR SEQ ID NO:16:

(i) SEQUENCE CHARACTERISTICS:
(A) LENGTH: 164 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:16:

TGGGCTGGCA TTCTTGAGGC ATCCCAGTGT TTGAATTGGA AGAATGCGTG GTGAATGGCA 60

CTGATTGACA TTGTGCCTCT AAGTCACCTA TTCAATTAGG GCGACCGTGT GGGGGTAAGA 120

TTTAATTGGC GAGAACCACA CGGCCGAAAT TAAAAAAAAA AAAA 164

(2) INFORMATION FOR SEQ ID NO:17:

(i) SEQUENCE CHARACTERISTICS:
(A) LENGTH: 127 base pairs
(B) TYPE: nucleic acid
(C) STRANDEDNESS: single
(D) TOPOLOGY: unknown (ii) MOLECULE TYPE: cDNA (vi) ORIGINAL SOURCE:
(A) ORGANISM: Porcine reproductive and respiratory syndrome virus
(B) STRAIN: Iowa
(C) INDIVIDUAL ISOLATE: Lelystad (xi) SEQUENCE DESCRIPTION: SEQ ID NO:17:

TTTGACAGTC AGGTGAATGG CCGCGATTGG CGTGTGGCCT CTGAGTCACC TATTCAATTA 60

GGGCGATCAC ATGGGGGTCA TACTTAATCA GGCAGGAACC ATGTGACCGA AATTAAAAAA 120

AAAAAAA 127

(2) INFORMATION FOR SEQ ID NO:18:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA (synthetic)"

(vi) ORIGINAL SOURCE:
(A) ORGANISM: Porcine reproductive and respiratory syndrome virus
(B) STRAIN: Lelystad (xi) SEQUENCE DESCRIPTION: SEQ ID NO:18:

CTCGTCAAGT ATGGCCGGT 19

(2) INFORMATION FOR SEQ ID NO:19:

(i) SEQUENCE CHARACTERISTICS:
(A) LENGTH: 19 base pairs

-continued (B) TYPE: nucleic acid
(C) STRANDEDNESS: single
(D) TOPOLOGY: linear (ii) MOLECULE TYPE: other nucleic acid
(A) DESCRIPTION: /desc = "DNA (synthetic)"

(vi) ORIGINAL SOURCE:
(A) ORGANISM: Porcine reproductive and respiratory syndrome virus (xi) SEQUENCE DESCRIPTION: SEQ ID NO:19:

GCCATTCGCC TGACTGTCA 19

(2) INFORMATION FOR SEQ ID NO:20:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA (synthetic)"

(vi) ORIGINAL SOURCE:
(A) ORGANISM: Porcine reproductive and respiratory syndrome virus (xi) SEQUENCE DESCRIPTION: SEQ ID NO:20:

TTGACGAGGA CTTCGGCTG 19

(2) INFORMATION FOR SEQ ID NO:21:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA (synthetic)"

(vi) ORIGINAL SOURCE:
(A) ORGANISM: Porcine reproductive and respiratory syndrome virus (xi) SEQUENCE DESCRIPTION: SEQ ID NO:21:

GCTCTACCTG CAATTCTGTG 20

(2) INFORMATION FOR SEQ ID NO:22:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA (synthetic)"

(vi) ORIGINAL SOURCE:
(A) ORGANISM: Porcine reproductive and respiratory syndrome virus (xi) SEQUENCE DESCRIPTION: SEQ ID NO:22:

GTGTATAGGA CCGGCAACAG 20

(2) INFORMATION FOR SEQ ID NO:23:

(i) SEQUENCE CHARACTERISTICS:

-continued (A) LENGTH: 26 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA (synthetic)"

(vi) ORIGINAL SOURCE:
(A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:23:

GGGGATCCGG TATTTGGCAA TGTGTC 26

(2) INFORMATION FOR SEQ ID NO:24:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA (synthetic)"

(vi) ORIGINAL SOURCE:
(A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:24:

GGTGTTTTCC ACGAGAACCG CTTAAGGG 28

(2) INFORMATION FOR SEQ ID NO:25:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA (synthetic)"

(vi) ORIGINAL SOURCE:
(A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:25:

GGGGATCCAG AGTTTCAGCG G 21

(2) INFORMATION FOR SEQ ID NO:26:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA (synthetic)"

(vi) ORIGINAL SOURCE:
(A) ORGANISM: Porcine reproductive and respiratory syndrome virus
(B) STRAIN: Iowa
(C) INDIVIDUAL ISOLATE: ISU-12

-continued (xi) SEQUENCE DESCRIPTION: SEQ ID NO:26:

CAGTTAGTCG ACACGGTCTT AAGGG 25

(2) INFORMATION FOR SEQ ID NO:27:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA (synthetic)"

(vi) ORIGINAL SOURCE:
(A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:27:

GGGGATCCTT GTTAAATATG CC 22

(2) INFORMATION FOR SEQ ID NO:28:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "DNA (synthetic)"

(vi) ORIGINAL SOURCE:
(A) ORGANISM: Porcine reproductive and respiratory syndrome virus
(B) STRAIN: Iowa
(C) INDIVIDUAL ISOLATE: ISU-12

(xi) SEQUENCE DESCRIPTION: SEQ ID NO:28:

CTTACGCACC ACTTAAGGG 19

(2) INFORMATION FOR SEQ ID NO:29:

(i) SEQUENCE CHARACTERISTICS:
(A) LENGTH: 62 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:29:

```
Pro Val Phe Leu Arg Phe Cys Trp Gln Phe Glu Cys Phe Lys Tyr Val
1               5                   10                  15

Gly Glu Met Leu Asp Arg Gly Leu Leu Leu Ala Ile Ala Phe Phe Val
            20                  25                  30

Val Tyr Arg Ala Val Leu Phe Cys Cys Ala Arg Gln Arg Gln Arg Glu
        35                  40                  45

Gln Arg Leu Lys Phe Thr Ala Asp Leu Gln Leu Asp Ala Met
    50                  55                  60
```

(2) INFORMATION FOR SEQ ID NO:30:

(i) SEQUENCE CHARACTERISTICS:
(A) LENGTH: 8 amino acids

-continued (B) TYPE: amino acid
(C) STRANDEDNESS: single
(D) TOPOLOGY: linear (ii) MOLECULE TYPE: peptide (xi) SEQUENCE DESCRIPTION: SEQ ID NO:30:

Ala Glu Trp His Arg Leu Ala Ser
1 5

(2) INFORMATION FOR SEQ ID NO:31:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:31:

Leu Gly Ser Gly Val Phe Cys His Phe Ser Cys Val Asp Ser His Cys
1 5 10 15

Leu Leu Trp Cys Pro His Tyr
20

(2) INFORMATION FOR SEQ ID NO:32:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:32:

His Ser Arg Ser Gly His Cys Val Tyr Arg Trp Val Cys Ser Arg Ala
1 5 10 15

Val Cys Ser Glu
20

(2) INFORMATION FOR SEQ ID NO:33:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:33:

His Val Arg Gly Leu Cys Pro Gly Cys Val Asp Leu Leu Arg His
1 5 10 15

(2) INFORMATION FOR SEQ ID NO:34:

(i) SEQUENCE CHARACTERISTICS:
(A) LENGTH: 22 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:34:

Ala Cys Glu Glu Leu His Val Leu Ala Leu Leu Met Tyr Gln Ile Tyr

-continued

```
1               5                   10                  15

Gln Leu Ser Ser Gly His
            20


(2) INFORMATION FOR SEQ ID NO:35:

     (i) SEQUENCE CHARACTERISTICS:
          (A) LENGTH: 18 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:35:

Gly Gln Thr Leu Ser Leu Ala Val Ala Cys His His Arg Glu Lys Gly
1               5                   10                  15

Gln Ser


(2) INFORMATION FOR SEQ ID NO:36:

     (i) SEQUENCE CHARACTERISTICS:
          (A) LENGTH: 13 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:36:

Gly Arg Arg Ser Pro Asp Arg Pro Gln Lys Ser Cys Ala
1               5                   10


(2) INFORMATION FOR SEQ ID NO:37:

     (i) SEQUENCE CHARACTERISTICS:
          (A) LENGTH: 188 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:37:

Trp Phe Arg Gly Tyr Pro Cys Asn Gln Ser Phe Ser Gly Thr Met Glu
1               5                   10                  15

Ser Ser Leu Asp Asp Phe Cys His Asp Ser Thr Ala Pro Gln Lys Val
            20                  25                  30

Leu Leu Ala Phe Ser Ile Thr Tyr Thr Pro Val Met Ile Tyr Ala Leu
        35                  40                  45

Lys Val Ser Arg Gly Arg Leu Leu Gly Leu Leu His Leu Leu Val Phe
    50                  55                  60

Leu Asn Cys Ala Phe Thr Phe Gly Tyr Met Thr Phe Val His Phe Gln
65                  70                  75                  80

Ser Thr Asn Lys Val Ala Leu Thr Met Gly Ala Val Val Ala Leu Leu
                85                  90                  95

Trp Gly Val Tyr Ser Ala Ile Glu Thr Trp Lys Phe Ile Thr Ser Arg
            100                 105                 110

Cys Arg Leu Cys Leu Leu Gly Arg Lys Tyr Ile Leu Ala Pro Ala His
        115                 120                 125

His Val Glu Ser Ala Ala Gly Phe His Pro Ile Ala Ala Asn Asp Asn
    130                 135                 140
```

-continued

```
His Ala Phe Val Val Arg Arg Pro Gly Ser Thr Thr Val Asn Gly Thr
145                 150                 155                 160

Leu Val Pro Gly Leu Lys Ser Leu Val Leu Gly Gly Arg Lys Ala Val
                165                 170                 175

Lys Gln Gly Val Val Asn Leu Val Lys Tyr Ala Lys
            180                 185
```

(2) INFORMATION FOR SEQ ID NO:38:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:38:

```
His Arg Gln Ala Ala Glu Glu Lys Glu Gly Gly Trp Pro Ala Ser Gln
1               5                   10                  15

Ser Ala Val Pro Asp Ala Gly
            20
```

(2) INFORMATION FOR SEQ ID NO:39:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:39:

```
Asp His Arg Ser Pro Lys Pro Val Gln Arg Gln Gly Thr Gly Lys Glu
1               5                   10                  15

Lys
```

(2) INFORMATION FOR SEQ ID NO:40:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:40:

```
Glu Glu Lys Pro Gly Glu Ala Pro Phe Pro Ser Ser Asp
1               5                   10
```

(2) INFORMATION FOR SEQ ID NO:41:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:41:

```
Cys Gln Thr Ser Leu Tyr Pro
1               5
```

-continued (2) INFORMATION FOR SEQ ID NO:42:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:42:

```
Ala Ser Ile Val Ser Val Val Asn Pro Asp Arg Leu
1               5                   10
```

(2) INFORMATION FOR SEQ ID NO:43:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:43:

```
Ser Arg Arg Trp Asp Leu His Pro Val Arg Phe Arg Glu Asp Lys Leu
1               5                   10                  15

His Cys Gly Val
            20
```

(2) INFORMATION FOR SEQ ID NO:44:

(i) SEQUENCE CHARACTERISTICS:
(A) LENGTH: 69 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:44:

```
Pro His Glu Ala Leu Ala Thr Tyr Arg Ala Leu Ala Ser Glu Arg Thr
1               5                   10                  15

Tyr Arg Cys Tyr Ser Ala Leu Ala Pro Arg Ala Ser Pro Pro Arg Ala
            20                  25                  30

Arg Gly His Ile Ser Ser Glu Arg Ile Leu Glu Thr His Arg Leu Glu
        35                  40                  45

Ser Glu Arg Met Glu Thr Met Glu Thr Gly Leu Tyr Thr Arg Pro His
    50                  55                  60

Ile Ser Ser Glu Arg
65
```

(2) INFORMATION FOR SEQ ID NO:45:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:45:

```
Gly Ile Pro Val Phe Glu Leu Glu Glu Cys Val Val Asn Gly Thr Asp
1               5                   10                  15
```

-continued

```
(2) INFORMATION FOR SEQ ID NO:46:

     (i) SEQUENCE CHARACTERISTICS:
          (A) LENGTH: 18 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:46:

His Cys Ala Ser Lys Ser Pro Ile Gln Leu Gly Arg Pro Cys Gly Gly
1               5                   10                  15

Lys Ile


(2) INFORMATION FOR SEQ ID NO:47:

     (i) SEQUENCE CHARACTERISTICS:
          (A) LENGTH: 13 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:47:

Leu Ala Arg Thr Thr Arg Pro Lys Leu Lys Lys Lys Lys
1               5                   10
```

METHOD OF PRODUCING A VACCINE WHICH RAISES AN IMMUNOLOGICAL RESPONSE AGAINST A VIRUS CAUSING A PORCINE RESPIRATORY AND REPRODUCTIVE DISEASE

This is a Division, of application Ser. No. 08/131,625 filed on Oct. 5, 1993, now U.S. Pat. No. 5,695,766; which is a continuation-in-part of application Ser. No. 07/969,071 filed on Oct. 30, 1992, now abandoned.

BACKGROUND OF THE INVENTION

1. Field of the Invention

The present invention concerns a vaccine which protects pigs from a disease caused by respiratory and reproductive viruses, a method of protecting a pig from a respiratory and reproductive disease, a method of producing a vaccine, and DNA obtained from a virus causing a porcine respiratory and reproductive disease.

2. Discussion of the Background

In recent years, North American and European swine herds have been susceptible to infection by new strains of respiratory and reproductive viruses (see *A.A.S.P.*, September/October 1991, pp. 7–11; *The Veterinary Record,* Feb. 1, 1992, pp. 87–89; Ibid., Nov. 30, 1991, pp. 495–496; Ibid., Oct. 26, 1991, p. 370; Ibid., Oct. 19, 1991, pp. 367–368; Ibid., Aug. 3, 1991, pp. 102–103; Ibid., Jul. 6, 1991; Ibid., Jun. 22, 1991, p. 578; Ibid., Jun. 15, 1991, p. 574; Ibid., Jun. 8, 1991, p. 536; Ibid., Jun. 1, 1991, p. 511; Ibid., Mar. 2, 1991, p. 213). Among the first of the new strains to be identified was a virus associated with the so-called Mystery Swine Disease (MSD) or "blue-eared syndrome", now known as Swine Infertility and Respiratory Syndrome (SIRS) or Porcine Reproductive and Respiratory Syndrome (PRRS). In Europe, this disease has also been called porcine epidemic abortion and respiratory syndrome (PEARS), blue abortion disease, blue ear disease (U.K.), abortus blau (Netherlands) and seuchenhafter spatabort der schweine (Germany), and the corresponding virus has been termed "Lelystad virus." In the U.S., this disease has also been called Wabash syndrome, mystery pig disease (MPD) and swine plague. A disease which is sometimes associated with PRRS is proliferative interstitial pneumonia (PIP).

Outbreaks of "blue ear disease" have been observed in swine herds in the U.K., Germany, Belgium and the Netherlands. Its outbreak in England has led to cancellation of pig shows. The symptoms of PRRS include a reluctance to eat (anorexia), a mild fever (pyrexia), cyanosis of the extremities (notably bluish ears), stillbirths, abortion, high mortality in affected litters, weak-born piglets and premature farrowing. The majority of piglets born alive to affected sows die within 48 hours. PRRS clinical signs include mild influenza-like signs, rapid respiration ("thumping"), and a diffuse interstitial pneumonitis. PRRS virus has an incubation period of about 2 weeks from contact with an infected animal. The virus appears to be an enveloped RNA arterivirus (Ibid., Feb. 1, 1992). The virus has been grown successfully in pig alveolar macrophages and CL2621 cells (Benfield et al, *J. Vet. Diagn. Invest.,* 4:127–133, 1992; Collins et al, Swine Infertility and Respiratory Syndrome/Mystery Swine Disease. *Proc., Minnesota Swine Conference for Veterinarians,* pp. 200–205, 1991), and in MARC-145 cells (Joo, PRRS: Diagnosis, *Proc., Allen D. Leman Swine Conference,* Veterinary Continuing Education and Extension, University of Minnesota (1993), 20:53–55). A successful culturing of a virus which causes SIRS has also been reported by Wensvoort et al (Mystery Swine Disease in the Netherlands: The Isolation of Lelystad Virus. *Vet. Quart.* 13:121–130, 1991).

The occurrence of PRRS in the U.S. has adversely affected the pig farming industry. In Canada, PRRS has been characterized by anorexia and pyrexia in sows lasting up to 2 weeks, late-term abortions, increased stillbirth rates, weak-born pigs and neonatal deaths preceded by rapid abdominal breathing and diarrhea. Work on the isolation of the virus causing PRRS, on a method of diagnosing PRRS infection, and on the development of a vaccine against the PRRS virus has been published (see Canadian Patent Publication No. 2,076,744; PCT International Patent Publication No. WO 93/03760; PCT International Patent Publication No. WO 93/06211; and PCT International Patent Publication No. WO 93/07898).

A second virus strain discovered in the search for the causative agent of PRRS causes a disease now known as Proliferative and Necrotizing Pneumonia (PNP). The symptoms of PNP and the etiology of the virus which causes it appear similar to PRRS and its corresponding virus, but there are identifiable differences. For example, the virus which causes PNP is believed to be a non-classical or atypical swine influenza A virus (aSIV).

The main clinical signs of PNP are fever, dyspnea and abdominal respiration. Pigs of different ages are affected, but most signs occur in pigs between 4 and 16 weeks of age. Lungs of affected pigs are diffusely reddened and "meaty" in consistency (Collins, *A.A.S.P.*, September/October 1991, pp. 7–11). By contrast, pigs affected with PRRS show no significant fever, and respiratory signs are observed mainly in neonatal pigs (less than 3 weeks old) with pulmonary lesions, characterized by a diffuse interstitial pneumonia.

Encephalomyocarditis virus (EMCV) is another virus which causes severe interstitial pneumonia along with severe interstitial, necrotizing and calcifying myocarditis. Experimentally, EMCV produces reproductive failure in affected sows (Kim et al, *J. Vet. Diagn. Invest.,* 1:101–104 (1989); Links et al, *Aust. Vet. J.,* 63:150–152 (1986); Love et al, *Aust. Vet. J.,* 63:128–129 (1986)).

Recently, a more virulent form of PRRS has been occurring with increased incidence in 3–8 week old pigs in the Midwestern United States. Typically, healthy 3–5 week old pigs are weaned and become sick 5–7 days later. Routine virus identification methods on tissues from affected pigs have shown that swine influenza virus (SIV), pseudorabies virus (PRV), and *Mycoplasma hyophneumoniae* are not associated with this new form of PRRS.

The present invention is primarily concerned with a vaccine which protects pigs from the infectious agent causing this new, more virulent form of PRRS, with a method of producing and administering the vaccine, and with DNA encoding a portion of the genome of the infectious agent causing this new form of PRRS. However, it is believed that the information learned in the course of developing the present invention will be useful in developing vaccines and methods of protecting pigs against any and/or all porcine respiratory and reproductive diseases. For example, the present Inventors have characterized the pathology of at least one PRRS virus which differs from the previously published pathology of PRRS virus(es) (see Table I below). Therefore, the present invention is not necessarily limited to vaccines and methods related to the infectious agent causing this new form of PRRS, which the present Inventors have termed the "Iowa strain" of PRRS virus (PRRSV).

Nonetheless, pessimism and skepticism has been expressed in the art concerning the development of effective vaccines against these porcine viruses (*The Veterinary Record,* Oct. 26, 1991). A belief that human influenza vaccine may afford some protection against the effects of PRRS and PNP exists in the art (for example, see Ibid., Jul. 6, 1991). However, the use of a human vaccine in a food animal is generally discouraged by regulatory and administrative agencies, and therefore, this approach is not feasible in actual practice (Ibid.).

The pig farming industry has been and will continue to be adversely affected by these porcine reproductive and respiratory diseases and new variants thereof, as they appear. Surprisingly, the market for animal vaccines in the U.S. and worldwide is larger than the market for human vaccines. Thus, there exists an economic incentive to develop new veterinary vaccines, in addition to the substantial public health benefit which is derived from protecting farm animals from disease.

SUMMARY OF THE INVENTION

Accordingly, one object of the present invention is to provide a novel vaccine which protects a pig against infection by a virus which causes a porcine respiratory and reproductive disease.

It is a further object of the present invention to provide a vaccine which protects a pig against the Iowa strain of PRRSV.

It is a further object of the present invention to provide a vaccine which raises an effective immunological response against a virus which causes a respiratory and reproductive disease in a pig, particularly against the Iowa strain of PRRSV.

It is a further object of the present invention to provide a novel method of protecting a pig against infection by a virus which causes a porcine respiratory and reproductive disease, particularly against the Iowa strain of PRRSV.

It is a further object of the present invention to provide a novel method of raising an effective immunological response in a pig against a virus which causes a porcine respiratory and reproductive disease, particularly against the Iowa strain of PRRSV.

It is a further object of the present invention to provide an antibody which immunologically binds to a virus which causes a porcine respiratory and reproductive disease, particularly against the Iowa strain of PRRSV.

It is a further object of the present invention to provide an antibody which immunologically binds to a vaccine which protects a pig against infection by a virus which causes a porcine respiratory and reproductive disease.

It is a further object of the present invention to provide an antibody which immunologically binds to a vaccine which protects a pig against infection by the Iowa strain of PRRSV.

It is a further object of the present invention to provide a method of treating a pig suffering from a porcine respiratory and reproductive disease, particularly from a disease caused by the Iowa strain of PRRSV.

It is a further object of the present invention to provide a method of treating a pig exposed to a virus which causes a porcine respiratory and reproductive disease, particularly to the Iowa strain of PRRSV.

It is a further object of the present invention to provide a diagnostic kit for assaying a virus which causes a porcine respiratory and reproductive disease, particularly a disease caused by the Iowa strain of PRRSV.

It is a further object of the present invention to provide a polynucleotide isolated from the genome of a virus or infectious agent causing a porcine respiratory and reproductive disease, particularly from the Iowa strain of PRRSV.

It is a further object of the present invention to provide a polynucleotide encoding one or more proteins of a virus or infectious agent causing a porcine respiratory and reproductive disease, particularly of the Iowa strain of PRRSV.

It is a further object of the present invention to provide a polynucleotide encoding one or more antigenic peptides from a virus or infectious agent causing a porcine respiratory and reproductive disease, particularly from the Iowa strain of PRRSV.

It is a further object of the present invention to provide a novel method of culturing a porcine reproductive and respiratory virus or infectious agent using a suitable cell line.

It is a further object of the present invention to provide a novel method of culturing the Iowa strain of PRRSV using a suitable cell line.

These and other objects which will become apparent during the following description of the preferred embodiments, have been provided by a vaccine which protects a pig against infection by a virus or infectious agent which causes a porcine reproductive and respiratory disease, a composition which raises an effective immunological response to a virus or infectious agent which causes such a porcine disease, a method of protecting a pig from infection against a virus or infectious agent which causes such a porcine disease, and DNA encoding a portion of the genome of a virus or infectious agent causing a respiratory and reproductive disease.

BRIEF DESCRIPTION OF THE FIGURES

FIGS. 12(A)–(C) are a series of photographs showing swine alveolar macrophage (SAM) cultures: uninfected (A) or infected with ISU-12 (B and C; see Experiment II below);

FIGS. 13(A)–(D) are a series of photographs showing PSP-36 cell cultures: uninfected (A), CPE in those infected with ISU-12 four DPI (B), IFA of those infected with ISU-12 five DPI (C; see Experiment II below), and infected with ISU-984 (a second sample of infectious agent isolated from a pig infected with the Iowa strain of PRRSV) five days after infection (D);

FIGS. 14(A)–(D) are a series of photographs showing PSP-36 cell cultures: uninfected (A) or infected with ISU-12 propagated in SAM 2.5 days after infection (B, C and D);

FIGS. 19A–C presents the 1938-bp 3'-terminal sequence of the genome of the infectious agent associated with the Iowa strain of PRRSV;

FIG. 20 shows the deduced amino acid sequence encoded by the DNA sequence of FIG. 19;

FIG. 21 compares the nucleotide sequences of the infectious agent associated with the Iowa strain of PRRSV (ISU-12) and of the Lelystad virus with regard to open reading frame-5 (ORF-5);

FIG. 22 compares the nucleotide sequences of the ORF-6 of the ISU-12 virus with the ORF-6 of the Lelystad virus;

FIG. 23 compares the nucleotide sequences of the ORF-7 of the ISU-12 virus and the ORF-7 of the Lelystad virus;

FIG. 24 compares the 3'-nontranslational nucleotide sequences of the ISU-12 virus and the Lelystad virus;

DETAILED DESCRIPTION OF THE PREFERRED EMBODIMENTS

Figure 1:
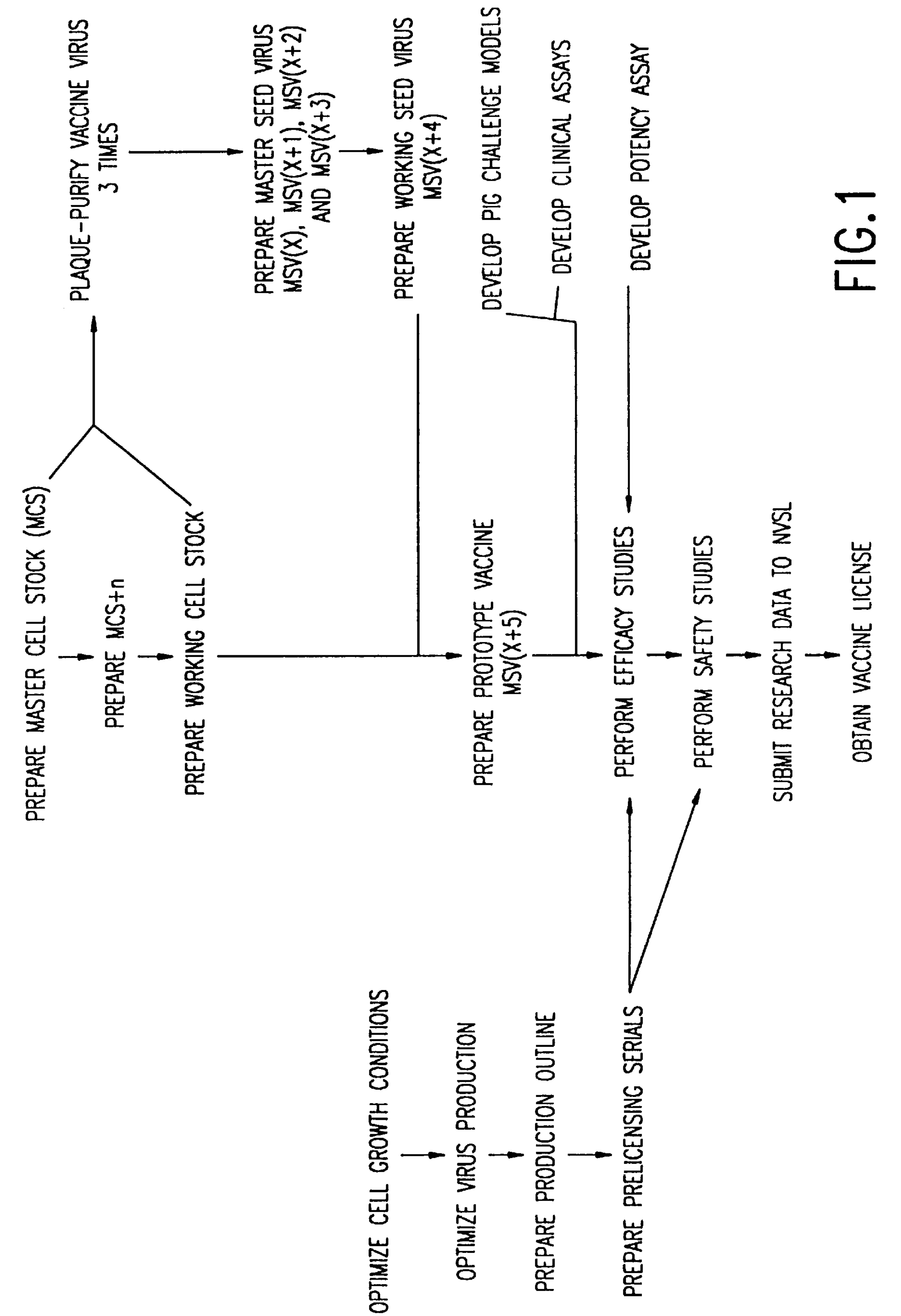
FIG. 1 is a flowchart for the production of a modified live vaccine.
Figure 2:
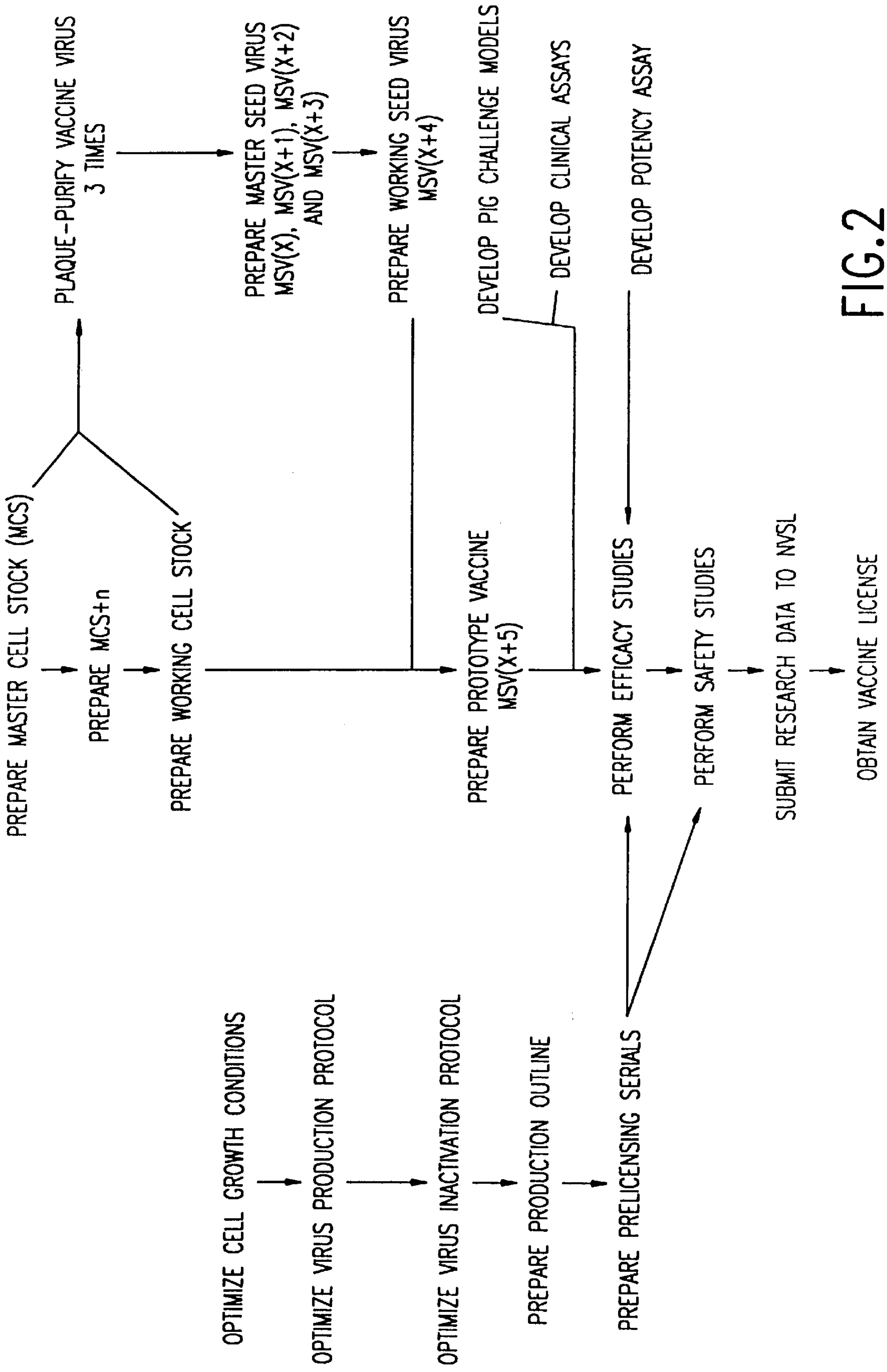
FIG. 2 is a flowchart of a process for producing an inactivated vaccine.
Figure 3:
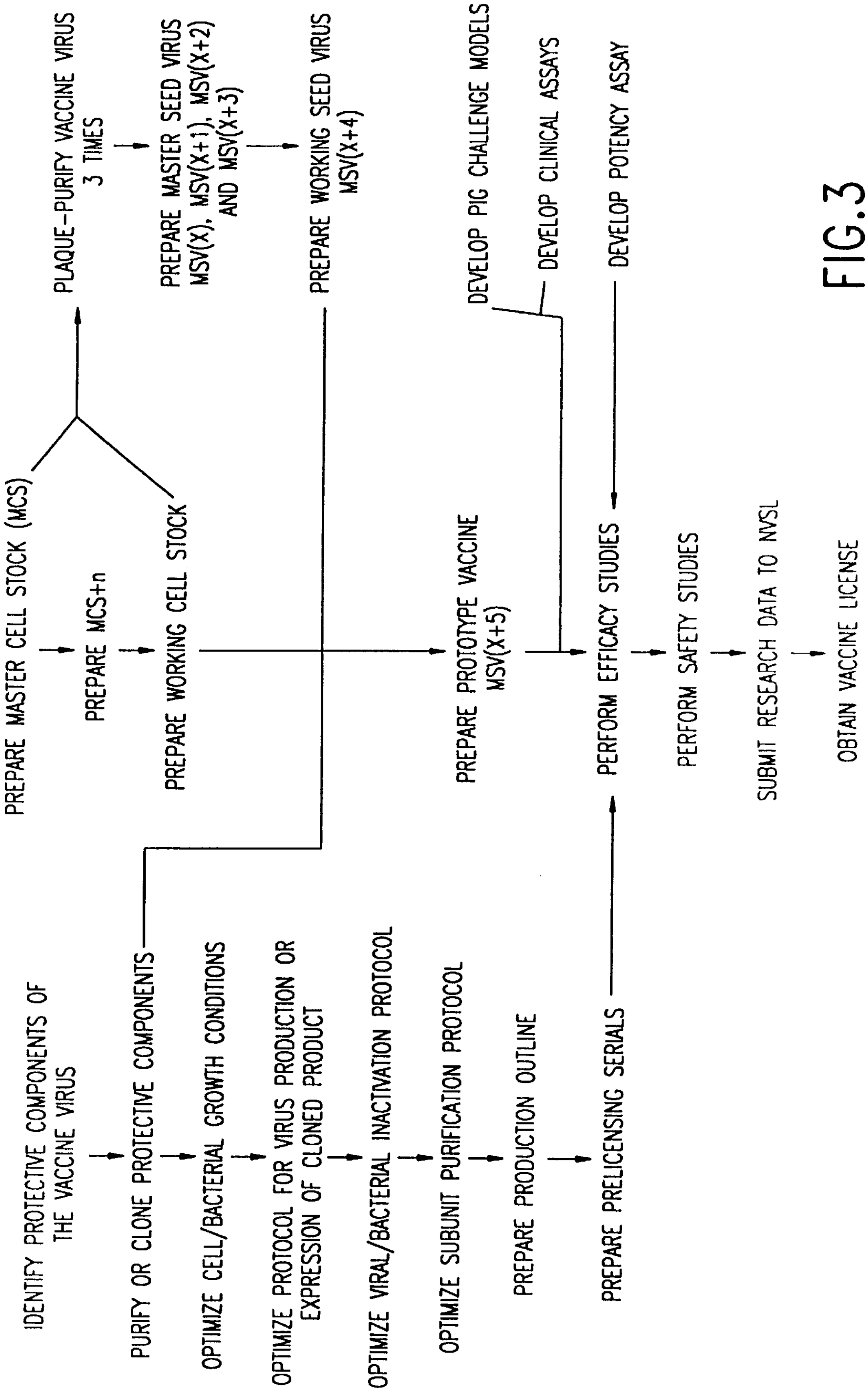
FIG. 3 is a flowchart outlining a procedure for producing a subunit vaccine.
Figure 4:
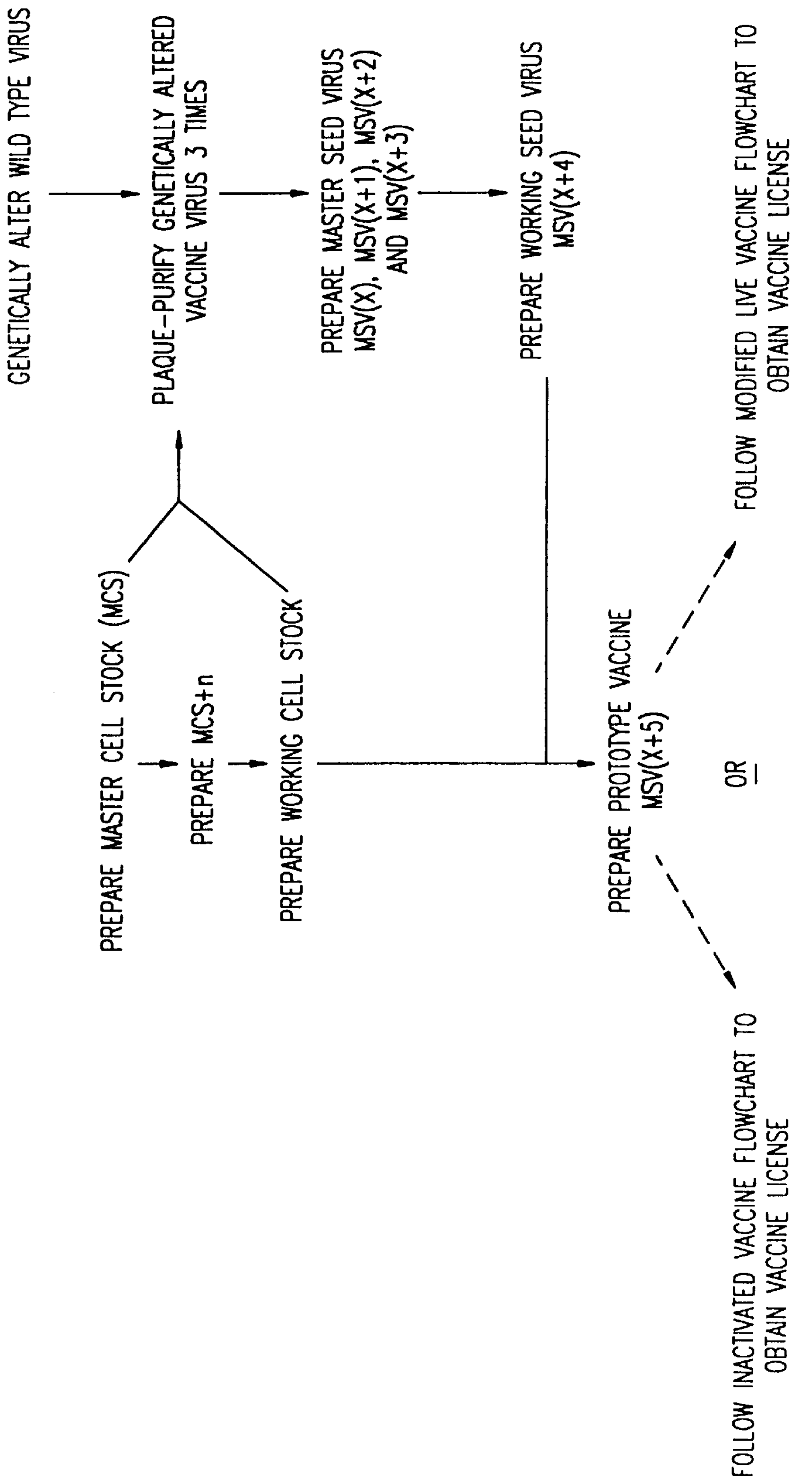
FIG. 4 is a flowchart outlining a procedure for producing a genetically engineered vaccine.

In the present invention, a "porcine respiratory and reproductive disease" refers to the diseases PRRS, PNP and EMCV described above, the disease caused by the Iowa strain of PRRSV, and closely-related variants of these diseases which have appeared and which will appear in the future.

A vaccine "protects a pig against a disease caused by a porcine respiratory and reproductive disease virus or infectious agent" if, after administration of the vaccine to an unaffected pig, lesions in the lung or symptoms of the disease do not appear or are not as severe as in infected, unprotected pigs, and if, after administration of the vaccine to an affected pig, lesions in the lung or symptoms of the disease are eliminated or are not as severe as in infected, unprotected pigs. An unaffected pig is a pig which has either not been exposed to a porcine respiratory and reproductive disease infectious agent, or which has been exposed to a porcine respiratory and reproductive disease infectious agent but is not showing symptoms of the disease. An affected pig is a pig which is showing symptoms of the disease. The symptoms of the porcine respiratory and reproductive disease may be quantified or scored (e.g., temperature/fever, lung lesions [percentage of lung tissue infected]) or semi-quantified (e.g., severity of respiratory distress [explained in detail below]).

A "porcine respiratory and reproductive virus or infectious agent" causes a porcine respiratory and reproductive disease, as described above.

The agent causing the new, more virulent form of PRRS has been termed the "Iowa" strain of PRRSV. The disease caused by some isolates of the "Iowa" strain of PRRS virus has symptoms similar to but more severe than other porcine respiratory and reproductive diseases. Clinical signs may include lethargy, respiratory distress, "thumping" (forced expiration), fevers, roughened haircoats, sneezing, coughing, eye edema and occasionally conjunctivitis. Lesions may include gross and/or microscopic lung lesions and myocarditis. The infectious agent may be a single virus, or may be combined with one or more additional infectious agents (e.g., other viruses or bacteria). In addition, less virulent and non-virulent forms of the Iowa strain have been found, which may cause a subset of the above symptoms or may cause no symptoms at all, but which can be used according to the present invention to provide protection against porcine reproductive and respiratory diseases nonetheless.

Histological lesions in the various porcine diseases are different. Table I below compares physiological observations and pathology of the lesions associated with a number of diseases caused by porcine viruses:

TABLE I

| | Swine Viral Pneumonia Comparative Pathology | | | | | | |
|---|---|---|---|---|---|---|---|
| Lesion | PRRS(p) | PRRS(o) | SIV | PNP | PRCV | PPMV | Iowa |
| Type II | + | +++ | + | +++ | ++ | ++ | ++++ |
| Inter. thickening | ++++ | + | + | + | ++ | ++ | + |
| Alveolar exudate | + | +++ | ++ | ++ | ++ | ++ | +++ |
| Airway necrosis | – | – | ++++ | ++++ | +++ | + | – |
| Syncytia | – | ++ | +/– | ++ | + | + | +++ |
| Encephalitis | + | +++ | – | – | – | ++ | + |
| Myocarditis | +/– | ++ | – | – | – | – | +++ |

wherein "PRRS(p)" represents the published pathology of the PRRS virus, "PRRS(o)" represents the pathology of PRRS virus observed by the present Inventors, "SIV" represents swine influenza A virus, "PRCV" represents porcine respiratory coronavirus, "PPMV" represents porcine paramyxovirus, "Iowa" refers to the new strain of PRRSV discovered by the present Inventors, "Type II" refers to Type II pneumocytes (which proliferate in infected pigs), "Inter." refers to interstitial, "Airway necrosis" refers to necrosis in terminal airways, and the symbols (–) and (+) through (++++) refer to a comparative severity scale as follows:

(–): negative (not observed)

(+): mild (just above the threshold of observation)

(++): moderate (+++): severe (++++): most severe

The Iowa strain of PRRSV has been identified by the present Inventors in the Midwestern U.S., in association with PRRS. It is not yet clear whether the disease associated with the Iowa strain of PRRSV as it is found naturally is due to a unique virus, or a combination of a virus with one (or more) additional infectious agent(s). However, plaque-purified samples of the Iowa strain of PRRSV appear to be a single, unique virus. Therefore, "the Iowa strain of PRRSV" refers to either a unique, plaque-purified virus or a tissue homogenate from an infected animal which may contain a combination of a virus with one (or more) additional infectious agent(s), and a pig infected with the Iowa strain of PRRSV shows one or more of the symptoms characteristic of the disease caused by the Iowa strain of PRRSV, as described above.

Recent evidence indicates that the Iowa strain of PRRSV differs from the infectious agent which causes conventional PRRS. For example, lesions observed in infected pigs exhibiting symptoms of the disease caused by the Iowa strain of PRRSV are more severe than lesions observed in pigs infected with a conventional, previously-described PRRS virus alone, and pigs suffering from the disease caused by the Iowa strain of PRRSV are also seronegative for influenza, including viruses associated with PNP.

Referring now to FIGS. 1–4, flowcharts of procedures are provided for preparing various types of vaccines encompassed by the present invention. The flowcharts of FIGS. 1–4 are provided as exemplary methods of producing the present vaccines, and are not intended to limit the present invention in any manner.

The first step in each procedure detailed in FIGS. 1–4 is to identify a cell line susceptible to infection with a porcine respiratory and reproductive virus or infectious agent. (To simplify the discussion concerning preparation of the vaccine, the term "virus" means virus and/or other infectious agent associated with a porcine respiratory and reproductive disease.) A master cell stock (MCS) of the susceptible host cell is then prepared. The susceptible host cells continue to be passaged beyond MCS. Working cell stock (WCS) is prepared from cell passages between MCS and MCS+n.

A master seed virus is propagated on the susceptible host cell line, between MCS and MCS+n, preferably on WCS. The raw virus is isolated by methods known in the art from appropriate, preferably homogenized, tissue samples taken from infected pigs exhibiting disease symptoms corresponding to those caused by the virus of interest. A suitable host cell, preferably a sample of the WCS, is infected with the raw virus, then cultured. Vaccine virus is subsequently isolated and plaque-purified from the infected, cultured host cell by methods known in the art. Preferably, the virus to be used to prepare the vaccine is plaque-purified three times.

Master seed virus (MSV) is then prepared from the plaque-purified virus by methods known in the art. The MSV(X) is then passaged in WCS at least four times through MSV(X+1), MSV(X+2), MSV(X+3) and MSV(X+4) virus passages. The MSV(X+4) is considered to be the working seed virus. Preferably, the virus passage to be used in the pig studies and vaccine product of the present invention is MSV(X+5), the product of the fifth passage.

In conjunction with the working cell stock, the working seed virus is cultured by known methods in sufficient amounts to prepare a prototype vaccine, preferably MSV (X+5). The present prototype vaccines may be of any type suitable for use in the veterinary medicine field. Suitable types include a modified live or attenuated vaccine (FIG. 1), an inactivated or killed vaccine (FIG. 2), a subunit vaccine (FIG. 3), a genetically engineered vaccine (FIG. 4), and other types of vaccines recognized in the veterinary vaccine art. A killed vaccine may be rendered inactive through chemical treatment or heat, etc., in a manner known to the artisan of ordinary skill.

In the procedures outlined by each of FIGS. 1–4, following preparation of a prototype vaccine, pig challenge models and clinical assays are conducted by methods known in the art. For example, before performing actual vaccination/challenge studies, the disease to be prevented and/or treated must be defined in terms of its symptoms, clinical assay results, conditions etc. As described above, the infectious agent associated with the Iowa strain of PRRSV has been defined in terms of its symptoms and conditions. The clinical analysis of the infectious agent associated with the Iowa strain of PRRSV is described in the Examples below.

After the disease is sufficiently defined and characterized, one can administer a prototype vaccine to a pig, then expose the pig to the virus or infectious agent which causes the disease. This is known in the art as "challenging" the pig and its immunological system. After observing the response of the challenged pig to exposure to the virus or infectious agent and analyzing the ability of the prototype vaccine to protect the pig, efficacy studies are then performed by methods known in the art. A potency assay is then developed in a separate procedure by methods known in the art, and prelicensing serials are then produced.

In the preparation of a modified live vaccine as outlined in FIG. 1, once a prototype vaccine is prepared, cell growth conditions and virus production are first optimized, then a production outline is prepared by methods known in the art. Once the production outline is prepared, prelicensing serials are then subsequently prepared by methods known in the art. Prelicensing serials refer to a large-scale production of a promising prototype vaccine, which demonstrates the ability to produce serials with consistent standards. One approach to preparing a prototype live vaccine is to subject the virus-infected cells (preferably, master seed virus-infected cells) to one or more cycles of freezing and thawing to lyse the cells. The frozen and thawed infected cell culture material may be lyophilized (freeze-dried) to enhance preservability for storage. After subsequent rehydration, the material is then used as a live vaccine.

The procedure for preparing prelicensing serials for an inactivated vaccine (FIG. 2) is similar to that used for the preparation of a modified live vaccine, with one primary modification. After optimization of cell growth conditions and virus production protocol, a virus inactivation protocol must then be optimized prior to preparation of a suitable production outline. Virus inactivation protocols and their optimization are generally known to those in the art, and may vary in a known or predictable manner, depending on the particular virus being studied.

The preparation of a subunit vaccine (FIG. 3) differs from the preparation of a modified live vaccine or inactivated vaccine. Prior to preparation of the prototype vaccine, the protective or antigenic components of the vaccine virus must be identified. Such protective or antigenic components include certain amino acid segments or fragments of the viral coat proteins which raise a particularly strong protective or immunological response in pigs (which are preferably at least 5 amino acids in length, particularly preferably at least 10 amino acids in length); single or multiple viral coat proteins themselves, oligomers thereof, and higher-order associations of the viral coat proteins which form virus substructures or identifiable parts or units of such substructures; oligoglycosides, glycolipids or glycoproteins present on or near the surface of the virus or in viral substructures such as the nucleocapsid; lipoproteins or lipid groups associated with the virus, etc. These components are identified by methods known in the art. Once identified, the protective or antigenic portions of the virus (the "subunit") are subsequently purified and/or cloned by methods known in the art.

The preparation of prelicensing serials for a subunit vaccine (FIG. 3) is similar to the method used for an inactivated vaccine (FIG. 2), with some modifications. For example, if the subunit is being produced through recombinant genetic techniques, expression of the cloned subunit may be optimized by methods known to those in the art (see, for example, relevant sections of Maniatis et al, "Molecular Cloning: A Laboratory Manual," Cold Spring Harbor Laboratory (1989), Cold Spring Harbor, Mass.). On the other hand, if the subunit being employed represents an intact structural feature of the virus, such as an entire coat protein, the procedure for its isolation from the virus must then be optimized. In either case, after optimization of the inactivation protocol, the subunit purification protocol may be optimized prior to preparation of the production outline.

Genetically engineered vaccines (FIG. 4) begin with a modification of the general procedure used for preparation of the other vaccines. After plaque-purification, the wild-type virus may be isolated from a suitable tissue homogenate by methods known in the art, preferably by conventional cell culture methods using PSP-36 or macrophage cells as hosts.

The RNA is extracted from the biologically pure virus or infectious agent by methods known in the art, preferably by the guanidine isothiocyanate method using a commercially available RNA isolation kit (for example, the kit available from Stratagene, La Jolla, Calif.), and purified by methods known in the art, preferably by ultracentrifugation in a CsCl gradient. RNA may be further purified or enriched by oligo (dT)-cellulose column chromatography.

The viral genome is then cloned into a suitable host by methods known in the art (see Maniatis et al, cited above), and the virus genome is then analyzed to determine essential regions of the genome for producing antigenic portions of the virus. Thereafter, the procedure is generally the same as for a modified live vaccine, an inactivated vaccine or a subunit vaccine.

The present vaccine protects pigs against a virus or infectious agent which causes a porcine reproductive and respiratory disease. Preferably, the present vaccine protects pigs against the infectious agent associated with the Iowa strain of PRRSV. However, the present vaccine is also expected to protect a pig against infection by exposure to closely related variants of the infectious agent associated with the Iowa strain of PRRSV.

Relatively few viruses are amenable to the production of live virus vaccines. The advantages of live virus vaccines is that all possible immune responses are activated in the recipient of the vaccine, including systemic, local, humoral and cell-mediated immune responses. The disadvantages of live virus vaccines lie in the potential for contamination with live adventitious agents, such as SV40 virus and bovine viral diarrhea virus, a common contaminant of bovine fetal serum. This risk, plus the risk that the virus may revert to virulence in the field or may not be attenuated with regard to the fetus, young animals and other species, may outweigh the advantages of a live vaccine.

Inactivated virus vaccines can be prepared by treating viruses with inactivating agents such as formalin or hydrophobic solvents, acid, etc., by irradiation with ultraviolet light or X-rays, by heating, etc. Inactivation is conducted in a manner understood in the art. A virus is considered inactivated if it is unable to infect a cell susceptible to infection. For example, in chemical inactivation, a suitable virus sample or serum sample containing the virus is treated for a sufficient length of time with a sufficient amount or concentration of inactivating agent at a sufficiently high (or low, depending on the inactivating agent) temperature or pH to inactivate the virus. Inactivation by heating is conducted at a temperature and for a length of time sufficient to inactivate the virus. Inactivation by irradiation is conducted using a wavelength of light or other energy for a length of time sufficient to inactivate the virus. Examples of inactivated vaccines for human use include influenza vaccine, poliomyelitis, rabies and hepatitis type B. A successful and effective example of an inactivated vaccine for use in pigs is the porcine parvovirus vaccine.

Subunit virus vaccines are prepared from semi-purified virus subunits by the methods described above in the discussion of FIG. 3. For example, hemagglutinin isolated from influenza virus and neuraminidase surface antigens isolated from influenza virus have been prepared, and shown to be less toxic than the whole virus. Alternatively, subunit vaccines can be prepared from highly purified subunits of the virus. An example in humans is the 22-nm surface antigen of human hepatitis B virus. Human herpes simplex virus subunits and many other examples of subunit vaccines for use in humans are known.

Attenuated virus vaccines can be found in nature and may have naturally-occurring gene deletions, or alternatively, may be prepared by a variety of known methods, such as serial passage in cell cultures or tissue cultures. Viruses can also be attenuated by gene deletions or gene mutations.

Genetically engineered vaccines are produced by techniques known to those in the art. Such techniques include those using recombinant DNA and those using live viruses. For example, certain virus genes can be identified which code for proteins responsible for inducing a stronger immune or protective response in pigs. Such identified genes can be cloned into protein expression vectors, such as the baculovirus vector, and used to infect appropriate host cells (see, for example, O'Reilly et al, "Baculovirus Expression Vectors: A Lab Manual," Freeman & Co. (1992)). The host cells are cultured, thus expressing the desired vaccine proteins, which can be purified to a desired extent, then used to protect the pigs from a respiratory and reproductive disease.

Genetically engineered proteins may be expressed in insect cells, yeast cells or mammalian cells. The genetically engineered proteins, which may be purified and/or isolated by conventional methods, can be directly inoculated into animals to confer protection against porcine reproductive and respiratory diseases. Envelope proteins from a porcine reproductive and respiratory disease infectious agent or virus are used in a vaccine to induce neutralizing antibodies. Nucleoproteins from a porcine reproductive and respiratory disease infectious agent or virus are used in a vaccine to induce cellular immunity.

Preferably, the present invention transforms an insect cell line (HI-FIVE) with a transfer vector containing polynucleic acids obtained from the Iowa strain of PRRSV. Preferably, the present transfer vector comprises linearized baculovirus DNA and a plasmid containing polynucleic acids obtained from the Iowa strain of PRRSV. The host cell line may be co-transfected with the linearized baculovirus DNA and a plasmid, so that a recombinant baculovirus is made. Particularly preferably, the present polynucleic acid encodes one or more proteins of the Iowa strain of PRRSV.

Alternatively, RNA or DNA from a porcine reproductive and respiratory disease infectious agent or virus encoding one or more envelope proteins and/or nucleoproteins can be inserted into live vectors, such as a poxvirus or an adenovirus, and used as a vaccine.

Thus, the present invention further concerns a polynucleic acid isolated from a portion of the genome of a virus causing a respiratory and reproductive disease, preferably a polynucleic acid isolated from a portion of the genome of the Iowa strain of PRRSV. The phrase "polynucleic acid" refers to RNA or DNA, as well as RNA and cDNA corresponding to or complementary to the RNA or DNA from the infectious agent. The present polynucleic acid has utility as a means for producing the present vaccine, as a means for screening or identifying infected animals, and as a means for identifying related viruses and infectious agents.

In one embodiment of the present invention, the polynucleic acid encodes one or more proteins of a virus causing a respiratory and reproductive disease, preferably one or both of the viral membrane (envelope) protein and the capsid protein (nucleoprotein). Particularly preferably, the present polynucleic acid is taken from a 2 kb fragment from the 3'-end of the genome, and encodes one or more of the envelope proteins encoded by ORF-5 and ORF-6 and/or the nucleoprotein encoded by ORF-7 of the genome of the Iowa strain of PRRSV. Most preferably, the polynucleic acid is isolated from the genome of an infectious agent associated with the Iowa strain of PRRSV; for example, the agent described in Experiments I–III below (ISU-12), and is selected from the group consisting of ORF 5 (SEQ ID NO:10), ORF 6 (SEQ ID NO:12), ORF 7 (SEQ ID NO:15) and the 1938-bp 3'-terminal sequence of the ISU-12 genome (SEQ ID NO:8).

In the context of the present application, the proteins or peptides encoded by RNA and/or DNA from a virus or infectious agent are considered "immunologically equivalent" if the polynucleic acid has 90% or greater homology with the polynucleic acid encoding the immunogenic protein or peptide. "Homology" in this application refers to the percentage of identical nucleotide or amino acid sequences between two or more viruses of infectious agents. Accordingly, a further aspect of the present invention encompasses an isolated polynucleic acid which is at least 90% homologous to a polynucleic acid obtained from the genome of a virus causing a respiratory and reproductive disease, preferably a polynucleic acid obtained from the genome of the infectious agent associated with the Iowa strain of PRRSV.

Relatively short segments of polynucleic acid (about 20 bp or longer) in the genome of a virus can be used to screen or identify infected animals, and/or to identify related viruses, by methods described herein and known to those of ordinary skill in the art. Accordingly, a further aspect of the present invention encompasses an isolated (and if desired, purified) polynucleic acid consisting essentially of isolated fragments obtained from a portion of the genome of a virus causing a respiratory and reproductive disease, preferably a polynucleic acid obtained from a portion of the genome of the infectious agent associated with the Iowa strain of PRRSV, which are at least 20 nucleotides in length, preferably from 20 to 100 nucleotides in length. Particularly preferably, the present isolated polynucleic acid fragments are obtained from the 1938-bp 3'-terminal sequence of the ISU-12 genome (SEQ ID NO:8), and most preferably, are selected from the group consisting of SEQ ID NO:1, SEQ ID NO:2, SEQ ID NO:3, SEQ ID NO:4, SEQ ID NO:5, SEQ ID NO:6 and SEQ ID NO:7.

The present isolated polynucleic acid fragments can be obtained by digestion of the cDNA corresponding to (complementary to) the viral polynucleic acids with one or more appropriate restriction enzymes, or can be synthesized using a commercially available automated polynucleotide synthesizer.

In another embodiment of the present invention, the polynucleic acid encodes one or more antigenic peptides from a virus causing a respiratory and reproductive disease, preferably the one or more antigenic peptides from the infectious agent associated with the Iowa strain of PRRSV. As described above, the present polynucleic acid encodes an antigenic portion of a protein from a virus causing a respiratory and reproductive disease, preferably from the infectious agent associated with the Iowa strain of PRRSV, at least 5 amino acids in length, particularly preferably at least 10 amino acids in length. Methods of determining the antigenic portion of a protein are known to those of ordinary skill in the art.

The present invention further concerns a biologically pure sample of a virus or infectious agent causing a sequence selected from the group consisting of SEQ ID NO:8, SEQ ID NO:10, SEQ ID NO:12, SEQ ID NO:15 and SEQ ID NO:16. The present proteins and antigenic peptides are useful in serological tests for screening pigs for exposure to PRRSV, particularly to the Iowa strain of PRRSV.

The present invention further concerns a biologically pure sample of a virus or infectious agent causing a porcine reproductive and respiratory disease characterized by the following symptoms and clinical signs: lethargy, respiratory distress, forced expiration, fevers, roughened haircoats, sneezing, coughing, eye edema and occasionally conjunctivitis. The present biologically pure sample of a virus or infectious agent may be further characterized in that it causes a porcine reproductive and respiratory disease which may include the following histological lesions: gross and/or microscopic lung lesions, Type II pneumocyte, myocarditis, encephalitis, alveolar exudate formation and syncytia formation. The phrase "biologically pure" refers to a sample of a virus or infectious agent in which all progeny a derived from a single parent. Usually, a "biologically pure" sample is achieved by 3×plaque purification in cell culture. In particular, the present biologically pure virus or infectious agent is the Iowa strain of porcine reproductive and respiratory syndrome, samples of which have been deposited under the terms of the Budapest Treaty at the American Type Culture Collection, 10801 University Boulevard, Mannassas, Va. 20110-2209, U.S.A., under the accession numbers VR 2385, VR 2386, VR 2492, VR 2428, VR 2430, and VR 2431.

The Iowa strain of PRRSV may also be characterized by Northern blots of its mRNA. For example, the Iowa strain of PRRSV may contain either 7 or 9 mRNA's, which may also have deletions therein. In particular, as will be described in the Experiments below, the mRNA's of the Iowa strain of PRRSV may contain up to four deletions.

The present invention further concerns a composition for protecting a pig from viral infection, comprising an amount of the present vaccine effective to raise an immunological response to a virus which causes a porcine reproductive and respiratory disease in a physiologically acceptable carrier.

An effective amount of the present vaccine is one in which a sufficient immunological response to the vaccine is raised to protect a pig exposed to a virus which causes a porcine reproductive and respiratory disease or related illness. Preferably, the pig is protected to an extent in which from one to all of the adverse physiological symptoms or effects (e.g., lung lesions) of the disease to be prevented are found to be significantly reduced.

The composition can be administered in a single dose, or in repeated doses. Dosages may contain, for example, from 1 to 1,000 micrograms of virus-based antigen (vaccine), but should not contain an amount of virus-based antigen sufficient to result in an adverse reaction or physiological symptoms of infection. Methods are known in the art for determining suitable dosages of active antigenic agent.

The composition containing the present vaccine may be administered in conjunction with an adjuvant. An adjuvant is a substance that increases the immunological response to the present vaccine when combined therewith. The adjuvant may be administered at the same time and at the same site as the vaccine or at a different time, for example, as a booster. Adjuvants also may advantageously be administered to the animal in a manner or at a site or location different from the manner, site or location in which the vaccine is administered. Adjuvants include aluminum hydroxide, aluminum potassium sulfate, heat-labile or heat-stable enterotoxin isolated from *Escherichia coli,* cholera toxin or the B subunit thereof, diphtheria toxin, tetanus toxin, pertussis toxin, Freund's incomplete adjuvant, Freund's complete adjuvant, and the like. Toxin-based adjuvants, such as diphtheria toxin, tetanus toxin and pertussis toxin, may be inactivated prior to use, for example, by treatment with formaldehyde.

The present invention also concerns a method of protecting a pig from infection against a virus which causes a porcine respiratory and reproductive disease, comprising administering an effective amount of a vaccine which raises an immunological response against such a virus to a pig in need of protection against infection by such a virus. By "protecting a pig from infection" against a porcine respiratory and reproductive virus or infectious agent, it is meant that after administration of the present vaccine to a pig, the pig shows reduced (less severe) or no clinical symptoms (such as fever) associated with the corresponding disease, relative to control (infected) pigs. The clinical symptoms may be quantified (e.g., fever, antibody count, and/or lung lesions), or semi-quantified (e.g., severity of respiratory distress).

In the present invention, a system for measuring respiratory distress in affected pigs has been developed. The present clinical respiratory scoring system evaluates the respiratory distress of affected pigs by the following scale:

| | |
|---|---|
| 0 = | no disease; normal breathing |
| 1 = | mild dyspnea and polypnea when the pigs are stressed (forced to breathe in larger volumes and/or at an accelerated rate) |
| 2 = | mild dyspnea and polypnea when the pigs are at rest |
| 3 = | moderate dyspnea and polypnea when the pigs are stressed |
| 4 = | moderate dyspnea and polypnea when the pigs are at rest |
| 5 = | severe dyspnea and polypnea when the pigs are stressed |
| 6 = | severe dyspnea and polypnea when the pigs are at rest |

In the present clinical respiratory scoring system, a score of "0" is normal, and indicates that the pig is unaffected by a porcine respiratory and reproductive disease. A score of "3" indicates moderate respiratory disease, and a score of "6" indicates very severe respiratory disease. An amount of the present vaccine or composition may be considered effective if a group of challenged pigs given the vaccine or composition show a lower average clinical respiratory score than a group of identically challenged pigs not given the vaccine or composition. (A pig is considered "challenged" when exposed to a concentration of an infectious agent sufficient to cause disease in a non-vaccinated animal.)

Preferably, the present vaccine composition is administered directly to a pig not yet exposed to a virus which causes a reproductive or respiratory disease. The present vaccine may be administered orally or parenterally. Examples of parenteral routes of administration include intradermal, intramuscular, intravenous, intraperitoneal, subcutaneous and intranasal routes of administration.

When administered as a solution, the present vaccine may be prepared in the form of an aqueous solution, a syrup, an elixir, or a tincture. Such formulations are known in the art, and are prepared by dissolution of the antigen and other appropriate additives in the appropriate solvent systems. Such solvents include water, saline, ethanol, ethylene glycol, glycerol, A1 fluid, etc. Suitable additives known in the art include certified dyes, flavors, sweeteners, and antimicrobial preservatives, such as thimerosal (sodium ethylmercurithiosalicylate). Such solutions may be stabilized, for example, by addition of partially hydrolyzed gelatin, sorbitol, or cell culture medium, and may be buffered by methods known in the art, using reagents known in the art, such as sodium hydrogen phosphate, sodium dihydrogen phosphate, potassium hydrogen phosphate and/or potassium dihydrogen phosphate.

Liquid formulations may also include suspensions and emulsions. The preparation of suspensions, for example using a colloid mill, and emulsions, for example using a homogenizer, is known in the art.

Parenteral dosage forms, designed for injection into body fluid systems, require proper isotonicity and pH buffering to the corresponding levels of porcine body fluids. Parenteral formulations must also be sterilized prior to use.

Isotonicity can be adjusted with sodium chloride and other salts as needed. Other solvents, such as ethanol or propylene glycol, can be used to increase solubility of ingredients of the composition and stability of the solution. Further additives which can be used in the present formulation include dextrose, conventional antioxidants and conventional chelating agents, such as ethylenediamine tetraacetic acid (EDTA).

The present invention also concerns a method of producing the present vaccine, comprising the steps of:

(A) collecting a virus or infectious agent which causes a porcine respiratory and reproductive disease, and (B) treating the virus or infectious agent in a manner selected from the group consisting of (i) plaque-purifying the virus or infectious agent, (ii) heating the virus or infectious agent at a temperature and for a time sufficient to deactivate the virus or infectious agent, (iii) exposing or mixing the virus or infectious agent with an amount of an inactivating chemical sufficient to inactivate the virus or infectious agent, (iv) breaking down the virus or infectious agent into its corresponding subunits and isolating at least one of the subunits, and (v) synthesizing or isolating a polynucleic acid encoding a surface protein of the virus or infectious agent, infecting a suitable host cell with the polynucleic acid, culturing the host cell, and isolating the surface protein from the culture.

Preferably, the virus or infectious agent is collected from a culture medium by the steps of (i) precipitating infected host cells, (ii) lysing the precipitated cells, and (iii) centrifuging the virus or infectious agent prior to the subsequent treatment step. Particularly preferably, the host cells infected with the virus or infectious agent are cultured in a suitable medium prior to collecting.

Preferably, after culturing infected host cells, the infected host cells are precipitated by adding a solution of a conventionally-used poly(ethylene glycol) (PEG) to the culture medium, in an amount sufficient to precipitate the infected cells. The precipitated infected cells may be further purified by centrifugation. The precipitated cells are then lysed by methods known to those of ordinary skill in the art. Preferably, the cells are lysed by repeated freezing and thawing (three cycles of freezing and thawing is particularly preferred). Lysing the precipitated cells releases the virus, which may then be collected, preferably by centrifugation. The virus may be isolated and purified by centrifuging in a CsCl gradient, then recovering the appropriate virus-containing band from the CsCl gradient.

Alternatively, the infected cell culture may be frozen and thawed to lyse the cells. The frozen and thawed cell culture material may be used directly as a live vaccine. Preferably, however, the frozen and thawed cell culture material is lyophilized (for storage), then rehydrated for use as a vaccine.

The culture media may contain buffered saline, essential nutrients and suitable sources of carbon and nitrogen recognized in the art, in concentrations sufficient to permit growth of virus-infected cells. Suitable culture media include Dulbecco's minimal essential medium (DMEM), Eagle's minimal essential medium (MEM), Ham's medium, medium 199, fetal bovine serum, fetal calf serum, and other equivalent media which support the growth of virus-infected cells. The culture medium may be supplemented with fetal bovine serum (up to 10%) and/or L-glutamine (up to 2 mM), or other appropriate additives, such as conventional growth supplements and/or antibiotics. A preferred medium is DMEM.

Preferably, the present vaccine is prepared from a virus or infectious agent cultured in an appropriate cell line. The cell line is preferably PSP-36 or an equivalent cell line capable of being infected with the virus and cultured. An example of a cell line equivalent to PSP-36 is the cell line PSP-36-SAH, which was deposited under the terms of the Budapest Treaty at the American Type Culture Collection, 10801 University Boulevard, Manassas, Va. 20110-2209, U.S.A., on Oct. 28, 1992, under the deposit number CRL 11171. Another equivalent cell line is MA-104, available commercially from Whittaker Bioproducts, Inc. (Walkersville, Md.). Preliminary results indicate that the infectious agent associated with the Iowa strain of PRRSV can be cultured in porcine turbinate cells. After plaque purification, the infectious agent associated with the Iowa strain of PRRSV produces the lesions characterized under the heading "Iowa" in Table I above, and shown in FIGS. 5–8.

Accordingly, the present invention also concerns a method of culturing a virus or infectious agent, preferably in a cell line selected from the group consisting of PSP-36 and equivalent cell lines capable of being infected with the virus and cultured. The method of culturing a virus or infectious agent according to the present invention comprises infecting cell line PSP-36 or an equivalent cell line capable of being infected with a virus or infectious agent which causes a porcine respiratory and reproductive disease and cultured, and culturing the infected cell line in a suitable medium.

Preferably, the virus or infectious agent is the Iowa strain of PRRSV, or causes a disease selected from the group consisting of PRRS, PNP, and related diseases. Particularly preferably, the present vaccine is prepared from the Iowa strain of PRRSV, and is cultivated in PSP-36 cells.

The cell line MA-104 is obtained from monkey kidney cells, and is epithelial-like. MA-104 cells form a confluent monolayer in culture flasks containing Dulbecco's minimal essential medium and 10% FBS (fetal bovine serum). When the monolayer is formed, the cells are inoculated with a sample of 10% homogenized tissue, taken from an appropriate tissue (such as lung and/or heart) in an infected pig. Preferably, appropriate antibiotics are present, to permit growth of virus and host cells and to suppress growth and/or viability of cells other than the host cells (e.g., bacteria or yeast).

Both PSP-36 and MA-104 cells grow some isolates of the PRRS virus to high titers (over $10^7$ $TCID_{50}$/ml). PSP-36 and MA-104 cells will also grow the infectious agent associated with the Iowa strain of PRRSV. MA-104 cells also are able to grow rotaviruses, polioviruses, and other viruses.

CL2621 cells are believed to be of non-porcine origin and are epithelial-like, and are proprietary (Boehringer-Mannheim). By contrast to PSP-36 and MA-104, some samples of the virus which causes PRRS have been unsuccessfully cultured in CL2621 cells (Bautista et al, *American Association of Swine Practitioners Newsletter,* 4:32, 1992).

The primary characteristics of CL2621 are that it is of non-swine origin, and is epithelial-like, growing in MEM medium. However, Benfield et al (*J. Vet. Diagn. Invest.,* 1992; 4:127–133) have reported that CL2621 cells were used to propagate PRRS virus, but MA-104 cells were used to control polio virus propagation, thus inferring that CL2621 is not the same as MA-104, and that the same cell may not propagate both viruses.

The infectious agent associated with the Iowa strain of PRRSV generally cannot grow in cell lines other than PSP-36, PSP-36-SAH and MA-104. As described above, however, some viruses which cause PRRS have been reported to grow in both CL2621 and primary swine alveolar macrophages, although some strains of PRRS virus do not grow in PSP-36, MA-104 or CL2621 cells.

The present vaccine can be used to prepare antibodies which may provide immunological resistance to a patient (in this case, a pig) exposed to a virus or infectious agent. Antibodies encompassed by the present invention immunologically bind either to (1) a vaccine which protects a pig against a virus or infectious agent which causes a respiratory and reproductive disease or (2) to the porcine respiratory and reproductive virus or infectious agent itself. The present antibodies also have utility as a diagnostic agent for determining whether a pig has been exposed to a respiratory and reproductive virus or infectious agent, and in the preparation of the present vaccine. The antibody may be used to prepare an immunoaffinity column by known methods, and the immunoaffinity column can be used to isolate the virus or infectious agent, or a protein thereof.

To raise antibodies to such vaccines or viruses, one must immunize an appropriate host animal, such as a mouse, rabbit, or other animals used for such inoculation, with the protein used to prepare the vaccine. The host animal is then immunized (injected) with one of the types of vaccines described above, optionally administering an immune-enhancing agent (adjuvant), such as those described above. The host animal is preferably subsequently immunized from 1 to 5 times at certain intervals of time, preferably every 1 to 4 weeks, most preferably every 2 weeks. The host animals are then sacrificed, and their blood is collected. Sera is then separated by known techniques from the whole blood collected. The sera contains antibodies to the vaccines. Antibodies can also be purified by known methods to provide immunoglobulin G (IgG) antibodies.

The present invention also encompasses monoclonal antibodies to the present vaccines and/or viruses. Monoclonal antibodies may be produced by the method of Kohler et al (*Nature,* vol. 256 (1975), pages 495–497). Basically, the immune cells from a whole cell preparation of the spleen of the immunized host animal (described above) are fused with myeloma cells by a conventional procedure to produce hybridomas. Hybridomas are cultured, and the resulting culture fluid is screened against the fluid or inoculum carrying the infectious agent (virus or vaccine). Introducing the hybridoma into the peritoneum of the host animal produces a peritoneal growth of the hybridoma. Collection of the ascites fluid of the host animal provides a sample of the monoclonal antibody to the infectious agent produced by the hybridoma. Also, supernatant from the hybridoma cell culture can be used as a source of the monoclonal antibody, which is isolated by methods known to those of ordinary skill in the art. Preferably, the present antibody is of the IgG or IgM type of immunoglobulin.

The present invention also concerns a method of treating a pig suffering from a respiratory and reproductive disease, comprising administering an effective amount of an antibody which immunologically binds to a virus which causes a porcine respiratory and reproductive disease or to a vaccine which protects a pig against infection by a porcine respiratory and reproductive virus in a physiologically acceptable carrier to a pig in need thereof.

The present method also concerns a diagnostic kit for assaying a virus which causes a porcine respiratory disease, a porcine reproductive disease, or a porcine reproductive and respiratory disease, comprising the present antibody described above and a diagnostic agent which indicates a positive immunological reaction with said antibody.

The present diagnostic kit is preferably based on modifications to known immunofluorescence assay (IFA), immunoperoxidase assay (IPA) and enzyme-linked immunosorbant assay (ELISA) procedures.

In IFA, infected cells are fixed with acetone and methanol solutions, and antibodies for the convalescent sera of infected pigs are incubated with the infected cells, preferably for about 30 min. at 37° C. A positive immunological reaction is one in which the antibody binds to the virus-infected cells, but is not washed out by subsequent washing steps (usually 3×with PBS buffer). A second antibody (an anti-antibody) labeled with a fluorescent reagent (FITC) is then added and incubated, preferably for anther 30 min. A positive immunological reaction results in the second antibody binding to the first, being retained after washing, and resulting in a fluorescent signal, which can be detected and semi-quantified. A negative immunological reaction results in little or no binding of the antibody to the infected cell. Therefore, the second, fluorescently-labeled antibody fails to bind, the fluorescent label is washed out, and little or no fluorescence is detected, compared to an appropriate positive control.

IPA and ELISA kits are similar to the IFA kit, except that the second antibody is labeled with a specific enzyme, instead of a fluorescent reagent. Thus, one adds an appropriate substrate for the enzyme bound to the second antibody which results in the production of a colored product, which is then detected and quantified by colorimetry, for example.

Other features of the invention will become apparent in the course of the following descriptions of exemplary embodiments, which are given for illustration of the invention, and are not intended to be limiting thereof.

EXPERIMENT 1

In Example 1, a case of endemic pneumonia in 5–8 week old pigs was investigated. Microscopic lesions of the Iowa strain of PRRSV observed in the pigs were compatible with a viral etiology. (Accordingly, hereinafter, to simplify the discussion, the terms "virus" and "viral" will refer to a virus or infectious agent in the meaning described above for the present application, or a property thereof.) The disease was experimentally transmitted to conventional and gnotobiotic pigs using lung homogenate isolated from infected pigs filtered through a 0.22 $\mu$m filter. Common swine viral respiratory pathogens were not demonstrated. Two types of virus particles were observed in cell culture by electron microscopy. One type was about 70 nm in diameter, was enveloped and had short surface spicules. The other type was enveloped, elongated, pleo-morphic, measured 80×320 nm and was coated by antibodies.

(I) Materials and Methods (A) Material From Pigs Infected With Naturally-Occurring Pneumonia Tissues from three infected 6-week-old pigs from a 900-sow farrow-to-feeder-pig herd in Southwestern Iowa were collected and studied. Prior observations of the herd showed that five to seven days after weaning, 50–70% of the similarly-infected pigs became anorexic, were rough-haired, and experienced lethargy, coughing, fever, and "thumping". Approximately 10–25% of the infected pigs had conjunctivitis. Most of the infected pigs recovered in 7–10 days but, 10–15% were severely stunted due to secondary bacterial infections, and were not suitable for sale as feeder pigs. Swine reproductive failure, including increased stillbirths, mummified fetuses, and infertility, had occurred at the time of the original outbreak of the disease in this herd, but later diminished with time. Respiratory disease in the nursery stage has been persistant.

Lung lesions characterized by proliferative bronchiolitis and alveolitis were observed in formalin-fixed tissues from four different 6-week-old pigs. Attempts to isolate SIV, pseudorabies virus (PRV) and encephalomyocarditis virus (EMCV) were not successful. Immunofluorescence examination of frozen sections of lung for swine influenza virus (SIV), pseudorabies virus (PRV), and *Mycoplasma hyopneumoniae* were negative. *Pasteurella multocida* type D was isolated from the nasal cavities and *Haemophilus parasuis* was isolated from the lungs.

Five acutely affected 5–6 week old pigs, which had been weaned for 10 days, were subsequently obtained from the herd. All pigs had fevers of at least 40.5° C. The pigs were necropsied, and lung tissue samples from the pig with gross lesions most typical of a viral pneumonia were collected and prepared for immediate inoculation into conventional specific pathogen-free (SPF) pigs. Lung, liver, kidney, spleen, brain, and heart tissue samples from all five acutely affected 5–6 week old pigs were cultured for common bacterial and viral pathogens. Sections of the same tissues were collected and fixed in 10% neutral buffered formalin for histopathological examination.

(B) Experimental Transmission in Conventional Pigs (1) Experimental Pigs

Sixteen five-week old pigs were obtained from a herd free of mycoplasmas, PRV, porcine respiratory coronavirus (PRCV), and transmissible gastroenteritis virus (TGEV). Eight pigs were placed in each of two isolated 4×5 meter rooms with concrete floors and automated ventilation. The pigs were fed an 18% protein corn-soybean meal ration and water ad libitum.

(2) Experimental Design

Immediately after necropsy of the pigs with naturally occurring pneumonia, a 10% lung homogenate was prepared in Dulbecco's modified Eagle's minimal essential medium, clarified at 1000×g for 10 minutes, followed by centrifugation at 10,000×g for 10 minutes. The clarified supernatant was filtered through a 0.22 μm filter. Eight pigs were inoculated intranasally with 5 ml of filtered lung homogenate. Eight control pigs were inoculated intranasally with 5 ml of filtered lung homogenate prepared as described above from a normal uninfected gnotobiotic pig.

Clinical signs and temperatures were monitored and recorded daily. One pig from each group was euthanized and necropsied at 5, 7, 10 and 15 days post inoculation (DPI), respectively. Tissues were collected at the time of necropsy for aerobic and anaerobic bacterial isolation procedures, mycoplasma isolation, detection of antigens for *Mycoplasma hyopneumoniae,* SIV, PRV, parainfluenza virus type 3 (PI-3), and bovine respiratory syncytial virus (BRSV), and for virus isolation. Tissues were fixed in 10% neutral buffered formalin for histopathological examination. Lungs were fixed by inflation with formalin at the time of necropsy.

(C) Experimental Transmission in Gnotobiotic Pigs (1) Experimental Pigs

Eight colostrum-deprived, caesarean-derived (CDCD), crossbred, one-day-old gnotobiotic pigs were randomly divided into two isolators (four pigs in each isolator). Pigs were fed an iron-fortified, sterilized, canned liquid milk replacer (SPF-LAC, Pet-Ag Inc, Elgin, Ill.)

(2) Experimental Design

Four principal pigs were inoculated with filtered (0.22 μm) lung homogenate intranasally (3 ml) and orally (1 ml) at 3 days of age. This filtrate was prepared from an experimentally infected conventional pig lung which had been collected 7 days post-infection (DPI). Four control pigs were inoculated with lung homogenate prepared from a normal gnotobiotic pig.

One pig from each group was killed at 5, 9, 28, and 35 DPI, respectively. Lung, liver, kidney, brain, spleen, thymus, nasal turbinates, heart, and intestines were collected and fixed in 10% neutral buffered formalin for histopathological examination. Lung, brain, spleen, and heart were collected for virus isolation. Lung, liver, and spleen were collected for bacteriologic isolation. Lung was collected immediately into Friis medium for mycoplasma isolation or was frozen at −70° C.

(D) Microbiological Assays (1) Virus Isolation

Tissue suspensions (10% w/v) clarified at 1000×g were inoculated on to cell monolayers and observed for cytopathic effect. Primary fetal swine kidney cultures, primary porcine alveolar macrophage cultures, and established cell lines of PK15, bovine turbinate, baby hamster kidney (BHK), Vero, and swine testes (ST) were used for the virus isolation attempts. Direct bronchio-alveolar lavage cultures were prepared from infected and control gnotobiotic pigs. Attempts to detect virus were done by indirect immunofluorescence using reference gnotobiotic hyperimmune or convalescent swine serum to porcine parvovirus (PPV), SIV, bovine viral diarrhea virus, hemagglutinating encephalomyelitis virus (HEV), TGEV and EMCV. Filtrates were blindly passed three times by intra-allantoic inoculation of 10-day old embryonated chicken eggs and allantoic fluid tested for hemagglutinating activity after each passage.

(2) Mycoplasma Isolation

Lung suspensions were inoculated into mycoplasma broth medium Friis (Friis (1975), *Acta Vet. Scand.,* 27, 337), BHI-TS, D-TS (Ross et al (1971), *Journal of Bacteriology,* 103, 707) and BHL (Yamamoto et al (1982), *Proc. Int. Pig Vet. Society Congress,* p. 94). Cultures were passaged when growth was evident or on day 3, 7, 14, and 21 and identified by epiimmunofluorescence. (Del Giudice et al (1967), *Journal of Bacteriology,* 93, 1205).

(3) Bacteria Isolation

Nasal turbinate swabs were inoculated on two blood agar plates as well as on MacConkey, Tergitol-7 and PMD (for isolation of *P. multocida*.) agars. One of the blood agar plates was incubated at 37° C. in an anaerobic environment of $CO_2$ and $H_2$. The second plate was cross-streaked with a *Staphylococcus epidermidis* nurse colony and incubated with the other plates in air at 37° C.

Lungs were plated exactly as the nasal turbinate swabs. Liver and spleen were cultured on 2 blood agar plates (aerobic and anaerobic) and a Tergitol-7 plate. All bacterial isolates were identified by standard methods (Biberstein (1990), In: Diagnostic Procedures in Veterinary Bacteriology and Mycology, ed. Carter et al, 5th ed., pp. 129–142, Academic Press Inc., San Diego, Calif.; and Carter (1990) In: Diagnostic Procedures in Veterinary Bacteriology and Mycology, ed. Carter G. R. and Cole J. R., 5th ed., pp. 129–142, Academic Press Inc., San Diego, Calif.).

(4) Serology

Serum neutralization test was used to test for serum antibodies to PRV, TGEV, and EMCV. Hemagglutination inhibition test was used to test serum antibodies to EMCV and HEV. Indirect immunofluorescence test was used to detect serum antibodies to BRSV, PI-3, SIV, and TGEV. Gnotobiotic sera were tested for antibodies to PRRSV. An indirect immunofluorescence assay using cell line CL2621 was used for detection of PRRSV antibodies.

(II) Results (A) Naturally Occurring Pneumonia

The lungs from acutely affected pigs did not collapse. Grossly, the lungs had moderate interlobular edema, and multifocal to coalescing linear areas of atelectasis involving all lung lobes. There was 5–15% cranioventral consolidation of the cranial and middle lobes.

Histopathological examination revealed moderate, acute diffuse proliferative bronchiolitis and alveolitis. There was a mild multifocal lymphoplasmacytic myocarditis. No lesions were seen in other organs.

Virus isolation attempts for adenovirus, PRV, SIV, HEV, porcine respiratory coronavirus (PRCV), porcine parvovirus (PPV), EMCV, and enteroviruses were negative from the original case submission as well as from the acutely affected pigs later obtained from the herd. Immunofluorescence examination of frozen lung sections did not reveal *Mycoplasma hyopneumoniae,* SIV, bovine respiratory syncytial virus (BRSV), parainfluenza virus-3 (PI-3), PRV or TGEV antigens.

Serum from one of the five conventional SPF pigs of section (I)(A) above gave a positive immunological reaction at a dilution of 1:20 for PRRSV by indirect immunofluorescence. *Pasteurella multocida* type D and *Haemophilus parasuis* were isolated, respectively, from the nasal turbinates and lung of this pig. No aerobic or anaerobic bacteria were isolated from the acutely affected pig lung chosen for homogenization and inoculum (see *Methods and Materials,* Section (C)(2) above).

(B) Conventional Pig Study

By 7 DPI, all principal pigs had fevers of 40–41.10° C. and were experiencing moderate respiratory distress. The pigs were anorexic and lethargic. By 15 DPI, the pigs had recovered.

Macroscopic changes in the lungs were characterized by failure to collapse, mild interlobular edema, and tan-grey linear areas of atelectasis multifocally involving from 20–40% of the lung.

Microscopic examination of 7 DPI lungs revealed a patchy interstitial pneumonia characterized by type II pneumocyte proliferation, accumulation of mixed inflammatory cells and necrotic cell debris in alveolar lumina, and infiltration of macrophages and lymphocytes in alveolar septa. Alveolar lumina contained proteinaceous fluid. Occasionally, syncytial-like cells were seen within alveolar lumina and along septa.

Figure 5:
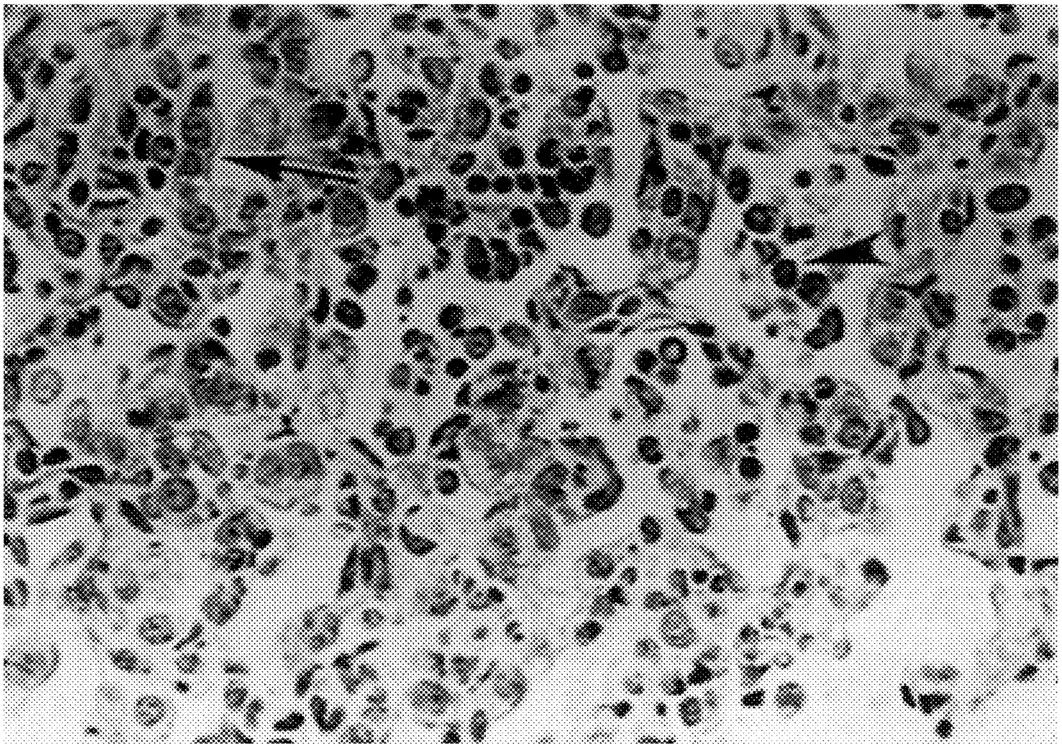
FIGS. 5 and 6 show histological sections from the lungs of conventional pigs 10 days after infection with a sample of the infectious agent isolated from a pig infected with the Iowa strain of PRRSV.

FIG. 5 shows a histological section from the lung of a conventional pig 10 DPI, using hematoxylin-eosin stain. There is extensive type II pneumocyte proliferation (arrow) and necrotic cell debris in alveolar spaces (arrow heads). The condition and appearance of the lesions observed at day 10 were similar to those observed at day 7.

Figure 6:
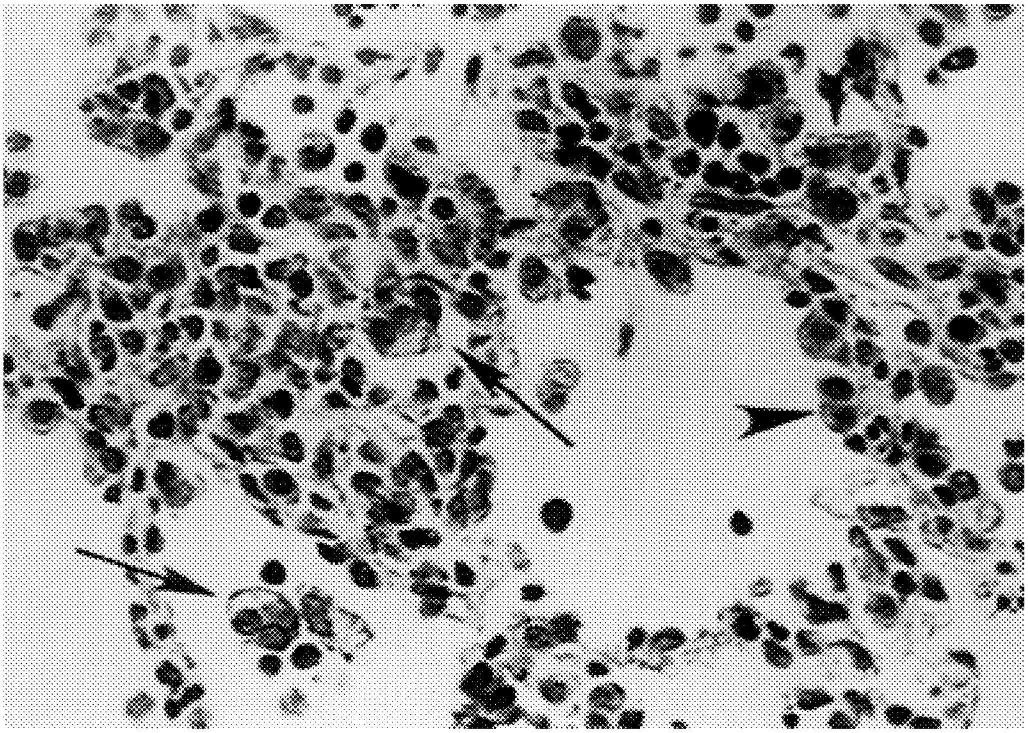

FIG. 6 shows a second histological section from the lung of a conventional pig 10 DPI, using hematoxylin-eosin stain. Syncytial-like cells (arrows) are present in alveolar spaces. Pronounced type II pneumocyte proliferation and more syncytia are observed at day 10 than at day 7.

Lesions were still moderately severe at 15 DPI, yet the pigs appeared clinically normal. No bacteria or mycoplasmas were isolated from the lungs. Virus isolation attempts for EMCV, PRV, PRCV, adenovirus, and SIV were negative. Immunofluorescence examination of frozen lung sections did not demonstrate BRSV, PI-3 virus, PRV, SIV, TGEV, or *Mycoplasma hyopneumoniae* antigens.

No gross or microscopic lesions were seen in control pigs.

(C) Gnotobiotic Pig Study

All inoculated principal pigs were experiencing severe respiratory distress and "thumping" by 5 DPI. Temperatures were 40.5° C. or greater, and the pigs were anorexic and lethargic. The pigs were improved clinically by 8 DPI, and appeared clinically normal by 15 DPI. No pigs died. Control pigs inoculated with normal lung homogenate filtrate remained clinically normal.

Macroscopic lesions by 5 DPI were characterized by a lung that failed to collapse, mild multifocal tan-red atelectasis and mild interlobular edema. Microscopically, there was mild diffuse interstitial pneumonia with multifocal areas of mononuclear cell infiltration of alveolar septae and moderate type II pneumocyte proliferation. There was accumulation of inflammatory cells, necrotic cell debris, and proteinaceous fluid in alveolar lumina. No lesions were seen in other organs.

Figure 7:
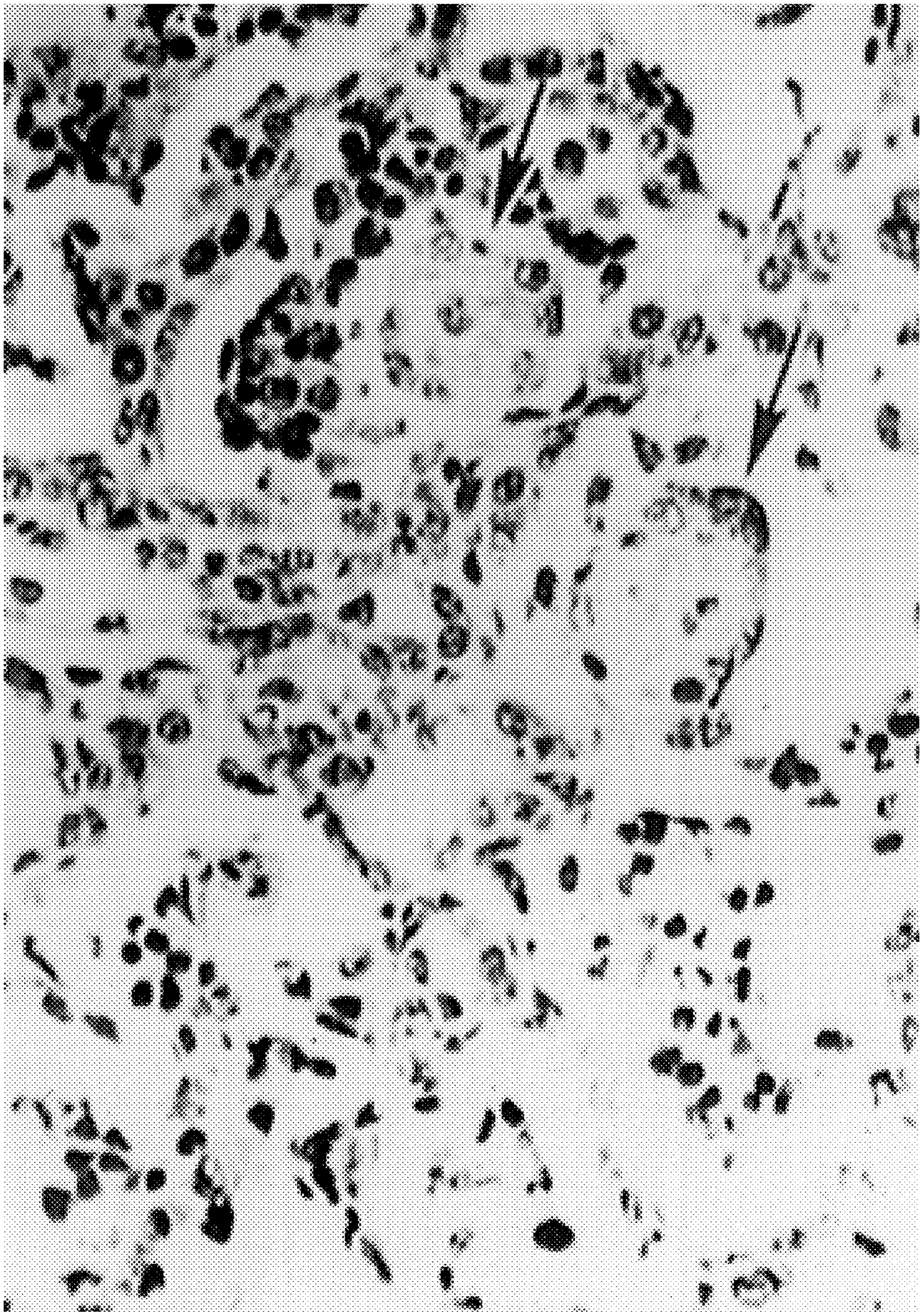
FIG. 7 shows a histological section from the lung of a gnotobiotic pig 9 days after infection with a sample of infectious agent isolated from a pig infected with the Iowa strain of PRRSV.

By 9 DPI, the lung failed to collapse, had moderate interlobular edema and multifocal 1–3 cm areas of firm tan-red atelectasis. FIG. 7 shows a histological section from the lung of a gnotobiotic pig at 9 DPI, using hematoxylin-eosin stain. There is moderate type II pneumocyte proliferation (arrow heads) and syncytial-like cell formation (arrows). Microscopically, the lesions were similar to those observed on day 5 DPI, except that type II pneumocyte proliferation was more pronounced, and there were moderate numbers of syncytial-like cells along alveolar septa and in lumina. The kidney had dilated renal tubules, some containing a lymphoplasmacytic exudate and cell debris.

By 28 DPI, there was 20% cranioventral bilateral atelectasis involving the apical and middle lobes with focal 1–2 cm areas of atelectasis in other lobes. Microscopically, the lung lesions were similar to those observed at 9 DPI, but in addition, there was mild peribronchiolar and periarteriolar lymphoplasmacytic accumulation. Mild to moderate infiltrates of lymphocytes and plasma cells were present multifocally in the choroid plexus, meninges, myocardium, and nasal turbinates.

Figure 8:
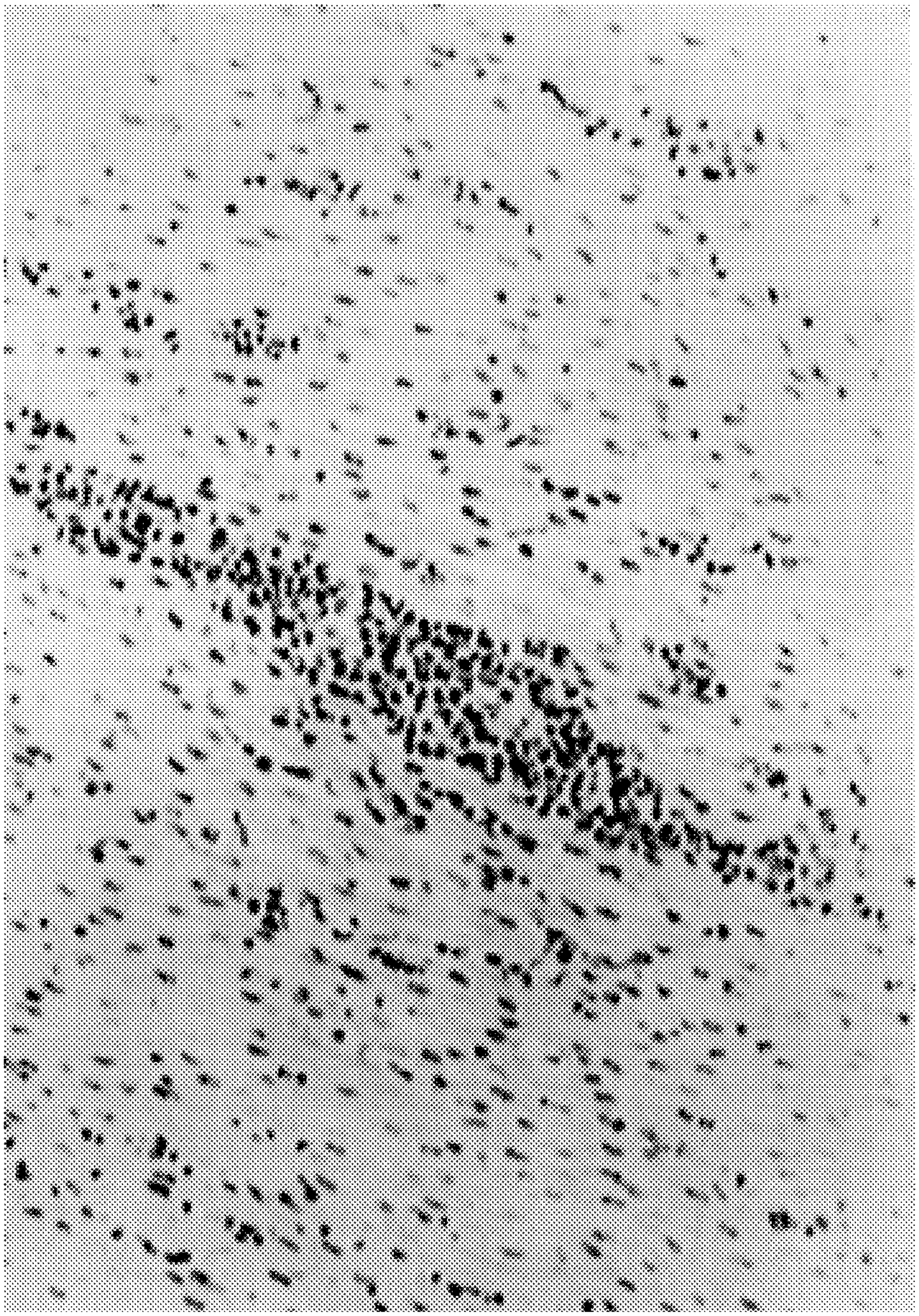
FIG. 8 shows the heart lesions of a gnotobiotic pig 35 days after infection with a sample of an infectious agent isolated from a pig infected with the Iowa strain of PRRSV.
Figure 9:
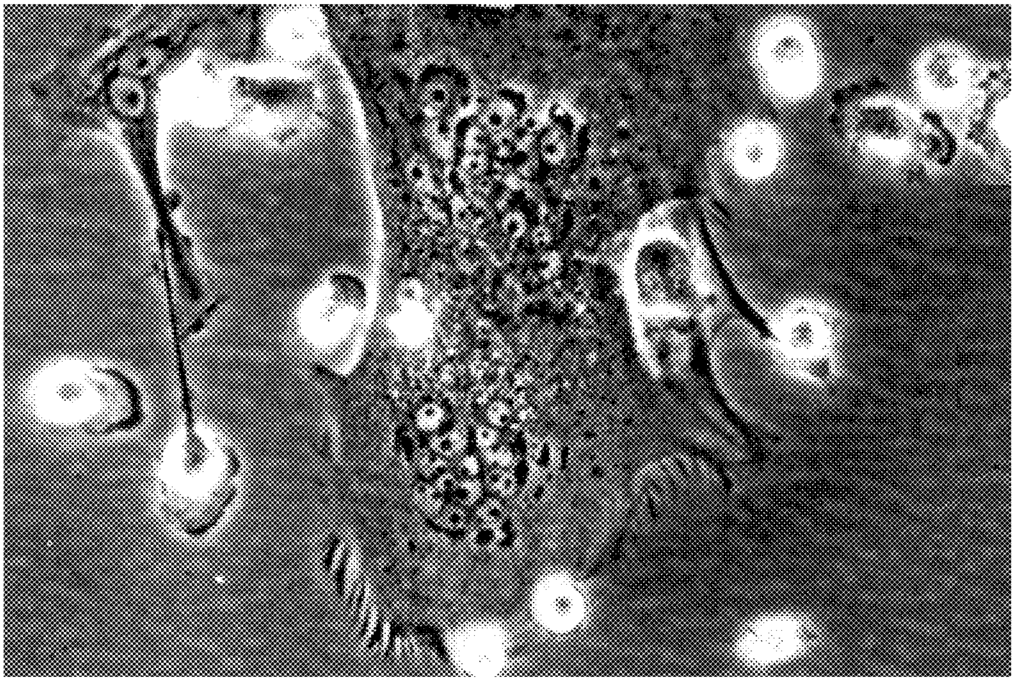
FIG. 9 shows bronchio-alveolar lavage cultures exhibiting extensive syncytia, prepared from a gnotobiotic pig 9 days after infection with a lung filtrate sample of an infectious agent isolated from a pig infected with the Iowa strain of PRRSV (ISU-12; see Experiment I, Section (II)(C) below)
Figure 10:
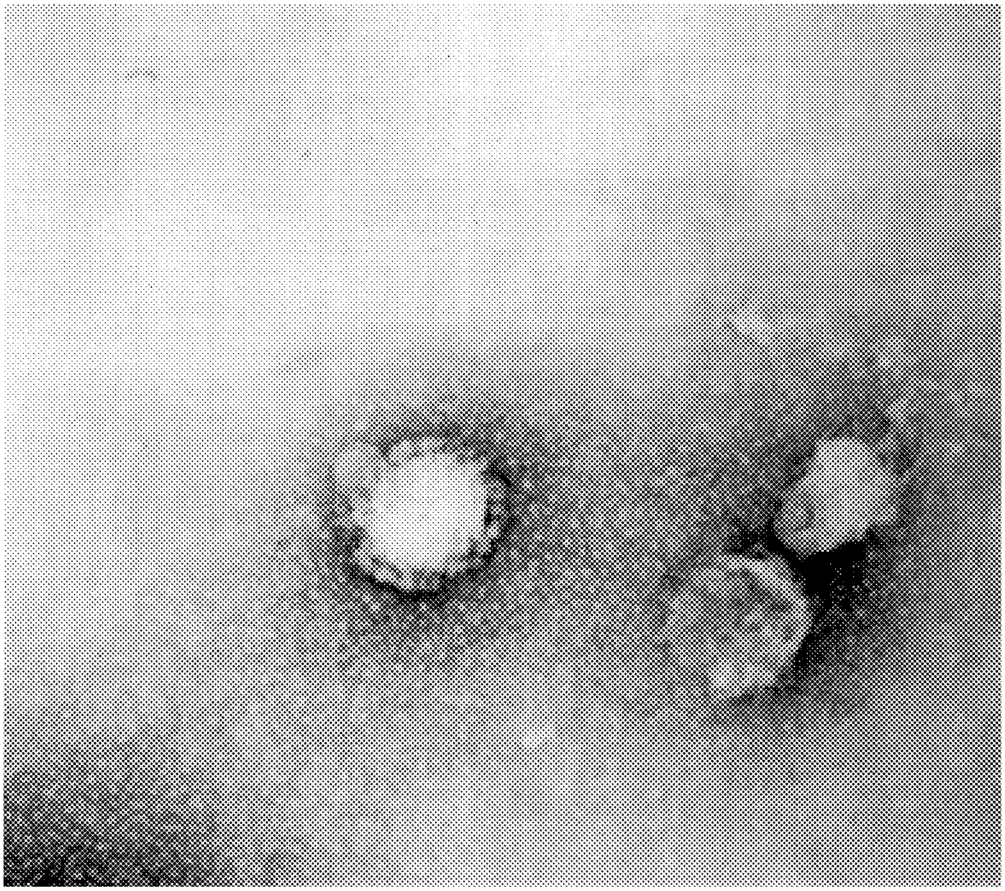
FIG. 10 is an electron micrograph of an enveloped virus particle, about 70 nm in diameter, having short surface spicules, found in alveolar macrophage cultures of pigs infected with an infectious agent associated with the Iowa strain of PRRSV.
Figure 11:
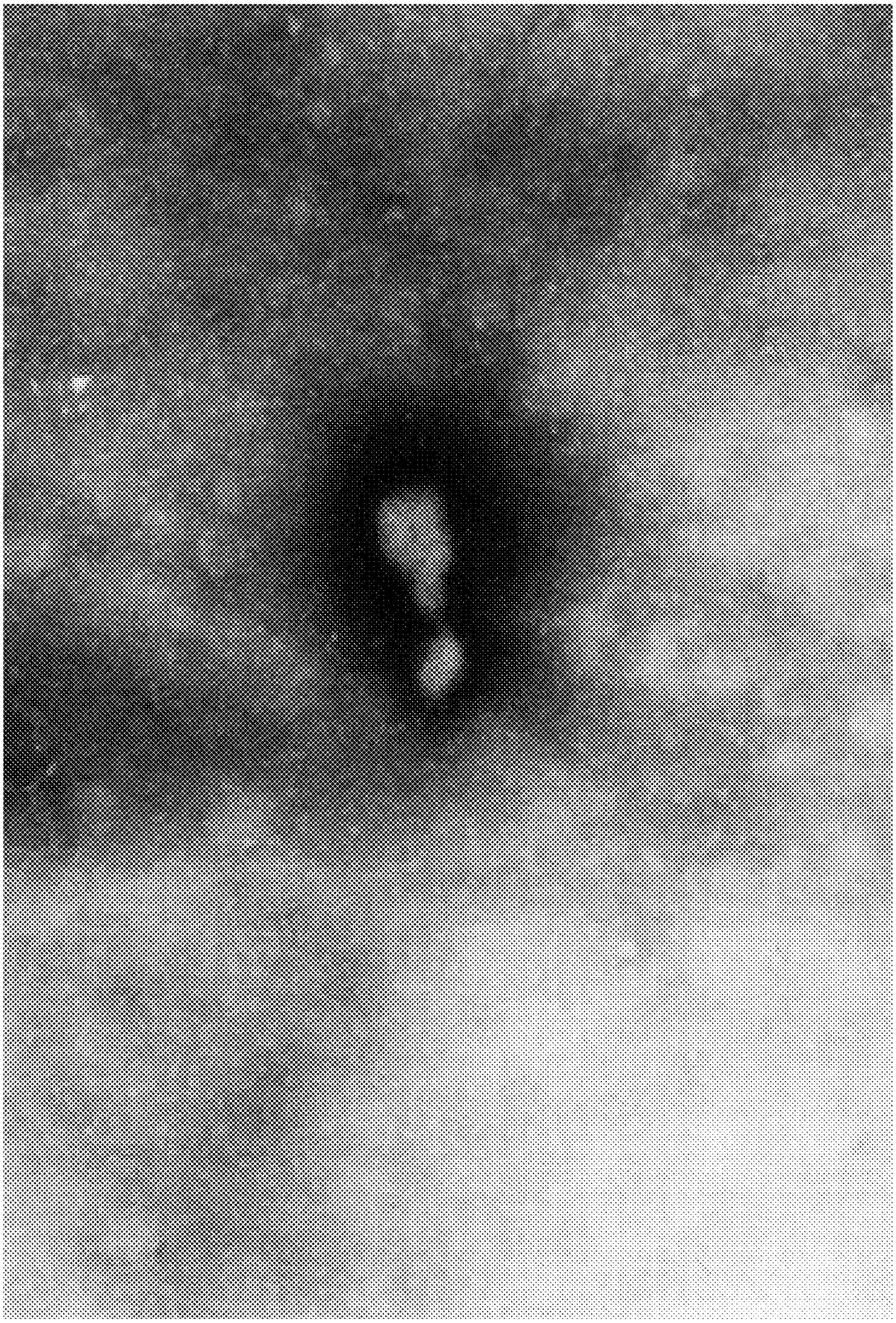
FIG. 11 is an electron micrograph of a pleomorphic, enveloped virus particle, approximately 80×320 nm in size, coated by antibodies, found in alveolar macrophage cultures of pigs infected with the Iowa strain of PRRSV.

FIG. 8 shows that by 35 DPI, the lung lesions were less severe but the multifocal lymphoplasmacytic myocarditis was pronounced. Virus isolation attempts for PRV, SIV, adenovirus, EMCV, HEV, PPV, enteroviruses, and PRCV were unsuccessful. A cytopathic effect was observed in porcine alveolar macrophages, characterized by cell rounding, lysis and cell death. Direct bronchio-alveolar lavage cultures exhibiting extensive syncytia are shown in FIG. 9, which were not observed in similar cultures prepared from control pigs. Examination of these cultures by negative staining immune electron microscopy revealed two types of virus-like particles. One type, shown in FIG. 10, was about 70 nm in diameter, enveloped and had short surface spicules. The other type, shown in FIG. 11, was enveloped, pleomorphic, approximately 80×320 nm and was coated by antibodies. No bacteria were isolated from lung, liver, spleen, or brain.

Serum collected at 28 and 35 DPI had no antibody titers to SIV, EMCV, PRV, TGEV, BRSV, HEV, or PI-3 virus. These sera were positive (1:1280) for antibody to PRRS virus.

The control pigs remained normal throughout the study and had no gross or microscopic lesions in any tissue. No bacteria or viruses were isolated from the control pigs.

(III) Discussion

Lung filtrates from pigs with naturally occurring endemic pneumonia produced lung and heart lesions in experimentally inoculated conventional and gnotobiotic pigs. The lesions observed in both the natural and experimental disease were consistent with a viral etiology.

No common, previously identified swine viral respiratory pathogens were isolated. A cytopathic effect was observed, characterized by cell lysis of primary porcine alveolar macrophage cultures, consistent with the report of PRRS virus infections by Yoon et al (Journal of Veterinary Diagnostic Investigation, vol. 4 (1992), p. 139). However, the large syncytia in direct bronchio-alveolar lavage cultures seen in this study have not been previously reported with PRRS.

Electron microscopy of infected cell culture shows two virus-like particles. A 70 nm enveloped virus-like particle with short surface spicules appears compatible with the PRRS virus as reported by Benfield et al (Journal of Veterinary Diagnostic Investigation, vol. 4 (1992), p. 117), but the other virus-like particle appears to be distinct. None of the pigs developed antibody titers to SIV, PRV, TGEV (PRCV) or EMCV. The gnotobiotic pigs did seroconvert to the PRRS virus, however.

The clinical disease reproduced in Experiment I is characterized by moderate to severe respiratory distress in all inoculated gnotobiotic and conventional pigs within 5 DPI. The disease in this Experiment is more severe than that observed in previous experiments (Collins et al and Yoon et al, supra).

Terminal airway epithelial necrosis and proliferation, described for the recently-identified type A SIV variant (aSIV or a related disease thereto, supra) by Morin et al (Canadian Veterinary Journal, vol. 31 (1990), p. 837) were not observed in Experiment I. The fibrin deposits and hyaline membranes along alveolar septa associated with aSIV (Morin et al, and Girard et al, supra) were not observed. The severe nonsuppurative myocarditis observed in pigs that lived beyond 15 DPI in Experiment I is not associated with aSIV (Morin et al, and Girard et al, supra). Pigs did not seroconvert to SIV, and no SIV was detected by passage in embryonated chicken eggs.

The predominant lung lesion seen in PRRS outbreaks and experimental inoculations is marked interstitial infiltration with mononuclear cells (Collins et al, Pol et al, supra). Type II pneumocyte proliferation, syncytial cell formation, and myocarditis observed in the infected pigs of Experiment I have not been observed by others. The lesions consistently reproduced with the filterable infectious agent of Experiment I suggest that the disease described in this study, which we designate the Iowa strain of PRRSV, is caused by either a unique viral agent or a combination of a PRRS virus with another infectious agent.

EXPERIMENT II (I) Materials and Methods (A) Field Case Material and History

A pig was obtained from a herd which experienced PRRS with persistent severe nursery pneumonia, and had only 20 viable pigs from the last 42 litters farrowed. The pig was necropsied, and samples of lung tissue was collected and homogenized using standard, sterile homogenization techniques. The lung homogenate (10% w/v) prepared in Eagle's minimal essential medium (MEM) and filtered through a 0.22 m$\mu$ filter was used as inoculum.

(B) Cells

A continuous cell line, designated PSP-36, was derived from MA-104 cells, which were purchased from Whittaker Bioproducts, Inc. (Walkersville, Md.). A sample of PSP-36 cells were separately propagated, and this cell line was designated PSP-36-SAH. Swine alveolar macrophages and approximately ninety other cell lines, examples of which are described in Table II hereinbelow were used for virus isolation.

TABLE II

| Porcine | Simian | Canine | Feline | Murine | Human | Hamster |
|---|---|---|---|---|---|---|
| ST-SAH | Vero 76 | NLDK | CRFK | MT | U937 | BHK-21 |
| ST-ATCC | BGM-70 | CK65D | FKCU | P388D1 | Hep 2 | CHO-K1 |
| ST-ISU | BSC-1 | MDCK | FL | IC-21 | | |
| ST-UNE | PSP 36 | CT-60 | NCE | PU5-18 | | |
| PD5 | | | 3201 | L929 | | |
| SLϕ | | | | | | |
| PSP 29 | | | | | | |
| PSP 30 | | | | | | |
| PSP 31 | | | | | | |
| IBRS2D1O | | | | | | |
| AGO8114 | | | | | | |
| AGO8116 | | | | | | |

| Bovine | Invertebrate | Quail | Chicken | Lapine | Bat |
|---|---|---|---|---|---|
| MDBK | ASE | QT-6 | CU10 | RK13 | Tb1Lu |
| | TAE | QT-35 | LMH | | |
| | AVE | | HD11 | | |
| | BGE | | BM2L | | |
| | HZM | | | | |
| | IDE2 | | | | |
| | IDE8 | | | | |
| | RAE | | | | |

(C) Virus Isolation

Lung homogenates prepared as described above were clarified either at 2,000×g or 3,000 rpm at 4° C. for 15 min. The supernatants were filtered through a 0.22 m$\mu$ filter. The filtrates were inoculated onto each of the cell lines described in Section (B) above. Cultures were then maintained in appropriate media with 0–4% fetal bovine serum (FBS) and antibiotics. Cell lines were monitored daily for cytopathic effects (CPE). If CPE was not observed within eight or nine days, the cultures were blindly passed 2–3 times. If suspicious CPE was observed, cultures were examined in an indirect immunofluorescence assay (IFA) using convalescent pig antiserum to ISU-12.

(D) Virus Titration

Serial 10-fold dilutions of ISU-12 isolate were prepared in Dulbecco's minimal essential medium (DMEM) with 2% FBS and 1×antibiotics. Each dilution (0.2 ml) was inoculated in duplicate onto each well of PSP-36 cells and swine alveolar macrophage cultures seeded in Lab-Tek chambers. At three days post infection (DPI), the chambers were fixed with cold 80% acetone and 20% methanol solution at 4° C. for 15 min. The chambers were then stained in an IFA using convalescent ISU-12 antiserum and anti-PRRS virus serum.

(E) Indirect Immunofluorescence Assay (IFA)

The PSP-36 cells and swine alveolar macrophage cultures were infected with ISU-12 isolate. At 20 and 48 hours post infection, the cultures were fixed with cold 80% acetone and 20% methanol solution at 4° C. for 15 min. IFA was carried out using ISU-12 convalescent serum, anti-PRRSV serum and anti-PRRSV monoclonal antibody purchased from South Dakota State University, Brookings, S. Dak. Uninfected PSP-36 cells and macrophage cultures were used as controls.

(F) Radioimmunoprecipitation Assay (RIP)

ISU-12 isolate and mock-infected PSP-36 cells were labelled with $^{35}$S-methionine and $^{35}$S-cysteine. 3-day-old PSP-36 cells in 25 $cm^3$ flasks were infected with 0.5 ml of $10^4$ $TCID_{50}$ of ISU-12 virus. At 24 h post-infection, the medium was replaced with methionine-deficient and cysteine-deficient DMEM, and the cultures were incubated at 37° C. for 1 h. The medium was then replaced with fresh methionine-deficient and cysteine-deficient DMEM with 100 $\mu$ci/ml of the $^{35}$S-methionine ($^{35}$Met) and $^{35}$S-cysteine ($^{35}$Cys). Five hours after addition of $^{35}$Met and $^{35}$Cys, the cells were washed three times with cold phosphate-buffered saline (PBS), pH 7.2, then scraped from the flasks and pelleted by centrifugation at 1,000×g 410 min. The cell pellets containing labelled viral proteins and mock-infected cell pellets were then disrupted with lysis buffer, and the cellular residues were clarified by centrifugation according to the procedure of Zhu et al (*Am. J. Vet. Res.,* 51:232–238 (1990)). The lysates were then incubated with ISU-12 convalescent serum and anti-PRRS virus serum, preabsorbed with cold normal PSP-36 cell lysates at 4° C. overnight. Immune complexes were collected by addition of Sepharose-protein A beads (obtained from Sigma Chemical Co., St. Louis, Mo.) for 2 h at room temperature. The mixture of Sepharose-protein A beads and immune complex were then washed three times with lysis buffer and three times with distilled water. The mixture was resuspended in 50 $\mu$l sample buffer, and run on an SDS-PAGE gel as described by Zhu et al, supra.

(G) Electron Microscopy (EM)

The PSP-36 cells were infected with ISU-12 virus in a 25 $cm^2$ flask. At 48 h post infection, the infected cells were fixed with 3% glutaraldehyde (pH 7.2) at 4° C. for 2 h. The cells were then scraped from the flask and pelleted by centrifugation. The cell pellets were processed and embedded in plastic. The plastic-embedded cell pellets were thin-sectioned, stained and then visualized under a transmission electron microscope as described by Paul et al (*Am. J. Vet. Res.,* 38:311–315 (1976)).

(II) Experimental Reproduction of the Porcine Reproductive and Respiratory Disease (A) Experiment 92.1 SPF Lung filtrate from ISU-12 above was inoculated intranasally into six specific pathogen-free (SPF) pigs that were 5 weeks old. Pigs were killed at 3, 5, 10, 28, and 43 days post inoculation (DPI).

(B) Experiment 92.3 SPF

Six SPF crossbred pigs were inoculated intranasally at 5 weeks of age with porcine alveolar macrophage material infected with ISU-12 lung filtrate. The ISU-12 inoculated pigs were necropsied at 10 and 28 DPI.

(C) Experiment 92.10 SPF

Three 5-week old pigs were inoculated intranasally with 3 ml of ISU-12 propagated on PSP-36, containing $10^5$ $TCID_{50}$/ml of virus. Two pigs served as uninoculated controls. One principal pig was necropsied at 5, 10 and 28 DPI. One control pig was necropsied at each of 5 and 10 DPI.

(D) Experiment 92.12 SPF

Twenty-two 5-week old pigs were divided into six groups. In group I, 6 pigs (principal) were inoculated intranasally with 3 ml of plaque-purified ISU-12 (plaque no. 1) virus propagated on PSP-36 containing $10^5$ $TCID_{50}$/ml of virus. In group II, 6 pigs were inoculated with control cell culture medium. In each of group III (plaque no. 2) and group IV (plaque no. 3), 2 pigs were inoculated with plaque-purified ISU-12. In group V, 3 pigs were inoculated with ISU-12 which was not plaque-purified. In group VI, 3 pigs were inoculated with ISU-12 tissue filtrate.

Two principal and two control pigs were necropsied from each of groups I and II at each of 5, 10 and 25 DPI. Two pigs inoculated with plaques no. 2 and no. 3 were each necropsied at 10 DPI. One pig from each of groups V and VI was necropsied at each of 5, 10 and 25 DPI.

(E) Microscopic Examination

Lung, brain, heart and spleen were collected at necropsy, fixed with 10% neutral buffered formalin, embedded in paraffin, and stained with hematoxylin and eosin.

(III) Results (A) Virus Cultivation (1) Cultivation of ISU-12 Isolate in Swine Alveolar Macrophage Cultures A cytopathic effect (CPE) was observed in swine alveolar macrophage cultures infected with ISU-12 lung filtrate beginning at 2–3 DPI. CPE was characterized by clumping of the macrophages and cell lysis. About 90% of the macrophage cultures in ISU-12 infected cultures were showing CPE by 4–5 DPI. FIG. 12(A) shows that no CPE was observed in uninfected macrophage cultures. The titer of ISU-12 virus in macrophage cultures at third passage was $10^4$–$10^5$ $TCID_{50}$/ml.

Figure 12C:
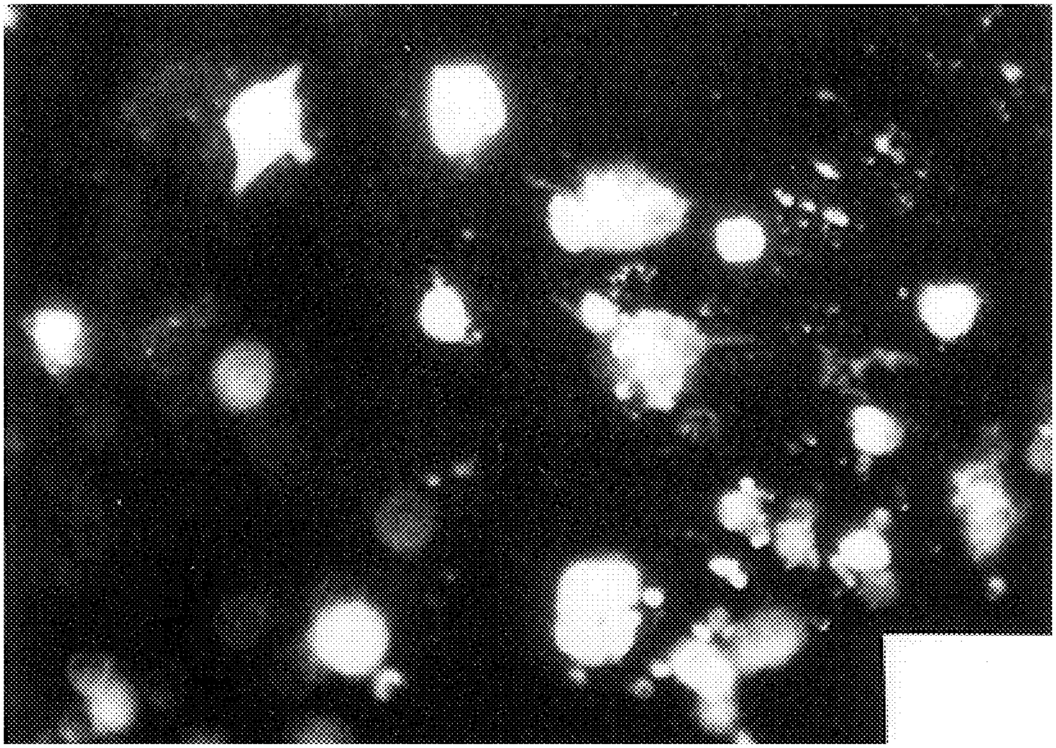

Viral antigens were detected by IFA in the cytoplasm of ISU-12 infected swine alveolar macrophage cultures using ISU-12 convalescent serum from gnotobiotic pigs, as shown in FIG. 12(C). No immunofluorescence was detected in uninoculated macrophage cultures.

(2) Cultivation of ISU-12 Isolate on Continuous Cell Lines

Of the approximately ninety cell lines tested (see Section (B) of "Materials and Methods" above), evidence of viral replication was noted in six cell lines, notably PSP-36, PSP-36-SAH, MA-104, synovial cells, alveolar macrophage cells and porcine turbinate cells.

FIG. 13(B) shows that CPE started at 2 DPI, and was characterized by the degeneration, cell rounding and clumping of cells. At 3–4 DPI, the number of rounded cell clumps increased, and some clumps fused. Many rounded cells detached from the cell monolayer, and led to the subsequent disintegration of the monolayer. After 5 DPI, CPE became quite extensive, and involved over 95% of the monolayer typically. No CPE was observed in control PSP-36 cells, as shown in FIG. 13(A). The ISU-12 isolate grew to high titers on PSP-36 cells, about $10^6$–$10^7$ $TCID_{50}$/ml at the 11th cell culture passage.

Viral antigens were detected in the cytoplasm of infected cells with convalescent sera from gnotobiotic pigs experimentally inoculated with ISU-12 lung filtrate (see FIG. 14(B)). No fluorescence was observed in control PSP-36 cells (FIG. 14(A)).

(III) Virus Characteristics (A) Antigenic Relatedness of ISU-12 to PRRS Virus

Monoclonal antibody to PRRS virus isolate VR-2332 (purchased from Dr. Benfield, South Dakota State University, Brookings, S. Dak.) and anti-PRRSV sera (obtained from the USDA National Veterinary Services Laboratory, Ames, Iowa) reacted with ISU-12-infected PSP-36 cells, evidenced by bright cytoplasmic fluorescence during IFA (see FIG. 14(C)), but did not react with uninfected PSP-36 cells.

(B) Viral Proteins

Figure 15:
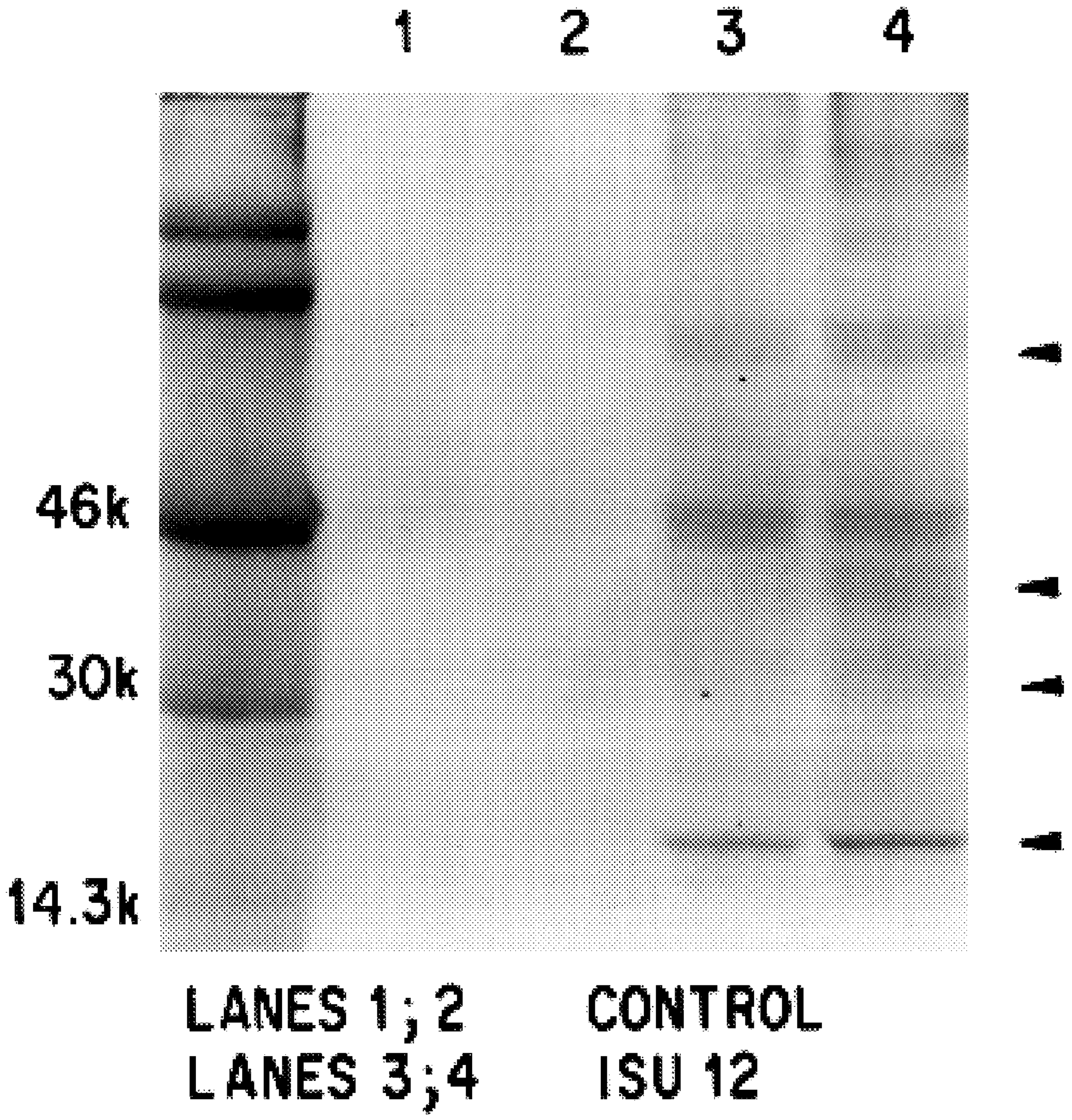
FIG. 15 is a protein profile of ISU-12 propagated in PSP-36 cell line as determined by radioimmunoprecipitation.

Anti-ISU-12 convalescent sera and anti-PRRS virus sera were used to analyze viral proteins. Both sera recognized at least 4 proteins, respectively having molecular weights of 19, 24, 32 and 61 kD (FIG. 15). In FIG. 15, mock infected (lanes 2 and 3) or ISU-12 infected (lanes 4–7) were immunoprecipitated with anti-ISU-12 serum (lanes 2 and 5), anti-PRRSV serum (lanes 3 and 4), anti-PRRSV monoclonal antibody (lane 6) or rabbit anti-PRRSV serum (obtained from Dr. Benfield, South Dakota State University, Brookings, S. Dak.). Lanes 1 and 8 have weight markers. These proteins were not evident in mock-infected PSP-36 cells.

(C) Viral Structure

Typical virus particles ranging from 55–85 nm were observed in ISU-12 infected PSP-36 cells. The virus particles were enveloped, spherical and present in cytoplasmic vesicles of ISU-12 infected PSP-36 cells.

(IV) Experimental Reproduction of Disease (A) Experiment 92.1 SPF

Lung filtrate from ISU-12 above was inoculated intranasally into six specific pathogen-free (SPF) pigs that were 5 weeks old. Pigs were killed at 3, 5, 10, 28, and 43 days post inoculation (DPI). By 3 DPI, the ISU-12 pigs had exhibited severe respiratory distress and pyrexia. These signs persisted for 10–14 days. Gross pulmonary lesions were characterized by severe multifocal grey-tan consolidation of 60% of the lungs. There was also moderate cardiomegaly and accumulation of abdominal fluid. Microscopic changes were characterized by severe proliferative interstitial pneumonia with type II pneumocyte proliferation, syncytial cell formation, alveolar exudation, and mild interstitial thickening with mononuclear cells. There was a mild nonsuppurative myocarditis, a severe encephalitis, and a moderate lymphoplasmacytic nephritis. The ISU-12 experimental pigs necropsied at 10 and 28 days had seroconverted to the PRRS agent as confirmed by NVSL.

(B) Experiment 92.3 SPF

All ISU-12 inoculated SPF pigs exhibited severe respiratory disease within 3 days, persisting for more than 14 days. Gross lesions were characterized by pulmonary congestion, edema and marked multifocal-diffuse hepatization. Microscopically, severe proliferative interstitial pneumonia, moderate nephritis, moderate myocarditis, and mild encephalitis were observed. The ISU-12 inoculated pigs necropsied at 10 and 28 DPI had seroconverted to PRRS as confirmed by NVSL.

(C) Experiment 92.10 SPF

Clinical signs in inoculated pigs included severe lethargy and pyrexia, moderate anorexia, and moderate-to-severe respiratory distress, observed 5–22 DPI. Moderate tearing was present in these pigs throughout the experiment. Microscopic lesions included mild proliferative interstitial pneumonia and severe necropurulent tonsilitis at 5 DPI. Moderate multifocal PIP with type II proliferation, alveolar exudation, multinucleated giant cells, and syncytial cell formation was observed at 10 DPI. Moderate multifocal encephalitis with perivascular cuffs and gliosis was also observed at 10 DPI. Mild periportal lymphomacrophagic hepatitis, mild nonsuppurative myocarditis and rhinitis was detected at 10 DPI. At 26 DPI, there was severe interstitial pneumonia, characterized by marked multifocal interstitial thickening with mononuclear cells, moderate multifocal type II pneumocyte proliferation, moderate amounts of mixed alveolar exudate, and loose peribronchiolar cuffs of lymphocytes and macrophages. There was also a moderate multifocal myocarditis, a mild hepatitis, a mild nephritis and tonsilitis. The two ISU-12 inoculated pigs seroconverted to PRRS at 10 DPI.

The control pigs remained clinically normal during the duration of the experiment, and exhibited neither gross nor microscopic lesions. They also remained seronegative for PRRS.

(D) Experiment 92.12 SPF

The biologically uncloned ISU-12 was pathogenic for SPF pigs, and produced interstitial pneumonia, myocarditis and encephalitis, as described above for Experiment 92.10 SPF. Pigs inoculated with the three biological clones of ISU-12 (plaques nos. 1, 2 and 3) produced mild interstitial pneumonia, but evidence of type II pneumocyte proliferation, alveolar exudation, myocarditis and/or encephalitis were not detected in these pigs. All pigs inoculated with ISU-12, either cloned or uncloned, seroconverted to PRRS at 10 DPI. The control pigs remained free of virus infection and disease.

(V) Summary

Severe pneumonia was experimentally reproduced in five-week-old SPF pigs with lung and heart filtrates (0.22 m$\mu$) from naturally-affected pigs (ISU-12). The pneumonia produced by the Iowa strain of PRRSV (ISU-12) is characterized by interstitial pneumonia, type II pneumocyte proliferation, and syncytial cell formation. Myocarditis and encephalitis are observed in affected pigs. ISU-12 produced cytopathic effects (CPE) in swine alveolar macrophage cultures and a continuous cell line, PSP-36. Viral antigens were detected by indirect immunofluorescence in ISU-12-infected cultures but not in uninfected cells. ISU-12 is antigenically related to PRRS virus strain VR-2332 by indirect immunofluorescence using polyclonal and monoclonal antibodies. However, differences were observed in microscopic lesions of the pigs infected with non-plaque-purified ISU-12, thus indicating that another virus or infectious agent may be grown in PSP-36, and that the other virus or infectious agent may be the reason that the disease and lesions caused by the Iowa strain of PRRSV is different from and more severe than that reported for PRRS virus in the literature. All pigs inoculated with ISU-12, either cloned or uncloned, seroconverted to PRRS at 10 DPI. The control pigs remained free of virus infection and disease.

Experiment III

Molecular Cloning and Nucleotide Sequencing of the 3'-Terminal Region of the Infectious Agent Associated With the Iowa Strain of Porcine Respiratory and Reproductive Syndrome (I) Materials and Methods (A) Virus Propagation and Purification Hereinafter, to simplify the discussion, the terms "virus" and "viral" will refer to a virus or infectious agent in the meaning described above for the present application, or a property of the virus or infectious agent.

A continuous cell line, PSP-36, was used to isolate and propagate ISU-12 isolate, associated with the Iowa strain of PRRSV. The ISU-12 virus was plaque-purified 3 times on PSP-36 cells. The PSP-36 cells were then infected with the plaque-purified virus. When more than 70% of the infected cells showed cytopathic changes, the culture was frozen and thawed three times. The culture medium was then clarified by low-speed centrifugation at 5,000×g for 15 min. at 4° C. The virus was then precipitated with 7% PEG-8000 and 2.3% NaCl at 4° C. overnight with stirring, and the precipitate was pelleted by centrifugation. The virus pellets were then resuspended in 2 ml of tris-EDTA buffer, and layered on top of a CsCl gradient (1.1245–1.2858 g/ml). After ultracentrifugation at 28,000 rpm for about 8 hours at 20° C., a clear band with a density of 1.15–1.18 g/ml was observed and harvested. The infectivity titer of this band was determined by IFA, and the titer was found to be $10^6$ $TCID_{50}$/ml. Typical virus particles were also observed by negative staining electron microscopy (EM).

(B) Isolation of Viral RNA

Total RNA was isolated from the virus-containing band in the CsCl gradient with a commercially available RNA isolation kit (obtained from Stratagene). Poly(A) RNA was then enriched by oligo (dT)-cellulose column chromatography according to the procedure described by the manufacturer of the column (Invitrogen).

(C) Construction of ISU-12 cDNA λ Library

Figure 16:
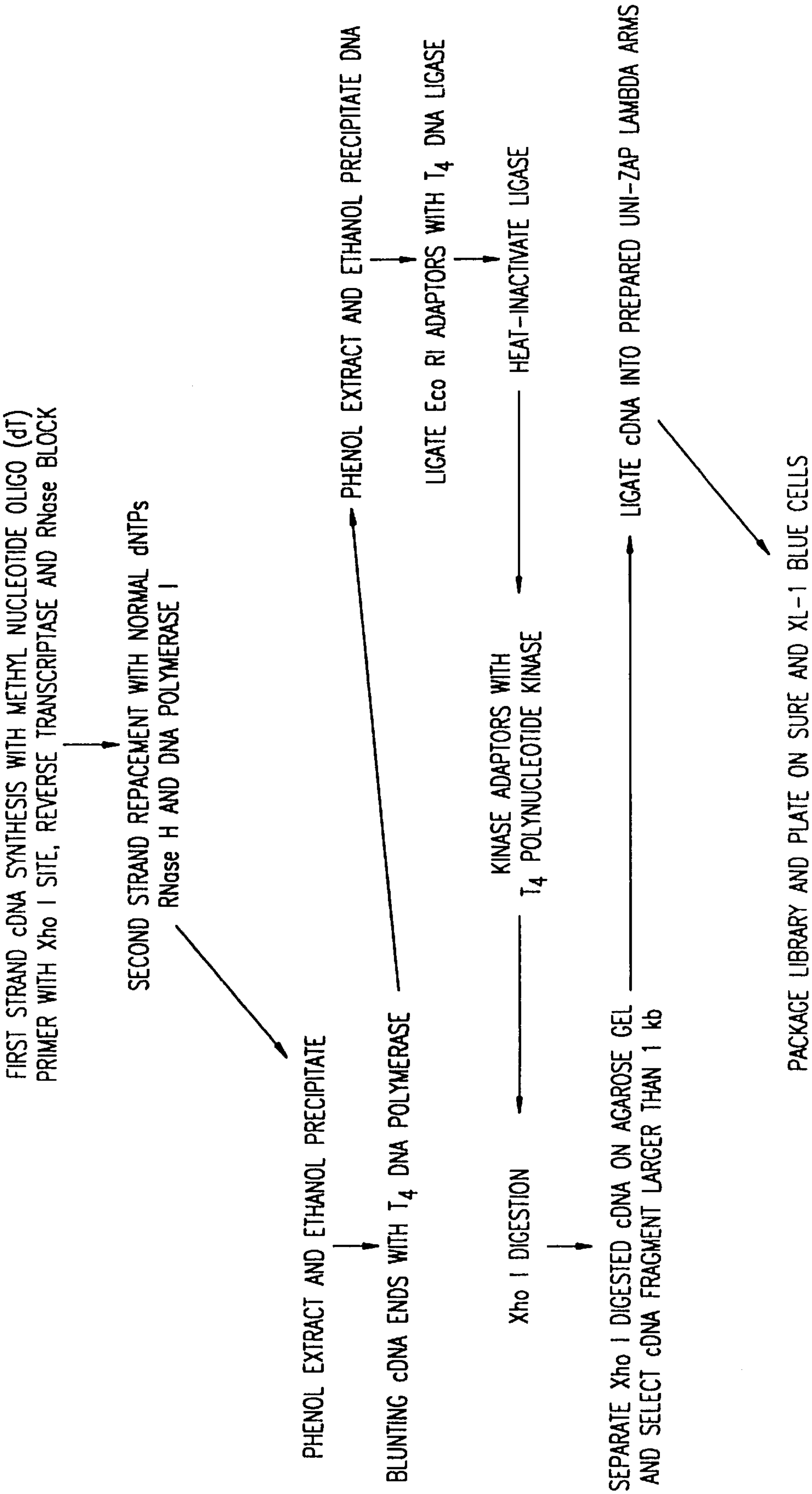
FIG. 16 shows a general procedure for construction of a cDNA λ library of a strain of infectious agent causing PRRS.

A general schematic procedure for the construction of a cDNA λ library is shown in FIG. 16. First strand cDNA synthesis from mRNA was conducted by reverse transcription using an oligo (dT) primer having a Xho I restriction site. The nucleotide mixture contained normal dATP, dGTP, dTTP and the analog 5-methyl dCTP, which protects the cDNA from restriction enzymes used in subsequent cloning steps.

Second strand cDNA synthesis was then conducted with RNase H and DNA polymerase I. The cDNA termini were blunted (blunt-ended) with T4 DNA polymerase, ligated to EcoR I adaptors with T4 DNA ligase, and subsequently kinased (i.e., phosphorylated) with T4 polynucleotide kinase. The cDNA was digested with Xho I, and the digested cDNA were size-selected on an agarose gel. Digested cDNA larger than 1 kb in size were selected and purified by a commercially available DNA purification kit (GENECLEAN, available from BIO 101, Inc., La Jolla, Calif.).

The purified cDNA was then ligated into lambda phage vector arms, engineered with Xho I and EcoR I cohesive ends. The ligated vector was packaged into infectious lambda phages with lambda extracts. The SURE strain (available from Stratagene) of *E. coli* cells were used for transfection, and the lambda library was then amplified and titrated in the XL-1 blue cell strain.

(D) Screening the λ Library by Differential Hybridization

Figure 17:
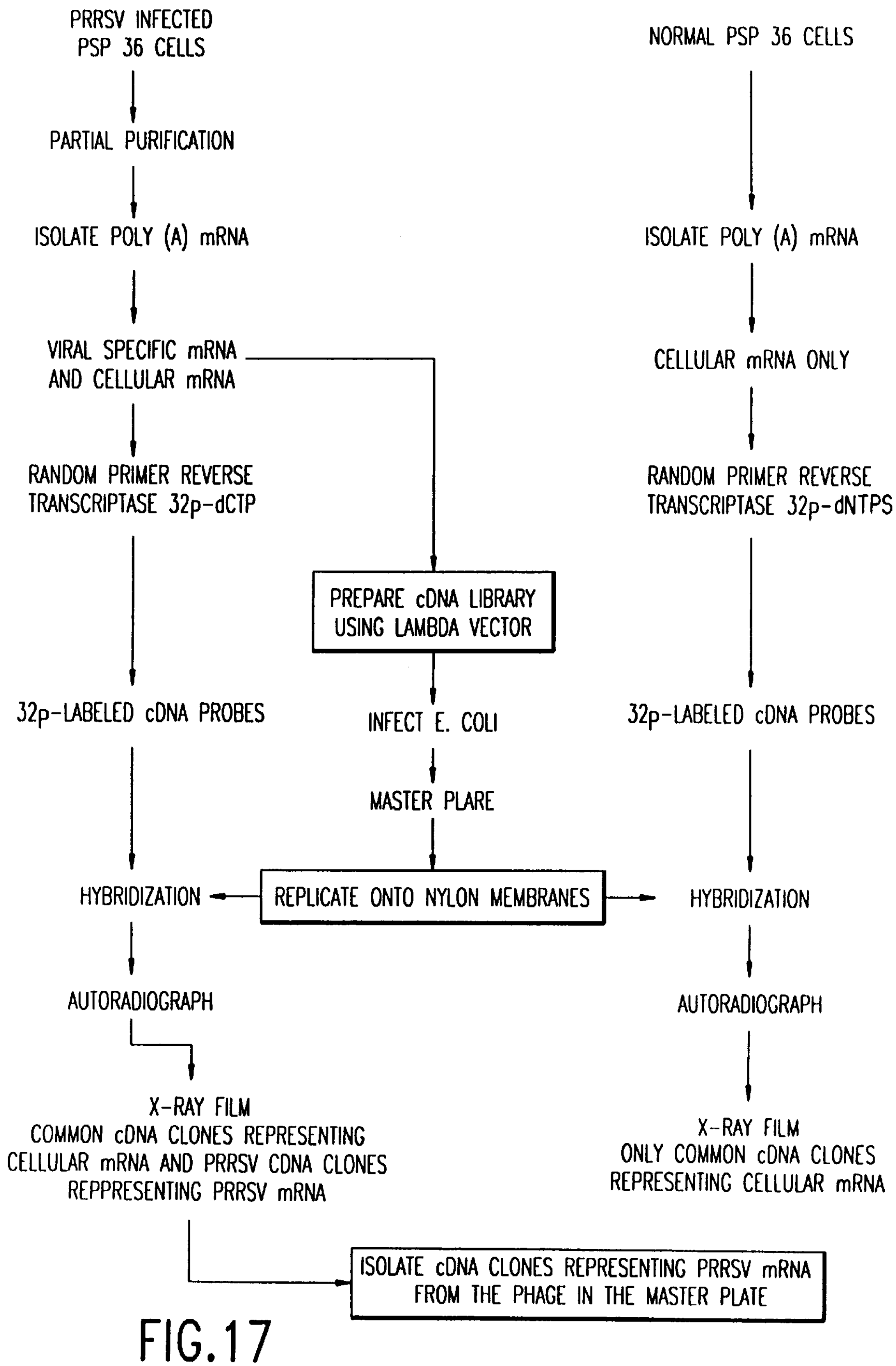
FIG. 17 shows a general procedure for the identification of authentic clones of the infectious agent associated with the Iowa strain of PRRSV by differential hybridization.

A general schematic procedure for identifying authentic clones of the PIP virus ISU-12 strain by differential hybridization is shown in FIG. 17, and is described hereunder. The λ library was plated on XL-1 blue cells, plaques were lifted onto nylon membranes in duplicates, and denatured with 0.5 N NaOH by conventional methodology. Messenger RNA's from both virus-infected PSP-36 cells and non-infected PSP-36 cells were isolated by oligo (dT)cellulose column chromatography as described by the manufacturer of the column (Invitrogen).

Complementary DNA probes were synthesized from mRNA's isolated from virus-infected PSP-36 cells and normal PSP-36 cells using random primers in the presence of $^{32}$P-dCTP according to the procedure described by the manufacturer (Amersham). Two probes (the first synthesized from virus-infected PSP-36 cells, the other from normal, uninfected PSP-36 cells) were then purified individually by Sephadex G-50 column chromatography. The probes were hybridized with the duplicated nylon membranes, respectively, at 42° C. in 50% formamide. Plaques which hybridized with the probe prepared from virus infected cells, but not with the probe prepared from normal cells, were isolated. The phagemids containing viral cDNA inserts were rescued by in vitro excision with the help of G408 helper phage. The rescued phagemids were then amplified on XL-1 blue cells. The plasmids containing viral cDNA inserts were isolated by Qiagen column chromatography, and were subsequently sequenced.

(E) Nucleotide Sequencing and Sequence Analysis

Plasmids containing viral cDNA inserts were purified by Qiagen column chromatography, and sequenced by Sanger's dideoxy method with universal and reverse primers, as well as a variety of internal oligonucleotide primers. Sequences were obtained from at least three separate clones. Additional clones or regions were sequenced when ambiguous sequence data were obtained. The nucleotide sequence data were assembled and analyzed independently using two computer software programs, GENEWORKS (IntelliGenetics, Inc., Mountain View, Calif.) and MACVECTOR (International Biotechnologies, Inc., New Haven, Conn.).

(F) Oligonucleotide Primers

Oligonucleotides were synthesized as single-stranded DNA using an automated DNA synthesizer (Applied Biosystems) and purified by HPLC. Oligonucleotides PP284 (5-CGGCCGTGTG GTTCTCGCCA AT-3'; SEQ ID NO:1) and PP285 (5-CCCCATTTCC CTCTAGCGAC TG-3'; SEQ ID NO:2) were synthesized for PCR amplification. A DNA probe was generated with these two primers from the extreme 3' end of the viral genome for Northern blot analysis (see discussion below). Oligonucleotides PP286 (5'-GCCGCGGAAC CATCAAGCAC-3'; SEQ ID NO:3) and PP287 (5'-CAACTTGACG CTATGTGAGC-3'; SEQ ID NO:4) were synthesized for PCR amplification. A DNA probe generated by these two primers was used to further screen the λ library. Oligonucleotides PP288 (5'-GCGGTCTGGA TTGACGACAG-3'; SEQ ID NO:5), PP289 (5'-GACTGCTAGG GCTTCTGCAC-3'; SEQ ID NO:6), PP386 (5'-GCCATTCAGC TCACATAGCG-3'; SEQ ID NO:7), PP286 and PP287 were used as sequencing primers to obtain internal sequences.

(G) Northern Blot Analysis

A specific DNA fragment from the extreme 3' end of the ISU-12 cDNA clone was amplified by PCR with primers PP284 and PP285. The DNA fragment was excised from an agarose gel with a commercially available DNA purification kit (GENECLEAN, obtained from Bio 101), and labeled with $^{32}$P-dCTP by random primer extension (using a kit available from Amersham). Total RNA was isolated from ISU-12-infected PSP-36 cells at 36 hours post-infection, using a commercially available kit for isolation of total RNA according to the procedure described by the manufacturer (Stratagene). ISU-12 subgenomic mRNA species were denatured with 6 M glyoxal and DMSO, and separated on a 1% agarose gel. (Results from a similar procedure substituting a 1.5% agarose gel are described in Experiment VIII below and shown in FIG. 32.) The separated subgenomic mRNA's were then transferred onto nylon membranes using a POSIBLOT™ pressure blotter (Stratagene). Hybridization was carried out in a hybridization oven with roller bottles at 42° C. and 50% formamide.

Results (A) Cloning, Identification and Sequencing of ISU-12 3' Terminal Genome

An oligo (dT)-primed cDNA λ library was constructed from a partially purified virus, obtained from ISU-12 -infected PSP-36 cells. Problems were encountered in screening the cDNA λ library with probes based on the Lelystad virus sequence. Three sets of primers were prepared. The first set (PP105 and PP106; SEQ ID NOS:18–19) correspond to positions 14577 to 14596 and 14977 to 14995 of the Lelystad genomic sequence, located in the nucleocapsid gene region. The second set (PP106 and PP107, SEQ ID NOS:19–20) correspond to positions 14977 to 14995 and 14054 to 14072 of the Lelystad genomic sequence, flanking ORF's 6 and 7. The third set (PM541 and PM542; SEQ ID NOS:21–22) correspond to positions 11718 to 11737 and 11394 to 11413 of the Lelystad genomic sequence, located in the ORF-1b region.

PP105: 5'-CTCGTCAAGT ATGGCCGGT-3' (SEQ ID NO:18)

PP106: 5'-GCCATTCGCC TGACTGTCA-3' (SEQ ID NO:19)

PP107: 5'-TTGACGAGGA CTTCGGCTG-3' (SEQ ID NO:20)

PM541: 5'-GCTCTACCTG CAATTCTGTG-3' (SEQ ID NO:21)

PM542: 5'-GTGTATAGGA CCGGCAACCG-3' (SEQ ID NO:22)

All attempts to generate probes by PCR from the ISU-12 infectious agent using these three sets of primers were unsuccessful. After several attempts using the differential hybridization technique, however, the authentic plaques representing ISU-12-specific cDNA were isolated using probes prepared from ISU-12-infected PSP-36 cells and normal PSP-36 cells. The procedures involved in differential hybridization are described and set forth in FIG. 17.

Figure 18:
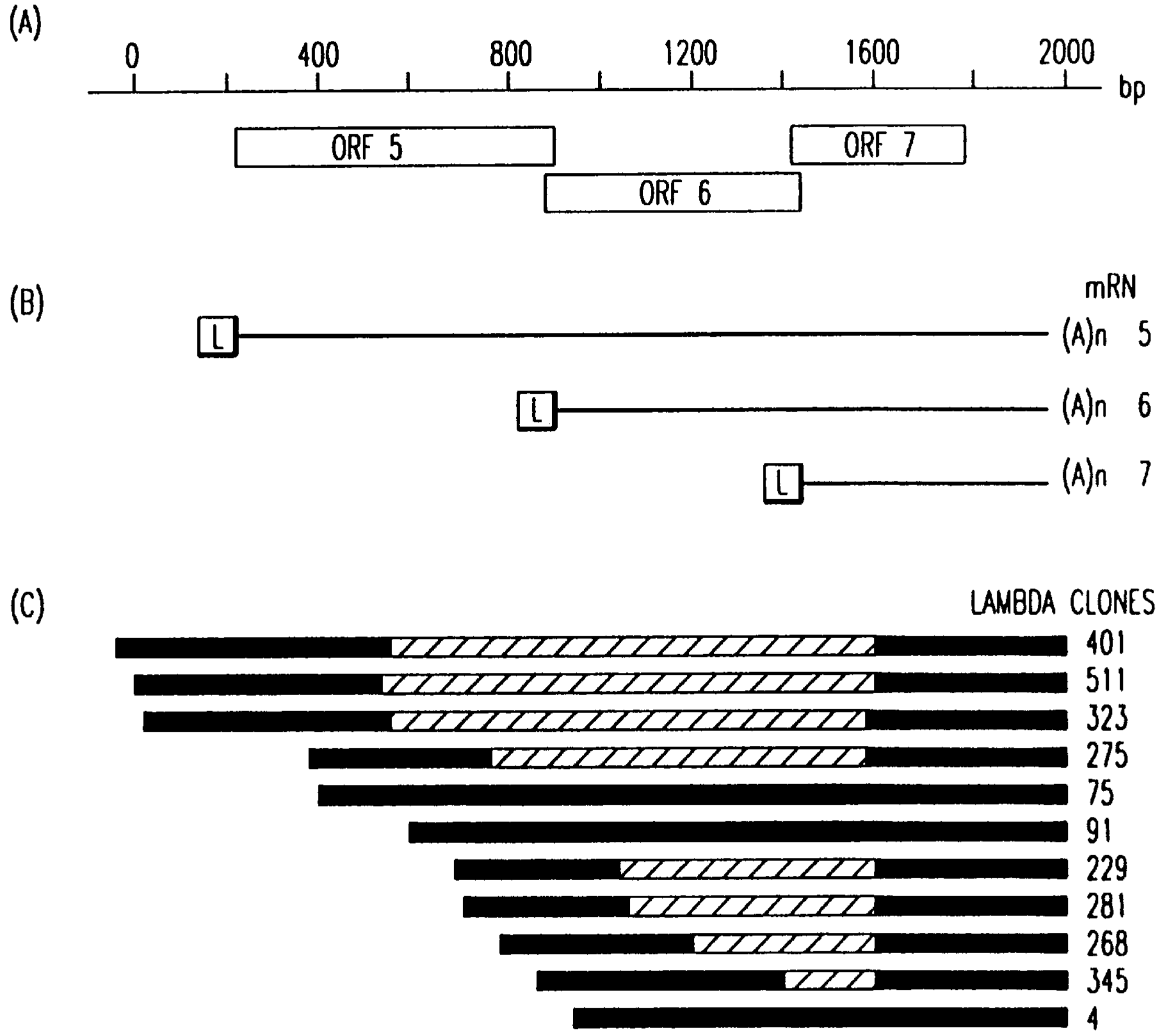
FIG. 18 shows the construction of λ cDNA clones used to obtain the 3'-terminal nucleotide sequence of the infectious agent associated with the Iowa strain of PRRSV.

Three positive plaques (λ-4, λ-75 and λ-91) were initially identified. Phagemids containing viral cDNA inserts within the λ phage were rescued by in vitro excision with the help of G408 helper phages. The inserts of the positive clones were analyzed by restriction enzyme digestion and terminal sequencing. The specificity of the cDNA clones was further confirmed by hybridization with RNA from PSP-36 cells infected with the Iowa strain of PRRSV, but not with RNA from normal PSP-36 cells. A DNA probe was then generated from the 5'-end of clone λ-75 by PCR with primers PP286 and PP287. Further positive plaques (λ-229, λ-268, λ-275, λ-281, λ-323 and λ-345) were identified using this probe. All λ cDNA clones used to obtain the 3'-terminal nucleotide sequences are presented in FIG. 18. At least three separate clones were sequenced to eliminate any mistakes. In the case of any ambiguous sequence data, additional clones and internal primers (PP288, PP289, PP286, PP287 and PP386) were used to determine the sequence. The 1938-bp 3'-terminal sequence (SEQ ID NO:8) is presented in FIG. 19, and the deduced amino acid sequence (SEQ ID NO:9) is presented in FIG. 20.

(B) A Nested Set of Subgenomic mRNA

Total RNA from virus-infected PSP-36 cells was separated on 1% glyoxal/DMSO agarose gel, and blotted onto nylon membranes. A cDNA probe was generated by PCR with a set of primers (PP284 and PP285) flanking the extreme 3'-terminal region of the viral genome. The probe contains a 3'-nontranslational sequence and most of the ORF-7 sequence. Northern blot hybridization results show that the pattern of mRNA species from PSP-36 cells infected with the Iowa strain of PRRSV is very similar to that of Lelystad virus (LV), equine arteritis virus (EAV), lactate dehydrogenase-elevating virus (LDV) and coronavirus, in that virus replication required the formation of subgenomic mRNA's.

The results also indicate that ISU-12-specific subgenomic mRNA's represent a 3'-nested set of mRNA's, because the Northern blot probe represents only the extreme 3' terminal sequence. The size of ISU-12 viral genomic RNA (14 kb) and 6 subgenomic mRNA's (RNA 2 (3.0 kb), RNA 3 (2.5 kb), RNA 4 (2.2 kb), RNA 5 (1.8 kb), RNA 6 (1.3 kb) and RNA 7 (0.98 kb)) resemble those of LV (FIG. 18), although there are differences in both the genome and in subgenomic RNA species. Differences were also observed in the relative amounts of the subgenomic mRNA's, RNA 7 being the most predominant subgenomic mRNA.

(C) Analysis of Open Reading Frames Encoded by Subgenomic RNA

Three large ORF's have been found in SEQ ID NO:8: ORF-5 (nt 239–901; SEQ ID NO:10), ORF 6 (nt 889–1403; SEQ ID NO:12) and ORF 7 (nt 1403–1771; SEQ ID NO:15). ORF 4, located at the 5' end of the resulting sequence, is incomplete in the 1938-bp 3'-terminal sequence of SEQ ID NO:8. ORF'S 5, 6 AND 7 each have a coding capacity of more than 100 amino acids. ORF 5 and ORF 6 overlap each other by 10 bp, and ORF 6 and ORF 7 overlap each other by 5 bp. Two smaller ORF's located entirely within ORF 7 have also been found, coding for only 37 aa and 43 aa, respectively. Another two short ORF's overlap fully with ORF 5. The coding capacity of these two ORF's is only 29 aa and 44 aa, respectively. No specific subgenomic mRNA's were correlated to these smaller ORF's by Northern Blot analysis. ORF 6 and ORF 7 are believed to encode the viral membrane protein and capsid protein, respectively.

(D) Consensus Sequence for Leader Junction

Sequence analysis shows that a short sequence motif, AACC, may serve as the site in the subgenomic mRNA's where the leader is added during transcription (the junction site). The junction site of ORF 6 is found 21 bp upstream from the ATG start codon, and the junction site of ORF 7 is found 13 bp upstream from the ATG start codon, respectively. No AACC consensus sequence has been identified in ORF 5, although it has been found in ORF 5 of LV. Similar junction sequences have been found in LDV and EAV.

(E) 3'-Nontranslational Sequence and Poly (A) Tail

A 150 nucleotide-long (150 nt) nontranslational sequence following the stop codon of ORF 7 has been identified in the genome of the ISU-12 virus, compared to 114 nt in LV, 80 nt in LDV and 59 nt in EAV. The length of the poly (A) tail is at least 13 nucleotides. There is a consensus sequence, CCGG/AAATT-poly (A) among PIP virus ISU-12, LV and LDV in the region adjacent to the poly (A) tail.

(F) Sequence Comparison of ISU-12 and LV Genomes Among ORF's 5, 6 and 7, and Among the Nontranslational Sequences A comparison of the ORF-5 regions of the genomes of ISU-12 and of the Lelystad viruses is shown in FIG. 21. The corresponding comparisons of the ORF-6 region, the ORF-7 region, and the nontranslational sequences are respectively shown in FIGS. 22, 23 and 24.

The results of the comparison are presented in Table III below. Consistent with the description above, a virus is considered immunologically equivalent if it has 90% or greater homology with an immunogenic virus. The nucleotide sequence homologies between LV and ISU-12 of the ORF 5, ORF 6, ORF 7 and the nontranslational sequences are 60%, 68%, 60% and 58%, respectively. Accordingly, LV and ISU-12 are not immunogenic equivalents.

The size of ORF's 5 and 6 in LV is 61 nt and 3 nt smaller than ORF's 5 and 6 in ISU-12, respectively. In contrast, the size of ORF 7 in LV is 15 nt larger than that in ISU-12. Also, the 3'-terminal nontranslational sequence is different in length (150 nt in ISU-12, but only 114 nt in LV). Like LV, the junction sequence, AACC, has also been identified in the genome of the Ioaw strain of PRRS virus isolate ISU-12, except for ORF 5. The junction sequence ot ORF 6 in ISU-12 is 21 nt upstream from the ATG start codon, whereas the junction sequence of ORF 6 is 28 nt upstream from ATG in LV.

TABLE III

| Characteristics of the ORFs and Nontranslational Sequence of Lelystad Virus and ISU-12 | | | | | |
|---|---|---|---|---|---|
| | Lelystad Virus | | | PRRSV ISU-12 | |
| | Size (bp) | Junction Seq. (nt from ATG) | Sequence Homology (%) | Size (bp) | Junction Seq. (nt from ATG) |
| ORF-5 | 605 | AACC (ATG-36) | 60 | 666 | No ? |
| ORF-6 (Env) | 521 | AACC (ATG-28) | 68 | 525 | AACC (ATG-21) |
| ORF-7 (NP) | 386 | AACC (ATG-13) | 60 | 371 | AACC (ATG-13) |
| NT | 113 | | 58 | 150 | |

Experiment IV

Expression of Iowa Strain Infectious Agent Genes in Insect Cells (A) Production of Recombinant Baculovirus The ORF-5, ORF-6 and ORF-7 sequences were individually amplified by PCR using primers based on the ISU-12 genomic nucleotide sequence. ORF-5 was amplified using the following primers:

5'-GGGGATCCGG TATTTGGCAA TGTGTC-3' (SEQ ID NO:23)

3'-GGGAATTCGC CAAGAGCACC TTTTGTGG-5' (SEQ ID NO:24)

ORF-6 was amplified using the following primers:

5'-GGGGATCCAG AGTTTCAGCG G-3' (SEQ ID NO:25)

3'-GGGAATTCTG GCACAGCTGA TTGAC-5' (SEQ ID NO:26)

ORF-7 was amplified using the following primers:

5'-GGGGATCCTT GTTAAATATG CC-3' (SEQ ID NO:27)

3'-GGGAATTCAC CACGCATTC-5' (SEQ ID NO:28)

The amplified DNA fragments were cloned into baculovirus transfer vector pVL1393 (available from Invitrogen). One $\mu$g of linearized baculovirus AcMNPV DNA (commercially available from Pharmingen, San Diego, Calif.) and 2 $\mu$g of PCR-amplified cloned cDNA-containing vector constructs were mixed with 50 $\mu$l of lipofectin (Gibco), and incubated at 22° C. for 15 min. to prepare a transfection mixture.

One hour after seeding HI-FIVE cells, the medium was replaced with fresh Excell 400 insect cell culture medium (available from JR Scientific Co.), and the transfection mixture was added drop by drop. The resulting mixture was incubated at 28° C. for six hours. Afterwards, the transfection medium was removed, and fresh Excell 400 insect cell culture medium was added. The resulting mixture was then incubated at 28° C.

Five days after transfection, the culture medium was collected and clarified. Ten-fold dilutions of supernatants were inoculated onto HI-FIVE cells, and incubated for 60 min. at room temperature. After the inoculum was discarded, an overlay of 1.25% of agarose was applied onto the cells. Incubation at 28° C. was conducted for four days. Thereafter, clear plaques were selected and picked using a sterile Pasteur pipette. Each plaque was mixed with 1 ml of Grace's insect medium into a 5 ml snap cap tube, and placed in a refrigerator overnight to release the virus from the agarose. Tubes were centrifuged for 30 minutes at 2000×g to remove agarose, and the supernatants were transferred into new sterile tubes. Plaque purification steps were repeated three times to avoid possible wild-type virus contamination. Pure recombinant clones were stored at −80° C. for further investigation.

(B) Expression of Recombinant Iowa Strain Infectious Agent Proteins

Indirect immunofluorescence assay and radioimmunoprecipitation tests were used to evaluate expression.

Figure 25:
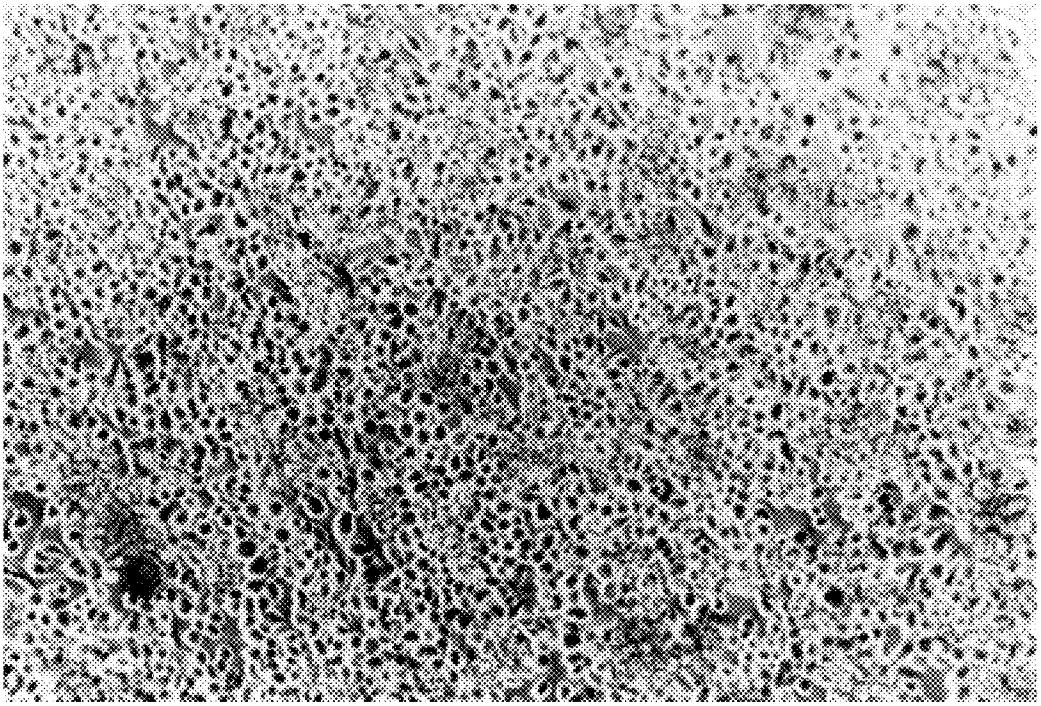
FIG. 25 shows HI-FIVE cells infected with a recombinant baculovirus containing the ISU-12 ORF-7 gene, also exhibiting a cytopathic effect.
Figure 26:
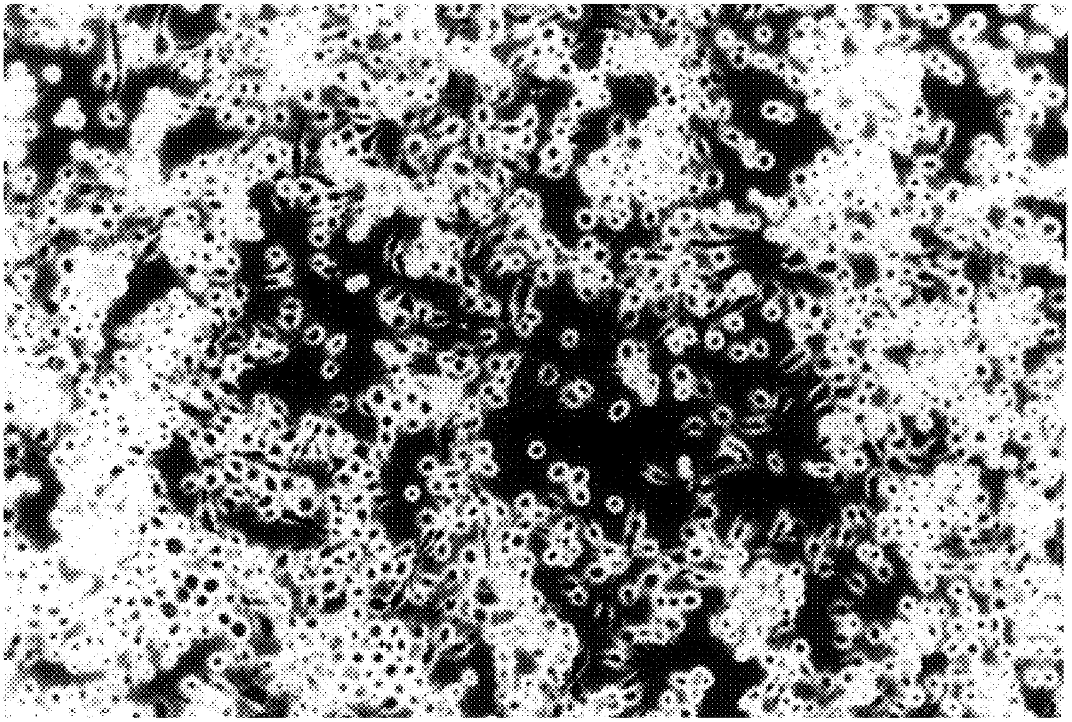
FIG. 26 shows HI-FIVE cells infected with a recombinant baculovirus containing the ISU-12 ORF-6 gene, stained with swine antisera to ISU-12, followed by staining with fluorescein-conjugated anti-swine IgG, in which the insect cells are producing a recombinant protein encoded by the ISU-12 ORF-6 gene.
Figure 27:
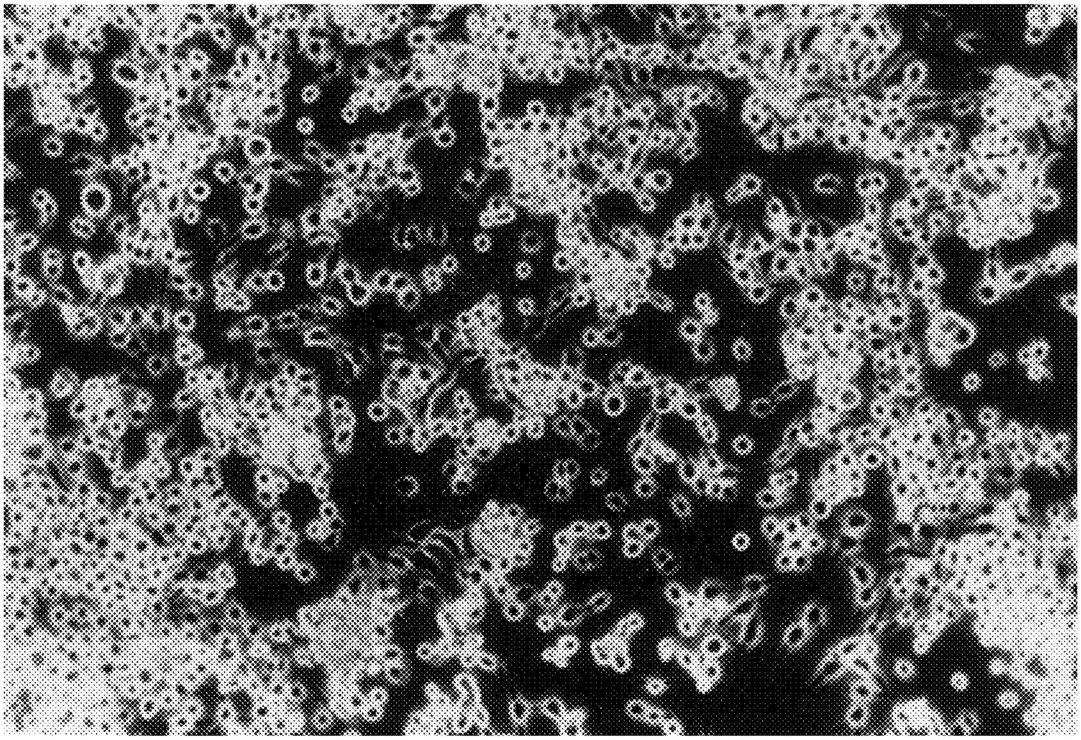
FIG. 27 shows HI-FIVE cells infected with a recombinant baculovirus containing the ISU-12 ORF-7 gene, stained with swine antisera to ISU-12, followed by staining with fluorescein-conjugated anti-swine IgG, in which the insect cells are producing recombinant protein encoded by the ISU-12 ORF-7 gene.

Indirect immunofluorescence assay: Hi-five insect cells, in a 24-well cell culture cluster plate were infected with wild-type baculovirus or recombinant baculovirus, or were mock-infected. After 72 hours, cells were fixed and stained with appropriate dilutions of swine anti-ISU-12 polyclonal antibodies, followed by fluorescein isothiocyanate-labelled (FITC-labelled) anti-swine IgG. As shown in FIGS. 25–27, immunofluorescence was detected in cells infected with the recombinant viruses, but not in mock-infected cells or cells inoculated with wild-type baculovirus. For example, FIG. 26 shows HI-FIVE cells infected with the recombinant baculovirus containing the ISU-12 ORF-6 gene (Baculo.PRRSV.6), which exhibit a cytopathic effect. FIG. 25 shows HI-FIVE cells infected with another recombinant baculovirus containing the ISU-12 ORF-7 gene (Baculo.PRRSV.7), which also exhibit a cytopathic effect. Similar results were obtained with recombinant baculovirus containing ORF-5 (Baculo.PRRSV.5, data not shown). FIGS. 26 and 27 show HI-FIVE cells infected with a recombinant baculovirus containing the ISU-12 ORF-6 gene and ISU-12 ORF-7 gene, respectively, stained with swine antisera to ISU-12, followed by fluorescein-conjugated anti-swine IgG, in which the insect cells are producing recombinant Iowa strain infectious agent protein. Similar results were obtained with recombinant baculovirus containing ORF-5.

Figure 28:
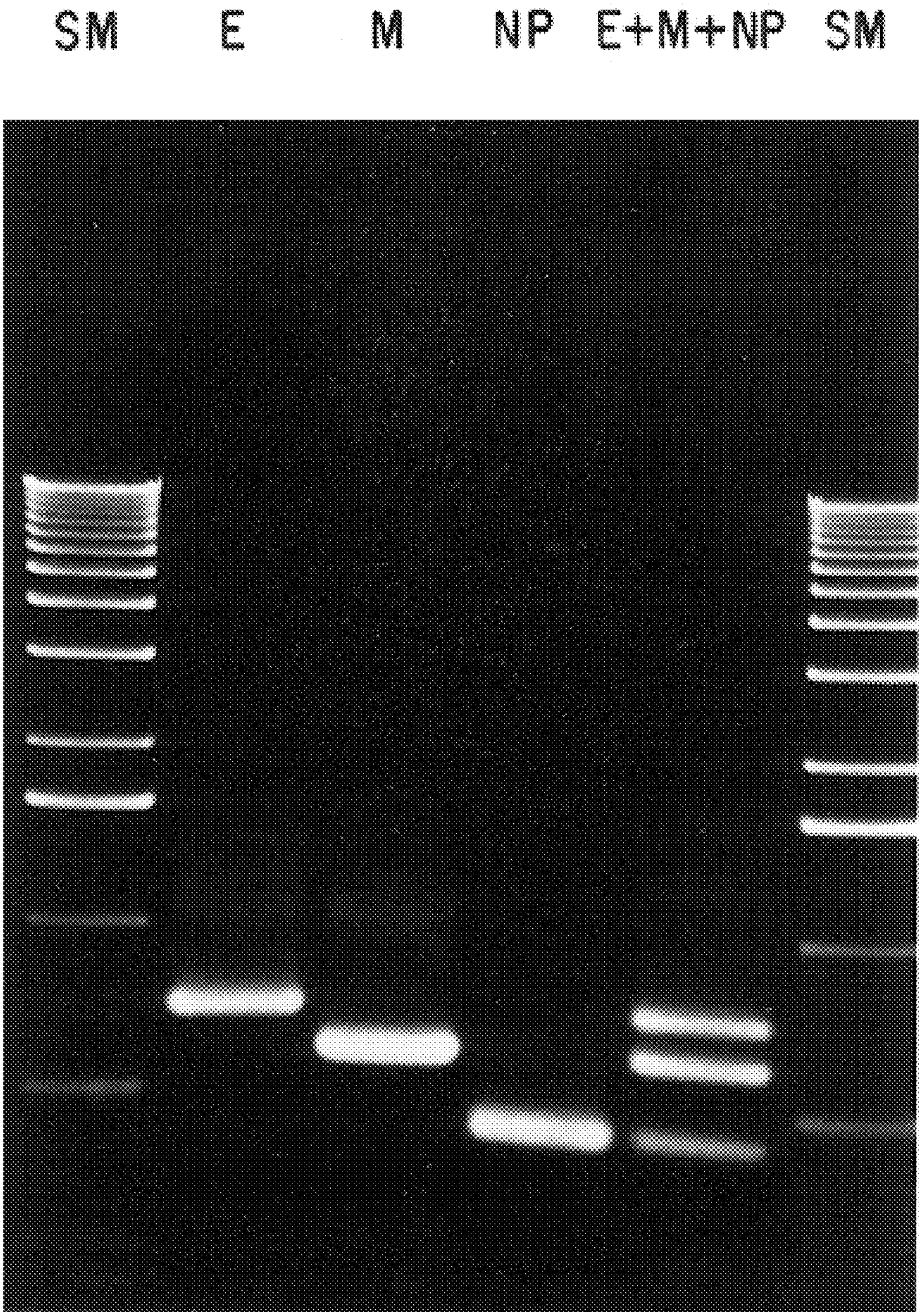
FIG. 28 shows the results of PCR amplification of ORF-5 (lane E), ORF-6 (lane M) and ORF-7 (lane NP) using ISU-12 specific primers, in which lane SM contains molecular weight standards.
Figure 29:
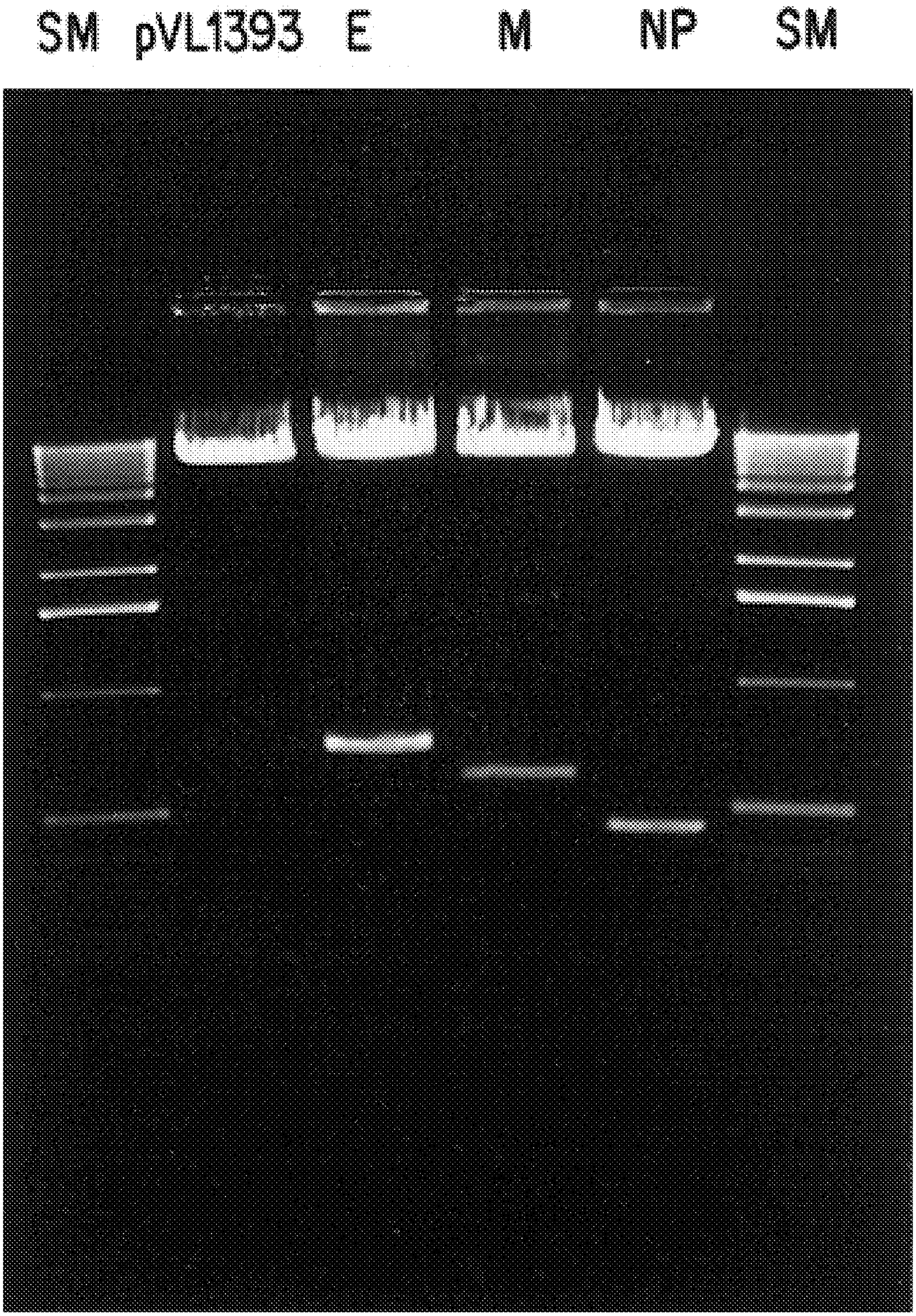
FIG. 29 shows the results of expressing recombinant baculovirus transfer vector pVL1393, containing ORF-5 (lane E), ORF-6 (lane M) or ORF-7 (lane NP) of the genome of ISU-12, after cleaving plasmid DNA with BamHI and EcoRI restriction enzymes; lane SM contains molecular weight standards.

Radioimmunoprecipitation: Radioimmunoprecipitation was carried out with each recombinant virus (Baculo.PRRSV.5, Baculo.PRRSV.6 and Baculo.PRRSV.7) to further determine the antigenicity and authenticity of the recombinant proteins. HI-FIVE insect cells were mock-infected, or alternatively, infected with each of the recombinant baculoviruses. Two days after infection, methionine-free medium was added. Each mixture was incubated for two hours, and then proteins labeled with $^{35}$S-methionine (Amersham) were added, and the mixture was incubated for four additional hours at 28° C. Radiolabeled cell lysates were prepared by three cycles of freezing and thawing, and the cell lysates were incubated with preimmune or immune anti-ISU-12 antisera. The immune complexes were precipitated with Protein A agarose and analyzed on SDS-PAGE after boiling. X-ray film was exposed to the gels at −80° C., and developed. Bands of expected size were detected with ORF-6 (FIG. 28) and ORF-7 (FIG. 29) products.

Experiment V

Other samples of PRRSV, described in Table 4 below, were plaque-purified three times. Plaque purification was performed by culturing a clarified tissue homogenate on PSP-36-SAH cells and selecting a single plaque, assuming one plaque is produced by a single virus. The selected plaque was then cultured, and a single plaque was again selected, then cultured a third time. IFA was carried out using anti-PRRSV monoclonal antibody purchased from South Dakota State University, Brookings, S. Dak.

Some isolated samples selected for further study are identified in Table 5 below, and are characterized by their pathogenicity and number of mRNA's.

TABLE 4

PRRSV 3 X PLAQUE-PURIFIED ISOLATES

| PRRSV ISOLATE | DATE FROZEN STOCK PREPARED | PRRS MONOCLONAL IFA RESULT | TITER $TCID_{50}$/ml |
|---|---|---|---|
| ISU-22 | 9/15/92 | + | $10^{5.57}$ ± 0.15 |
| ISU-28 | 9/15/92 | + | $10^{5.14}$ ± 0.28 |
| ISU-12 | 9/17/92 | + | $10^{4.33}$ ± 0.21 |
| ISU-3927 | 9/21/92 | + | $10^{3.56}$ ± 0.17 |
| ISU-984 | 9/21/92 | + | $10^{3.89}$ ± 0.24 |
| ISU-7229 | 9/22/92 | + | $10^{3.45}$ ± 0.20 |
| ISU-92-11581 | 9/22/92 | + | $10^{2.39}$ ± 0.17 |
| ISU-695 | 10/01/92 | + | $10^{4.49}$ ± 0.20 |
| ISU-79 | 10/01/92 | + | $10^{5.69}$ ± 0.25 |
| ISU-412 | 10/01/92 | + | $10^{5.31}$ ± 0.50 |
| ISU-55 | 10/01/92 | + | $10^{5.54}$ ± 0.10 |
| ISU-33 | 10/05/92 | + | $10^{5.36}$ ± 0.21 |
| ISU-1894 | 10/27/92 | + | $10^{5.18}$ ± 0.33 |
| ISU-04 | 10/27/92 | + | $10^{5.78}$ ± 0.24 |
| ISU-51 | 2/07/93 | + | $10^{4.59}$ ± 0.15 |
| ISU-30262 | 4/01/93 | + | $10^{5.99}$ ± 0.24 |

NOTE: All virus isolates were plaque-purified and propagated on PSP-36-SAH cells.

TABLE 5

| Isolate | Pathogenicity | No. of mRNA's |
|---|---|---|
| ISU-12 | Very pathogenic | 7 |
| ISU-984 | Very pathogenic | 7 |
| ISU-3927 | Mildly pathogenic | 7* |
| ISU-51 | Mildly pathogenic | 7 |
| ISU-22 | Very pathogenic | 9 |
| ISU-55 | Mildly pathogenic | 9 |
| ISU-79 | Very pathogenic | 9 |

*Some mRNA's exhibited deletions.

Samples of each of unplaque-purified ISU-12, plaque-purified ISU-12, ISU-22, ISU-51, ISU-55 and ISU-3927 have been deposited under the terms of the Budapest Treaty at the American Type Culture Collection, 10801 University Boulevard, Manassas, Va. 20110-2209, under the accession numbers VR 2385, VR 2386, VR 2429, VR 2428, VR 2430, and VR 2431, respectively.

The mRNA's of ISU-3927 exhibited deletions in four of the seven mRNA's. mRNA's 4, 5, 6 and 7 of ISU-3927 migrated faster than those of ISU-12, and hence, are smaller than those of ISU-12. This feature may possibly be related to the lower virulence of ISU-3927.

The pathogenicity of six isolates was compared in five-week-old CDCD pigs. Fifteen pigs were inoculated with $10^5$ $TCID_{50}$ of virus. Ten pigs were necropsied at 10 DPI, and five pigs were necropsied at 28 DPI. Virus isolates ISU-12, ISU-22 and ISU-28 were the most pathogenic, whereas ISU-51 and ISU-55 were of low pathogenicity. In a previous study, ISU-3927 was only mildly pathogenic for 5-week old pigs.

Lesions caused by ISU-22 and unplaque-purified (i.e., isolated infectious agent which was not plaque-purified) ISU-12 persist for longer periods than those caused by plaque-purified viruses. The plaque-purified isolates produce mild myocarditis and encephalitis. Unplaque-purified isolates produced slightly more severe disease than the corresponding plaque-purified isolates.

CDCD piglets provide an excellent model for evaluation of the pathogenicity and efficacy of candidate vaccines. The isolates ISU-12, ISU-22 and ISU-984 produce similar lesions, and can be used to evaluate vaccine efficacy, based on examinations of gross and microscopic lesions. ISU-3927 is less virulent, but is adequate for evaluating a vaccine against pathogenic strains of PRRSV.

Pigs infected with plaque-purified ISU-12 gained an average of 9.9 pounds less than control pigs (challenged with uninfected PSP-36 cells) over a time period of 28 days. Preliminary results indicate that a lymphopenia and neutrophilia appear from 2–10 DPI.

Only those pigs infected with unplaque-purified ISU-12 developed significant encephalitis. No rhinitis was observed in any pig challenged with biologically cloned (plaque-purified) Iowa strain isolates. By contrast, rhinitis was severe when tissue filtrates (unplaque-purified isolates) were used as inocula.

The pathology and histology of CDCD pigs infected with ISU-12 unplaque-purified, ISU-12 plaque-purified, ISU-22, ISU-984, ISU-3927 and uninfected PSP-36 cells are summarized in Tables 6–12 below. In these Tables, gross lung lesion scores represent the percentage of lung consolidation (i.e., the percentage of lung tissue diseased with pneumonia, showing lesions). A score is based on a scale of from 0 to 100% consolidation. "ND" means the gross lung lesion score was not determined.

TABLE 6

| Isolate | average score, 3 DPI | average score, 7 DPI | average score, 10 DPI | average score, 21 DPI | average score, 28 DPI | average score, 36 DPI |
|---|---|---|---|---|---|---|
| ISU-12 unpl. | 29 | 56.3 | 77.3 | 37.25 | 6.0 | ND |
| ISU-12 | 20.5 | 35.5 | 77.5 | 25.0 | 0.0 | 0 |
| ISU-22 | 26.5 | 35.0 | 64.75 | 36.5 | 11.0 | 0 |
| ISU-984 | 7.25 | 21.75 | 76.0 | 21.0 | 0.5 | 0 |
| ISU-3927 | 13.5 | 20.0 | 10.5 | 0 | 0.0 | 0 |
| PSP-36 | 0 | 0 | 0 | 0 | 0 | 0 |
| Uninoc. | 0 | 0 | 0 | 0 | 0 | 0 |

In Table 6 above, "unpl." means unplaque-purified, and "uninoc." means uninoculated.

The results in Table 6 above show that ISU-12 and ISU-22 produce lesions which persist longer than other isolates. The lesions produced by ISU-12, ISU-22 and ISU-984 are of similar severity. The lesions produced by ISU-3927 are much less severe, and are resolved earlier than lesions produced by other isolates. All gross lesions were resolved by 36 DPI.

The pathology results presented in Tables 7–12 below are based on the same scale of severity presented for Table 1 above. In Tables 7–12 below, "Int. thick." means interstitial thickening, "alv. exud." means alveolar exudate, and "encephal." means encephalitis.

TABLE 7

Microscopic lesions at 3 DPI

| Lesion | ISU-12 unpl. | ISU-12 | ISU-22 | ISU-984 | ISU-3927 | PSP-36 control |
|---|---|---|---|---|---|---|
| Type II | ++ | + | ++ | − | + | − |
| Syncytia | + | + | + | − | − | − |

TABLE 7-continued

| Microscopic lesions at 3 DPI | | | | | | |
|---|---|---|---|---|---|---|
| Lesion | ISU-12 unpl. | ISU-12 | ISU-22 | ISU-984 | ISU-3927 | PSP-36 control |
| Int. thick. | + | + | + | – | + | – |
| alv. exud. | + | + | + | – | + | – |
| myocarditis | – | – | – | – | – | – |
| encephal. | – | – | – | – | – | – |

TABLE 8

| Microscopic lesions at 7 DPI | | | | | | |
|---|---|---|---|---|---|---|
| Lesion | ISU-12 unpl. | ISU-12 | ISU-22 | ISU-984 | ISU-3927 | PSP-36 control |
| Type II | ++++ | ++ | ++++ | ++++ | ++ | – |
| Syncytia | + | + | ++ | ++ | +/– | – |
| Int. thick. | ++++ | +++ | +++ | ++ | + | – |
| alv. exud. | +++ | ++ | +++ | +++ | ++ | – |
| myocarditis | – | – | – | – | – | – |
| encephal. | – | – | – | – | – | – |

TABLE 9

| Microscopic lesions at 10 DPI | | | | | | |
|---|---|---|---|---|---|---|
| Lesion | ISU-12 unpl. | ISU-12 | ISU-22 | ISU-984 | ISU-3927 | PSP-36 control |
| Type II | ++++ | +++ | +++ | +++ | + | – |
| Syncytia | ++ | ++ | ++ | ++ | – | – |
| Int. thick. | ++++ | +++ | +++ | +++ | + | – |
| alv. exud. | +++ | +++ | +++ | +++ | + | – |
| myocarditis | + | – | – | – | – | – |
| encephal. | + | – | – | – | – | – |

TABLE 10

| Microscopic lesions at 21 DPI | | | | | | |
|---|---|---|---|---|---|---|
| Lesion | ISU-12 unpl. | ISU-12 | ISU-22 | ISU-984 | ISU-3927 | PSP-36 control |
| Type II | ++++ | +++ | +++ | +++ | + | – |
| Syncytia | ++ | + | ++ | ++ | + | – |
| Int. thick. | ++++ | ++ | ++++ | +++ | + | – |
| alv. exud. | +++ | ++ | +++ | ++ | + | – |
| myocarditis | +++ | ++ | ++ | ++ | + | – |
| encephal. | ++ | – | – | – | – | – |

TABLE 11

| Microscopic lesions at 28 DPI | | | | | | |
|---|---|---|---|---|---|---|
| Lesion | ISU-12 unpl. | ISU-12 | ISU-22 | ISU-984 | ISU-3927 | PSP-36 control |
| Type II | ++ | + | ++ | + | + | – |
| Syncytia | + | + | ++ | + | + | – |
| Int. thick. | ++ | + | + | + | + | – |
| alv. exud. | ++ | + | ++ | + | ++ | – |
| myocarditis | ++++ | ++ | ++++ | ++ | + | – |
| encephal. | + | – | – | – | – | – |

TABLE 12

| Microscopic lesions at 36 DPI | | | | | | |
|---|---|---|---|---|---|---|
| Lesion | ISU-12 unpl. | ISU-12 | ISU-22 | ISU-984 | ISU-3927 | PSP-36 control |
| Type II | ND | +/– | +/– | +/– | +/– | – |
| Syncytia | ND | – | – | – | – | – |
| Int. thick. | ND | +/– | +/– | + | – | – |
| alv. exud. | ND | – | +/– | – | +/– | – |
| myocarditis | ND | +/– | – | – | – | – |
| encephal. | ND | – | – | +/– | – | – |

By 7 DPI, lung lesions produced by ISU-12, ISU-22 and ISU-984 are severe, and similar to each other. Lung lesions produced by ISU-3927 are only mild or moderately severe by 7 DPI.

By 10 DPI, the lung lesions produced by ISU-12, ISU-22 and ISU-984 are similar to those at 7 DPI, but a little more severe. Only pigs infected by unplaque-purified ISU-12 exhibit mild encephalitis and myocarditis. By 10 DPI, lesions produced by ISU-3927 are nearly resolved.

By 21 DPI, myocarditis produced by unplaque-purified ISU-12 is severe, whereas myocarditis produced by ISU-12, ISU-22 and ISU-984 is moderate. Only pigs infected by unplaque-purified ISU-12 exhibit moderate encephalitis at 21 DPI.

At 28 DPI, lung lesions are still moderate in pigs infected by unplaque-purified ISU-12 and ISU-22. These isolates also produce severe myocarditis at 28 DPI. However, lung lesions produced by ISU-12, ISU-984 and ISU-3927 are nearly resolved at 28 DPI.

By 36 DPI, all lesions are essentially resolved. Only 1 pig per group was examined at 36 DPI.

Experiment VI

An in vivo cross-neutralization study was performed. CDCD pigs were inoculated intranasally first with an isolate selected from ISU-12, ISU-22, ISU-984 and ISU-3927, then four weeks later, the pigs were challenged with ISU-12. Lung lesions and other disease symptoms were examined 8 DPI after challenging with ISU-12. Control pigs were only challenged with ISU-12. The results are presented in Table 13 below.

The pathology results presented in Table 13 below are based on the same scale of severity presented for Table 1 above. In Table 13 below, "Int. thick." means interstitial thickening, "alv. exud." means alveolar exudate, and "encephal." means encephalitis.

TABLE 13

| In vivo cross neutralization | | | | | |
|---|---|---|---|---|---|
| Lesion | I-12 then I-12 | Cont. then I-12 | I-22 then I-12 | I-984 then I-12 | 3927 then I-12 |
| Type II | + | +++ | +++ | ++ | + |
| Syncytia | – | ++ | ++ | + | + |
| Int. thick. | +/– | +++ | + | ++ | + |
| alv. exud. | + | +++ | +++ | ++ | + |
| myocarditis | + | – | ++++ | +/– | + |
| encephal. | ++ | – | – | – | – |

The data in Table 13 above demonstrate that ISU-12 provides protection for pigs against most symptoms of the disease caused by ISU-12. ISU-984 provides protection against some symptoms and clinical signs of PRRS caused by ISU-12, which is among the most virulent strains of PRRSV virus known.

However, ISU-3927, a mildly pathogenic variant of the Iowa strain of PRRS virus, provides the greatest protection of the isolates studied as a live vaccine against a subsequent challenge with ISU-12. Thus, ISU-3927 may show commercial promise for use as a live vaccine.

Experiement VII

Groups of 10 CDCD pigs were inoculated with isolates of the Iowa strain of PRRSV listed in Table 14 below, or with uninfected PSP-36 cells as a control. The pigs were 5 weeks old when challenged intranasally with $10^5$ $TCID_{50}$ of each virus isolate listed in Table 14 below. The pigs were necropsied at 10 DPI.

The mean gross lung lesion score 10 DPI is provided in Table 13 below as an indication of the pathogenicity of the isolate. The standard deviation (SD) is provided as an indication of the statistical significance of the mean gross lung lesion score.

TABLE 14

| Inocula | N | Mean gross lung score 10 DPI | SD |
|---|---|---|---|
| PSP-36 | 10 | 0.0 | 0.0 |
| ISU-28 | 10 | 62.4 | 20.9 |
| ISU-12 | 10 | 54.3 | 9.8 |
| ISU-79 | 10 | 51.9 | 13.5 |
| ISU-1894 | 10 | 27.4 | 11.7 |
| ISU-55 | 10 | 20.8 | 15.1 |
| ISU-51 | 10 | 16.7 | 9.0 |

A statistical comparison of the gross lung lesion scores is provided in Table 15 below.

TABLE 15

Statistical comparison of gross lung lesion scores

| Comparison | Value of t | p > \|t\| |
|---|---|---|
| Control vs 12 | 9.43 | p < .001 |
| Control vs 28 | 10.83 | p < .001 |

TABLE 15-continued

Statistical comparison of gross lung lesion scores

| Comparison | Value of t | p > \|t\| |
|---|---|---|
| Control vs 51 | 2.89 | p < .01 |
| Control vs 55 | 3.61 | p < .001 |
| Control vs 1894 | 4.76 | p < .001 |
| Control vs 79 | 9.00 | p < .001 |
| 12 vs 28 | 1.41 | p < .2 |
| 12 vs 51 | 6.54 | p < .001 |
| 12 vs 55 | 5.82 | p < .001 |
| 12 vs 79 | 0.43 | p > .5 |
| 12 vs 1894 | 4.76 | p < .001 |
| 28 vs 51 | 7.94 | p < .001 |
| 28 vs 55 | 7.22 | p < .001 |
| 28 vs 79 | 1.83 | p < .1 |
| 28 vs 1894 | 6.06 | p < .001 |
| 51 vs 55 | 0.72 | p < .5 |
| 51 vs 79 | 6.11 | p < .001 |
| 51 vs 1894 | 1.87 | p < .1 |
| 55 vs 79 | 5.39 | p < .001 |
| 55 vs 1894 | 1.15 | p < .3 |
| 79 vs 1894 | 4.24 | p < .001 |

In addition, each group of pigs was examined for respiratory distress according to the clinical respiratory scoring system described above (see "Clinical score mean" in Table 16 below). "Gross score" refers to the gross lung lesion score described above. "Enceph.", "myocard." and "rhinitis" refer to the number of pigs in each group exhibiting lesions of encephalitis, myocarditis and rhinitis, respectively. "Micro score" refers to a score based on the following scale, used to evaluate and compare microscopic lesions of interstitial pneumonia in lung tissue:

| |
|---|
| 0 = no disease; normal lung tissue |
| 1 = mild multifocal microscopic lesions |
| 2 = mild diffuse microscopic lesions |
| 3 = moderate multifocal microscopic lesions |
| 4 = moderate diffuse microscopic lesions |
| 5 = severe multifocal microscopic lesions |
| 6 = severe diffuse microscopic lesions |

Microscopic lesions may be observed in tissues which do not exhibit gross lesions. Thus, the "micro score" provides an additional means for evaluating and comparing the pathogenicity of these isolates, in addition to gross lung lesions, respiratory distress, fever, etc.

TABLE 16

| Isolate | 5 DPI Clinical score mean | 10 DPI Clinical score mean | 10 DPI Gross score mean | 10 DPI Micro score mean | 28 DPI Gross score mean | 28 DPI Micro score mean | Enceph. | Myocard. | Rhinitis |
|---|---|---|---|---|---|---|---|---|---|
| PSP-36 | 0 | 0 | 0 | 0 | 0 | 0.2 | 1/15 | 4/15 | 1/15 |
| ISU-51 | 0.1 | 0.2 | 19.4 | 2.5 | 10.0 | 1.0 | 2/12 | 2/12 | 1/12 |
| ISU-55 | 1.1 | 1.5 | 20.9 | 2.5 | 14.4 | 1.6 | 8/15 | 6/15 | 6/15 |
| ISU-1894 | 2.5 | 1.1 | 26.1 | 2.3 | 46.6 | 2.4 | 7/15 | 4/15 | 9/15 |
| ISU-79 | 3.5 | 2.9 | 51.9 | 3.2 | 32.0 | 3.0 | 6/15 | 11/15 | 4/15 |
| ISU-12 | 1.5 | 1.4 | 54.3 | 4.0 | 43.6 | 3.0 | 9/15 | 3/15 | 4/15 |
| ISU-28 | 1.0 | 3.1 | 64.5 | 3.8 | 8.6 | 1.9 | 10/15 | 10/15 | 8/15 |

Experiment VIII

The mRNA from PSP-36 cells infected with each of ISU-12, ISU-22, ISU-55, ISU-79, ISU-1894 and ISU-3927 was isolated and separated on a 1.5% agarose gel, to achieve better separation of subgenomic mRNA's. Two groups of migration patterns were observed.

Figure 30:
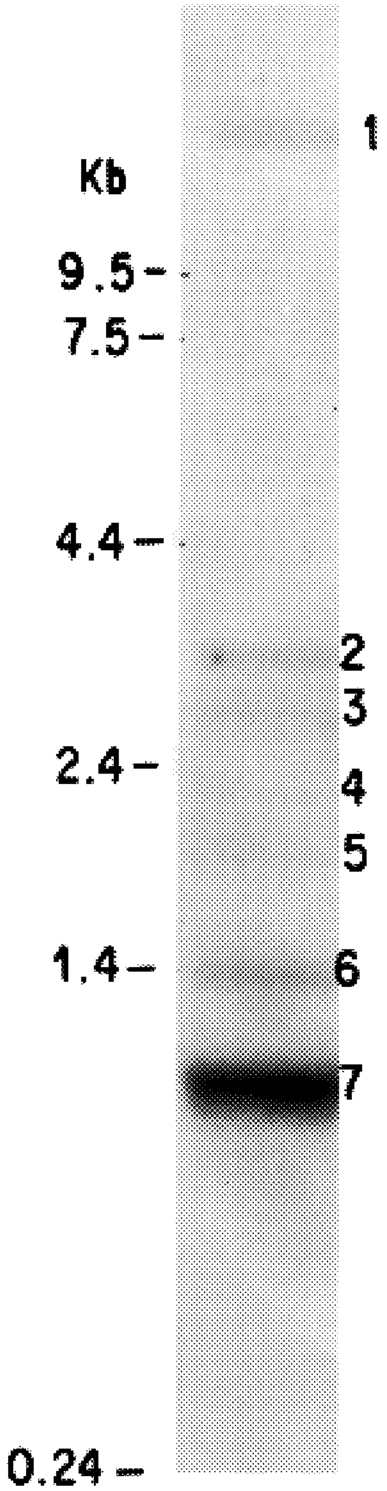
FIG. 30 shows a Northern blot of ISU-12 mRNA.
Figure 31A:
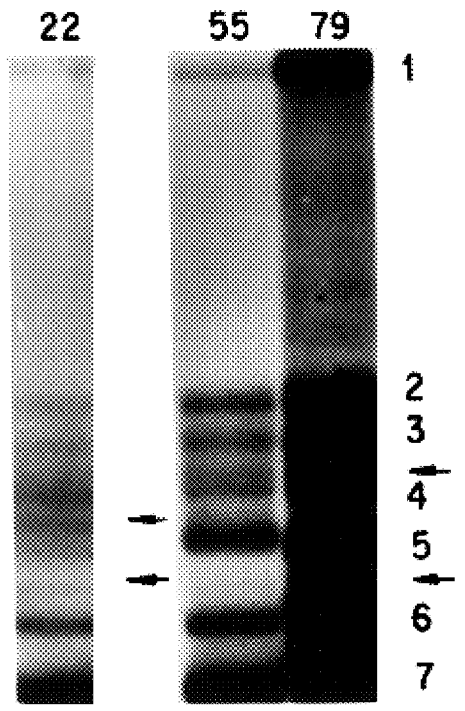
FIGS. 31A and 31B show Northern blots of mRNA taken from other isolates of the Iowa strain of PRRSV (ISU-22, ISU-55, ISU-79, ISU-1894 and ISU-3927)
Figure 31B:
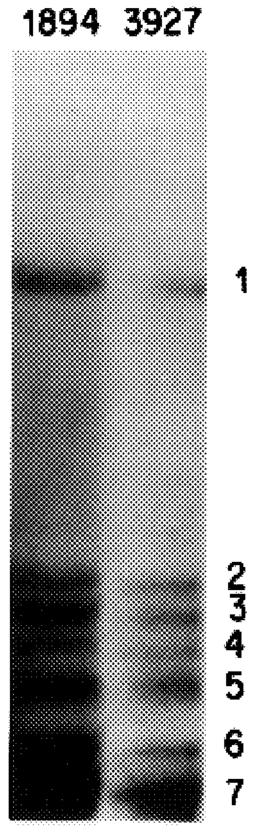

Group I includes isolates ISU-12, ISU-1894, ISU-3927 and possibly, ISU-51. The Northern blot of ISU-12 is shown in FIG. 30, and the Northern blots of ISU-1894, ISU-3927 and ISU-51 are shown in FIG. 31. Like the Lelystad virus, seven subgenomic mRNA's (labelled 1–7 in FIGS. 32 and 33) were found in each of these isolates. The sizes of the subgenomic mRNA's (SgRNA's) are similar to those of the Lelystad virus.

Group II includes isolates ISU-22, ISU-55 and ISU-79. Each of these isolates have nine SgRNA's, instead of seven. SgRNA's 1, 2, 3, 6 and 7 of Group II are the same as those in Group I, but two additional SgRNA's were found between SgRNA's 3 and 6 of Group I, indicated by the arrows in FIG. 33.

Preliminary results indicate that the virus of Group II may replicate better than the isolates of Group I, with the possible exception of ISU-12 in PSP-36 cells. However, in some cases, even ISU-12 may replicate poorly, compared to the isolates of Group II.

Experiment VIII

A porcine reproductive and respiratory syndrome virus (PRRSV) modified live vaccine efficacy study was conducted in 3-week-old, PRRSV-seronegative, SPF pigs. The vaccine consisted of $10^{5.8}$ $TCID_{50}$ of plaque-purified PRRSV ISU-12 (Iowa strain) per 2 ml dose. Nine pigs were given a single vaccine dose by intranasal route (IN), 7 pigs were given a single vaccine dose by intramuscular route (IM), and 9 pigs served as nonvaccinated challenge controls (NV/CHALL). Vaccinates and controls were challenged on post-vaccination day 35, then scored for gross lung lesions (percent of lung affected) on post-challenge day 10.

Figure 32:
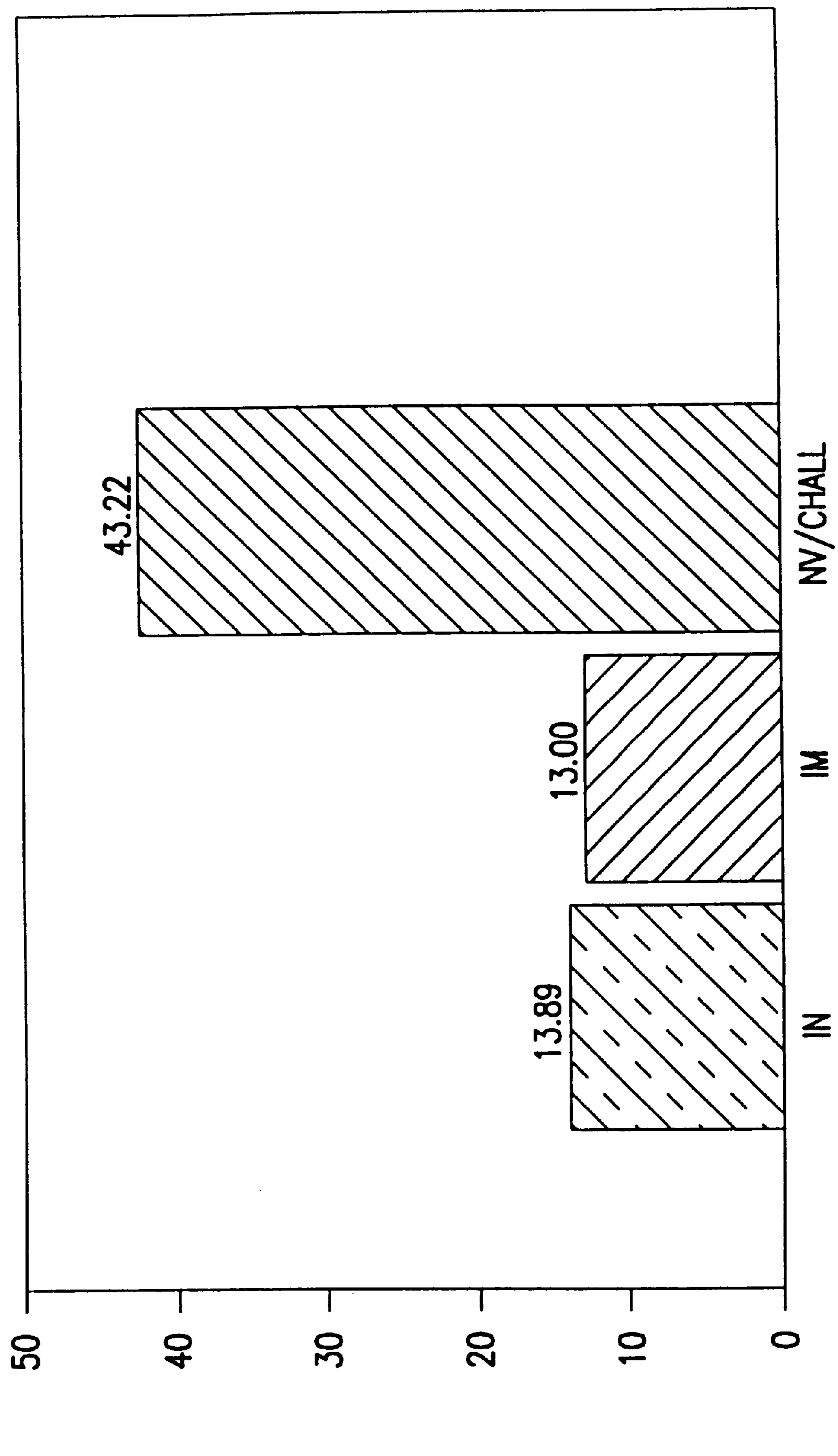
FIG. 32 is a bar graph of the average gross lung lesion scores (percent of lung affected) for groups of 3-week-old, PRRSV-seronegative, specific pathogen-free (SPF) pigs administered one embodiment of the present vaccine intranasally (IN) or intramuscularly (IM), and a group of control pigs (NV/CHALL).

The average gross lung lesion scores for each group of pigs are shown by the number above each bar in FIG. 32. Vaccine efficacy was evaluated by reduction in lung lesion score. Both vaccinate groups demonstrated significantly lower ($p<0.01$) gross lung lesion scores than non-vaccinated controls. Significant differences in scores were not found between vaccinate groups. The ISU-12 PRRSV vaccine was proven efficacious in three-week-old pigs, at the $10^{5.8}$ $TCID_{50}$ dose.

Other Observations

ISU-12 virus is enveloped, as it is sensitive to chloroform treatment. Replication of ISU-12 is resistant to 5-bromodeoxyuridine treatment. Therefore, ISU-12 is not a DNA virus. ISU-12 lacks hemagglutinating activity.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method of producing a vaccine which protects a pig against porcine reproductive and respiratory syndrome (PRRS), comprising the steps of (a) collecting a sample of (1) a naturally occurring isolated virus selected from the group consisting of ISU-51 (VR 2429), ISU-55 (VR 2430), ISU-3927 (VR 2431) AND ISU-1894 (VR 2475); and (2) a naturally occurring isolated virus which causes porcine reproductive and respiratory syndrome (PRRS), wherein inoculation of 5-week-old colostrum-deprived, caesarian-derived pigs with $10^5$ $TCID_{50}$ of said virus results in lesions in at least 51.9% of lung tissue 10 days post infection, and (b) treating said virus in a manner selected from the group consisting of (i) plaque-purifying the virus; (ii) heating said virus at a temperature and for a time sufficient to inactivate said virus; (iii) exposing or mixing said virus with an amount of an inactivating chemical sufficient to inactivate said virus; (iv) breaking down said virus into its corresponding subunits and isolating at least the proteins encoded by open reading frame (ORF)-5, ORF-6 and ORF-7 of the genome of said virus; and (v) synthesizing or isolating a polynucleic acid encoding the proteins encoded by ORF-5, ORF-6 and ORF-7 of the genome of said virus, infecting a suitable host cell with said polynucleic acid, culturing said host cell, and isolating said proteins from said culture; and (c) admixing said treated virus in (b) with a physiological acceptable carrier.

2. The method of claim 1, wherein said virus is collected from a source selected from the group consisting of a culture medium, cells infected with said virus, and both a culture medium and cells infected with said virus.

3. The method of claim 2, further comprising the step of culturing said virus in a suitable medium prior to said collecting step.

* * * * *